US012668793B2

(12) United States Patent
Chee

(10) Patent No.: US 12,668,793 B2
(45) Date of Patent: *Jun. 30, 2026

(54) SEQUENTIAL ENCODING METHODS AND RELATED KITS

(71) Applicant: Encodia, Inc., San Diego, CA (US)

(72) Inventor: Mark S. Chee, San Diego, CA (US)

(73) Assignee: 2026 DF Peptide Acquisition LLC, New York, NY (US)

( * ) Notice: Subject to any disclaimer, the term of this patent is extended or adjusted under 35 U.S.C. 154(b) by 1341 days.

This patent is subject to a terminal disclaimer.

(21) Appl. No.: 17/432,475

(22) PCT Filed: Aug. 16, 2021

(86) PCT No.: PCT/US2021/046164
§ 371 (c)(1),
(2) Date: Aug. 19, 2021

(87) PCT Pub. No.: WO2022/040098
PCT Pub. Date: Feb. 24, 2022

(65) Prior Publication Data
US 2023/0136966 A1 May 4, 2023

Related U.S. Application Data

(60) Provisional application No. 63/067,744, filed on Aug. 19, 2020.

(51) Int. Cl.
*C12N 15/10* (2006.01)

(52) U.S. Cl.
CPC .................................. *C12N 15/1065* (2013.01)

(58) Field of Classification Search
None
See application file for complete search history.

(56) References Cited

U.S. PATENT DOCUMENTS

| | | |
|---|---|---|
| 10,774,372 B2 | 9/2020 | Chee et al. |
| 11,427,814 B2 | 8/2022 | Desai et al. |
| 11,549,942 B2 | 1/2023 | Mallick |
| 11,634,709 B2 | 4/2023 | Chee et al. |
| 11,782,062 B2 | 10/2023 | Chee et al. |
| 2005/0003360 A1 | 1/2005 | Huang |
| 2008/0305957 A1 | 12/2008 | Thisted et al. |

| | | |
|---|---|---|
| 2009/0264300 A1 | 10/2009 | Franch et al. |
| 2011/0143955 A1 | 6/2011 | Weiner |
| 2014/0102915 A1 | 4/2014 | Hu et al. |
| 2016/0060687 A1 | 3/2016 | Zhu et al. |
| 2018/0127744 A1 | 5/2018 | Hu et al. |
| 2018/0267036 A1 | 9/2018 | Fan et al. |
| 2019/0145982 A1* | 5/2019 | Chee .................. G01N 33/6842 435/6.11 |
| 2020/0348308 A1 | 11/2020 | Chee et al. |
| 2021/0171937 A1* | 6/2021 | Pawlosky .......... C12N 15/1048 |
| 2021/0254047 A1 | 8/2021 | Chee et al. |
| 2021/0355483 A1 | 11/2021 | Chee et al. |
| 2021/0396762 A1 | 12/2021 | Chee et al. |
| 2023/0054691 A1 | 2/2023 | Chee et al. |

FOREIGN PATENT DOCUMENTS

| | | | |
|---|---|---|---|
| WO | 2018/204854 A1 | 11/2018 | |
| WO | WO 2019/089836 | 5/2019 | |
| WO | WO 2019/089846 | 5/2019 | |
| WO | WO 2019/089851 | 5/2019 | |
| WO | WO-2019089836 A1 * | 5/2019 | ......... G01N 33/6845 |
| WO | 2020014586 A1 | 1/2020 | |
| WO | WO 2023/114732 | 6/2023 | |

OTHER PUBLICATIONS

U.S. Appl. No. 18/586,030, filed Feb. 23, 2024, by Chee et al. (Copy not provided). (Copy not submitted herewith pursuant to the waiver of 37 C.F. R. § 1.98(a)(2)(iii) issued by the Office on Sep. 21, 2004).
Written Opinion of The International Searching Authority for International application PCT/US2021/046164, dated Dec. 6, 2021, 6 pages.
International Search Report for International application PCT/US2021/046164, dated Dec. 6, 2021, 3 pages.

* cited by examiner

*Primary Examiner* — Juliet C Switzer
*Assistant Examiner* — Brian Ellis Young
(74) *Attorney, Agent, or Firm* — DLA Piper LLP (US)

(57) ABSTRACT

The present disclosure relates to methods and kits for analyzing a macromolecule. In some embodiments, the present disclosure relates to macromolecule analysis methods which employ barcoding and nucleic acid encoding of molecular recognition events. Also provided herein is a method and related kits for transferring information using a plurality of enzymes, including for performing a ligation, extension, and cleavage reaction with nucleic acid molecules associated with the macromolecule for analysis. In some embodiments, the macromolecule for analysis comprises a peptide, a polypeptide, or a protein.

15 Claims, 3 Drawing Sheets

Specification includes a Sequence Listing.

FIG. 2

SEQUENTIAL ENCODING METHODS AND RELATED KITS

RELATED APPLICATION

This application is a U.S. national phase filing of International Patent Application Serial No. PCT/US2021/046164, entitled "SEQUENTIAL ENCODING METHODS AND RELATED KITS." having an international filing date of Aug. 16, 2021, which claims priority to U.S. provisional patent application No. 63/067,744, filed on Aug. 19, 2020. The disclosures and contents of the above-referenced applications are incorporated herein by reference in their entireties for all purposes.

SEQUENCE LISTING ON ASCII TEXT

This patent application file contains a Sequence Listing submitted in computer readable ASCII text format (file name: 4614-2002530_SeqList_ST25.txt, date recorded: Aug. 18, 2021, size: 2,511 bytes). The content of the Sequence Listing file is incorporated herein by reference in its entirety.

TECHNICAL FIELD

The present disclosure relates to methods and kits for analyzing a macromolecule. In some embodiments, the present disclosure relates to macromolecule analysis methods which employ barcoding and nucleic acid encoding of molecular recognition events. Also provided herein are methods and related kits for transferring information using a plurality of enzymes, including for performing a ligation, extension, and cleavage reaction with nucleic acid molecules associated with the macromolecule for analysis. In some embodiments, the macromolecule for analysis comprises a peptide, a polypeptide, or a protein.

BACKGROUND

Highly-parallel characterization and recognition of macromolecules such as proteins remains a challenge. In proteomics, one goal is to identify and quantitate numerous proteins in a sample, which is a formidable task to accomplish in a high-throughput way. Assays such as immunoassays and mass spectrometry based methods have been used but are limited at both the sample and analyte level, with limited sensitivity and dynamic range, with potential issues with cross-reactivity and background signals. Multiplexing the readout of a collection of affinity agents to a collection of cognate macromolecules, for example using affinity agents with detectable labels, remains challenging. There remains a need for improved techniques relating to macromolecule analysis, with applications to protein sequencing and/or analysis, as well as to products, methods and kits for accomplishing the same. There is a need for proteomics technology for performing macromolecule analysis that is efficient, highly-parallelized, accurate, sensitive, and high-throughput. The present disclosure fulfills these and other related needs.

These and other aspects of the invention will be apparent upon reference to the following detailed description. To this end, various references are set forth herein which describe in more detail certain background information, procedures, compounds and/or compositions, and are each hereby incorporated by reference in their entireties.

BRIEF SUMMARY

The summary is not intended to be used to limit the scope of the claimed subject matter. Other features, details, utilities, and advantages of the claimed subject matter will be apparent from the detailed description including those aspects disclosed in the accompanying drawings and in the appended claims.

Provided herein are methods for analyzing a macromolecule including the steps of: providing a macromolecule and an associated recording tag joined to a support; contacting the macromolecule with a binding agent capable of binding to the macromolecule, wherein the binding agent comprises a coding tag with identifying information regarding the binding agent, to allow binding between the macromolecule and the binding agent; joining the 5' end of the recording tag to the 3'end of the coding tag using a nucleic acid joining reagent; extending the recording tag using the coding tag as a template by a polymerase, generating a double stranded extended recording tag; and cleaving the double stranded extended recording tag with a double strand nucleic acid cleaving reagent to generate a 3' overhang in the extended recording tag; whereby information is transferred from the coding tag to the recording tag to generate the extended recording tag.

Provided herein are kits including a binding agent comprising a coding tag, which comprises identifying information regarding the binding agent; a nucleic acid joining reagent; a polymerase; and a double strand nucleic acid cleaving reagent; wherein the binding agent is configured to bind to a macromolecule associated with a recording tag and the identifying information from the coding tag is configured for transfer from the coding tag to the recording tag associated with the macromolecule. In some embodiments, the kit comprises a plurality of binding agents. In some embodiments, the nucleic acid joining reagent, polymerase and double strand nucleic acid cleaving reagent are provided as a mixture.

BRIEF DESCRIPTION OF THE DRAWINGS

Non-limiting embodiments of the present invention will be described by way of example with reference to the accompanying figures, which are schematic and are not intended to be drawn to scale. For purposes of illustration, not every component is labeled in every figure, nor is every component of each embodiment of the invention shown where illustration is not necessary to allow those of ordinary skill in the art to understand the invention.

In FIG. 1A, a macromolecule (e.g., a peptide) to be analyzed is joined to a recording tag hairpin immobilized on a support using a ligation reaction and the structure is cleaved for subsequent steps. First (leftmost) panel of FIG. 1A shows a capture nucleic acid hairpin with recessed 5' phosphorylated end. Second panel of FIG. 1A shows a peptide to be analyzed is attached to a bait nucleic acid which hybridizes to the capture nucleic acid hairpin immobilized on a support (via a reactive coupling moiety). The bait nucleic acid is ligated to the capture nucleic acid. The recording tag is ligated to the hairpin. Block-labeled barcode (BC) indicates any optional barcodes, e.g. sample-specific barcode &/or UMI that can be attached to the macromolecule and incorporated to the recording tag. Block-labeled restriction enzyme recognition site (RS) site represents an incorporated sequence for a type IIS restriction enzyme to recognize and cleave. Third panel of FIG. 1A shows polymerase extension to produce a double stranded DNA (dsDNA) construct with the peptide attached. Fourth panel of FIG. 1A shows the dsDNA construct following digestion with a type IIS RE to produce a 3' overhang (2-base pair sequence) with a recessed 5' phosphorylated end. In this manner, the recording tag containing one or more barcodes is prepared and available for information transfer from a coding tag.

FIG. 1B shows a cycle of encoding with the structure generated in FIG. 1A. The left panel of FIG. 1B shows a binding agent bound to the peptide, bringing a coding tag attached to the binding agent into proximity with the recording tag. In some embodiments, the binding agent can be attached or joined to the coding tag in locations other than depicted (e.g., at the loop region of the coding tag or others). The binding agent as shown is attached to coding tag by a linker. The coding tag contains a binding agent-specific barcode (BBC), a 2 bp spacer, and a type IIS restriction enzyme site (RS). The middle panel of FIG. 1B shows the product of first two enzymatic reactions. Upon ligation of the 5' end of the recording tag to the 3' end of the coding tag, polymerase extends the 3' (non-ligated) end of the recording tag to create a dsDNA molecule containing 2-base pair spacers adjacent to their respective type IIS RE sites. Following double stranding, the type IIS RE binds and cuts adjacent to its recognition site. The right panel of FIG. 1B illustrates the final product after all 3 enzymatic steps, where the dsDNA now contains the binding agent-specific barcode and a 2 nt 3' overhang (OH) which serves as the spacer sequence. In some embodiments, after a cycle of information transfer, a portion of the polypeptide for analysis can be removed from the polypeptide. The cycle of steps shown in FIG. 1B may be repeated one or more times with additional binding agents and coding tags to further extend the recording tag.

FIG. 2. Exemplary encoding results generated by the encoding method shown in FIG. 1A-FIG. 1B. Two test polypeptides (F-peptide; SEQ ID NO: 6 and L-peptide; SEQ ID NO: 7) were joined to immobilized bead-attached nucleic acid recording tags. Two binding agents (F-binder and L-binder) attached to the corresponding coding tags were used to contact the test polypeptides. For ligation step, 3 different concentrations of T4 DNA ligase were tested. After ligation, Klenow fragment was added for the extension step and BtsI-V2 enzyme was added for the cleavage step. Fractions of encoded recording tags were evaluated by NGS sequencing and showed specific encoding results for both binding agents. Each error bar is constructed using 1 standard error from the mean.

DETAILED DESCRIPTION

Figure 1A:
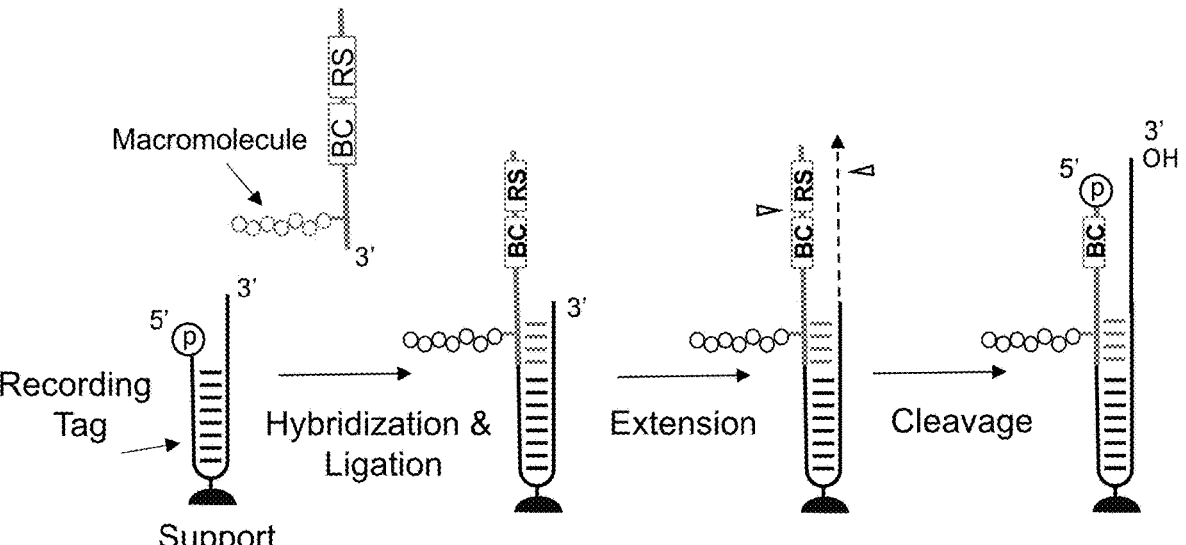
FIG. 1A-FIG. 1B depict an exemplary macromolecule analysis assay involving information transfer using the methods provided herein.

Provided herein are methods and kits for analyzing a macromolecule. In some embodiments, the analysis employs barcoding and nucleic acid encoding of molecular recognition events. The provided method comprises: (a) providing a macromolecule and an associated recording tag joined to a support; (b) contacting the macromolecule with a binding agent capable of binding to the macromolecule, wherein the binding agent comprises a coding tag with identifying information regarding the binding agent, to allow binding between the macromolecule and the binding agent; (c) joining the 5' end of the recording tag to the 3'end of the coding tag using a nucleic acid joining reagent; (d) extending the recording tag using the coding tag as a template by a polymerase, generating a double stranded extended recording tag; and (e) cleaving the double stranded extended recording tag with a double strand nucleic acid cleaving reagent to generate a 3' overhang in the extended recording tag. Performing these steps, information is transferred from the coding tag to the recording tag to generate an extended recording tag. Also provided are kits containing components and/or reagents for performing the provided methods for macromolecule sequencing and/or analysis. In some embodiments, the kits also include instructions for using the kit to perform any of the methods provided herein.

Highly-parallel characterization and recognition of macromolecules such as proteins remains a challenge. In proteomics, one goal is to identify and quantitate numerous proteins in a sample, which is a formidable task to accomplish in a high-throughput way. Assays such as immunoassays and mass spectrometry based methods have been used but are limited at both the sample and analyte level, limited sensitivity and dynamic range, and cross-reactivity and background signals. Multiplexing the readout of a collection of affinity agents to a collection of cognate macromolecules, for example using affinity agents with detectable labels, remains challenging. There remains a need for improved techniques relating to macromolecule analysis, with applications to protein sequencing and/or analysis, as well as to products, methods and kits for accomplishing the same. There is a need for proteomics technology for performing macromolecule analysis that is efficient, highly-parallelized, accurate, sensitive, and high-throughput. The present disclosure fulfills these and other related needs.

In some embodiments, the present disclosure provides, in part, methods for analyzing a macromolecule which includes information transfer, with direct applications to protein and peptide characterization, quantitation, and/or sequencing. In some examples, the information transferred comprises identifying information regarding a binding agent that is configured to bind to the macromolecule. In some embodiments, a plurality of macromolecules obtained from a sample is analyzed. In some embodiments, the sample is obtained from a subject. In some embodiments, the macromolecule sequencing or analysis method includes using a plurality of binding agents associated with coding tags to detect a plurality of macromolecules to be analyzed.

The information transfer methods provided herein utilize a plurality of enzymes to perform ligation, extension, and cleavage reactions with nucleic acid molecules. In some embodiments, the provided methods includes an oligonucleotides that comprise hairpin structure and a restriction enzyme site (or portion thereof). In some embodiments, the methods include the use of a reaction system wherein mixed enzymes are provided to the reaction. For example, the activities of the polymerase, the nucleic acid joining reagent and the double strand nucleic acid cleaving reagent, are provided with suitable conditions, transferring information from a coding tag to the recording tag to generate an extended recording tag. In the provided methods, the recording tag used comprises at least a partially double stranded DNA structure. Some advantages using the described methods include high information transfer (encoding) success, simple design for a step-wise reaction, option to perform in a single step/as a single pot reaction, reducing the need for spacers or reducing spacer length, and/or minimizing DNA-DNA interactions in the system.

Numerous specific details are set forth in the following description in order to provide a thorough understanding of the present disclosure. These details are provided for the purpose of example and the claimed subject matter may be practiced according to the claims without some or all of these specific details. It is to be understood that other embodiments can be used and structural changes can be made without departing from the scope of the claimed subject matter. It should be understood that the various features and functionality described in one or more of the individual embodiments are not limited in their applicability to the particular embodiment with which they are described. They instead can be applied, alone or in some combination, to one or more of the other embodiments of the disclosure, whether or not such embodiments are described, and whether or not such features are presented as being a part of a described embodiment. For the purpose of clarity, technical material that is known in the technical fields related to the claimed subject matter has not been described in detail so that the claimed subject matter is not unnecessarily obscured.

All publications, including patent documents, scientific articles and databases, referred to in this application are incorporated by reference in their entireties for all purposes to the same extent as if each individual publication were individually incorporated by reference. Citation of the publications or documents is not intended as an admission that any of them is pertinent prior art, nor does it constitute any admission as to the contents or date of these publications or documents.

All headings are for the convenience of the reader and should not be used to limit the meaning of the text that follows the heading, unless so specified.

Definitions

Unless defined otherwise, all technical and scientific terms used herein have the same meaning as is commonly understood by one of ordinary skill in the art to which the present disclosure belongs. If a definition set forth in this section is contrary to or otherwise inconsistent with a definition set forth in the patents, applications, published applications and other publications that are herein incorporated by reference, the definition set forth in this section prevails over the definition that is incorporated herein by reference.

As used herein, the singular forms "a," "an" and "the" include plural referents unless the context clearly dictates otherwise. Thus, for example, reference to "a peptide" includes one or more peptides, or mixtures of peptides. Also, and unless specifically stated or obvious from context, as used herein, the term "or" is understood to be inclusive and covers both "or" and "and".

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X.

The term "antibody" herein is used in the broadest sense and includes polyclonal and monoclonal antibodies, including intact antibodies and functional (antigen-binding) antibody fragments, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

An "individual" or "subject" includes a mammal. Mammals include, but are not limited to, domesticated animals (e.g., cows, sheep, cats, dogs, and horses), primates (e.g., humans and non-human primates such as monkeys), rabbits, and rodents (e.g., mice and rats). An "individual" or "subject" may include birds such as chickens, vertebrates such as fish and mammals such as mice, rats, rabbits, cats, dogs, pigs, cows, ox, sheep, goats, horses, monkeys and other non-human primates. In certain embodiments, the individual or subject is a human.

As used herein, the term "sample" refers to anything which may contain an analyte for which an analyte assay is desired. As used herein, a "sample" can be a solution, a suspension, liquid, powder, a paste, aqueous, non-aqueous or any combination thereof. The sample may be a biological sample, such as a biological fluid or a biological tissue. Examples of biological fluids include urine, blood, plasma, serum, saliva, semen, stool, sputum, cerebral spinal fluid, tears, mucus, amniotic fluid or the like. Biological tissues are aggregate of cells, usually of a particular kind together with their intercellular substance that form one of the structural materials of a human, animal, plant, bacterial, fungal or viral structure, including connective, epithelium, muscle and nerve tissues. Examples of biological tissues also include organs, tumors, lymph nodes, arteries and individual cell(s).

In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma.

The terms "level" or "levels" are used to refer to the presence and/or amount of a target, e.g., a substance or an organism that is part of the etiology of a disease or disorder, and can be determined qualitatively or quantitatively. A "qualitative" change in the target level refers to the appearance or disappearance of a target that is not detectable or is present in samples obtained from normal controls. A "quantitative" change in the levels of one or more targets refers to a measurable increase or decrease in the target levels when compared to a healthy control.

As used herein, the term "macromolecule" encompasses large molecules composed of smaller subunits. Examples of macromolecules include, but are not limited to peptides, polypeptides, proteins, nucleic acids, carbohydrates, lipids, macrocycles, or a combination or complex thereof. A macromolecule also includes a chimeric macromolecule composed of a combination of two or more types of macromolecules, covalently linked together (e.g., a peptide linked to a nucleic acid). A macromolecule may also include a "macromolecule assembly", which is composed of non-covalent complexes of two or more macromolecules. A macromolecule assembly may be composed of the same type of macromolecule (e.g., protein-protein) or of two or more different types of macromolecules (e.g., protein-DNA).

As used herein, the term "polypeptide" encompasses peptides and proteins, and refers to a molecule comprising a chain of two or more amino acids joined by peptide bonds. In some embodiments, a polypeptide comprises 2 to 50 amino acids, e.g., having more than 20-30 amino acids. In some embodiments, a peptide does not comprise a secondary, tertiary, or higher structure. In some embodiments, the polypeptide is a protein. In some embodiments, a protein comprises 30 or more amino acids, e.g. having more than 50 amino acids. In some embodiments, in addition to a primary structure, a protein comprises a secondary, tertiary, or higher structure. The amino acids of the polypeptides are most typically L-amino acids, but may also be D-amino acids, modified amino acids, amino acid analogs, amino acid mimetics, or any combination thereof. Polypeptides may be naturally occurring, synthetically produced, or recombinantly expressed. Polypeptides may be synthetically produced, isolated, recombinantly expressed, or be produced by a combination of methodologies as described above. Polypeptides may also comprise additional groups modifying the amino acid chain, for example, functional groups added via post-translational modification. The polymer may be linear or branched, it may comprise modified amino acids, and it may be interrupted by non-amino acids. The term also encompasses an amino acid polymer that has been modified naturally or by intervention; for example, disulfide bond formation, glycosylation, lipidation, acetylation, phosphorylation, or any other manipulation or modification, such as conjugation with a labeling component.

As used herein, the term "amino acid" refers to an organic compound comprising an amine group, a carboxylic acid group, and a side-chain specific to each amino acid, which serve as a monomeric subunit of a peptide. An amino acid includes the 20 standard, naturally occurring or canonical amino acids as well as non-standard amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). An amino acid may be an L-amino acid or a D-amino acid. Non-standard amino acids may be modified amino acids, amino acid analogs, amino acid mimetics, non-standard proteinogenic amino acids, or non-proteinogenic amino acids that occur naturally or are chemically synthesized. Examples of non-standard amino acids include, but are not limited to, selenocysteine, pyrrolysine, and N-formylmethionine, β-amino acids, Homo-amino acids, Proline and Pyruvic acid derivatives, 3-substituted alanine derivatives, glycine derivatives, ring-substituted phenylalanine and tyrosine derivatives, linear core amino acids, N-methyl amino acids.

As used herein, the term "post-translational modification" refers to modifications that occur on a peptide after its translation, e.g., translation by ribosomes, is complete. A post-translational modification may be a covalent chemical modification or enzymatic modification.

Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini. The term post-translational modification can also include peptide modifications that include one or more detectable labels.

As used herein, the term "binding agent" refers to a nucleic acid molecule, a peptide, a polypeptide, a protein, carbohydrate, or a small molecule that binds to, associates, unites with, recognizes, or combines with a binding target, e.g., a polypeptide or a component or feature of a polypeptide. A binding agent may form a covalent association or non-covalent association with the polypeptide or component or feature of a polypeptide. A binding agent may also be a chimeric binding agent, composed of two or more types of molecules, such as a nucleic acid molecule-peptide chimeric binding agent or a carbohydrate-peptide chimeric binding agent. A binding agent may be a naturally occurring, synthetically produced, or recombinantly expressed molecule. A binding agent may bind to a single monomer or subunit of a polypeptide (e.g., a single amino acid of a polypeptide) or bind to a plurality of linked subunits of a polypeptide (e.g., a di-peptide, tri-peptide, or higher order peptide of a longer peptide, polypeptide, or protein molecule). A binding agent may bind to a linear molecule or a molecule having a three-dimensional structure (also referred to as conformation). For example, an antibody binding agent may bind to linear peptide, polypeptide, or protein, or bind to a conformational peptide, polypeptide, or protein. A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may preferably bind to a chemically modified or labeled amino acid (e.g., an amino acid that has been labeled by a chemical reagent) over a non-modified or unlabeled amino acid. For example, a binding agent may preferably bind to an amino acid that has been labeled or modified over an amino acid that is unlabeled or unmodified. A binding agent may bind to a post-translational modification of a peptide molecule. A binding agent may exhibit selective binding to a component or feature of a polypeptide (e.g., a binding agent may selectively bind to one of the 20 possible natural amino acid residues and bind with very low affinity or not at all to the other 19 natural amino acid residues). A binding agent may exhibit less selective binding, where the binding agent is capable of binding or configured to bind to a plurality of components or features of a polypeptide (e.g., a binding agent may bind with similar affinity to two or more different amino acid residues). A binding agent may comprise a coding tag, which may be joined to the binding agent by a linker.

As used herein, the term "linker" refers to one or more of a nucleotide, a nucleotide analog, an amino acid, a peptide, a polypeptide, a polymer, or a non-nucleotide chemical moiety that is used to join two molecules. A linker may be used to join a binding agent with a coding tag, a recording tag with a polypeptide, a polypeptide with a support, a recording tag with a solid support, etc. In certain embodiments, a linker joins two molecules via enzymatic reaction or chemistry reaction (e.g., click chemistry).

The term "ligand" as used herein refers to any molecule or moiety connected to the compounds described herein. "Ligand" may refer to one or more ligands attached to a compound. In some embodiments, the ligand is a pendant group or binding site (e.g., the site to which the binding agent binds).

As used herein, the term "proteome" can include the entire set of proteins, polypeptides, or peptides (including conjugates or complexes thereof) expressed by a genome, cell, tissue, or organism at a certain time, of any organism. In one aspect, it is the set of expressed proteins in a given type of cell or organism, at a given time, under defined conditions. Proteomics is the study of the proteome. For example, a "cellular proteome" may include the collection of proteins found in a particular cell type under a particular set of environmental conditions, such as exposure to hormone stimulation. An organism's complete proteome may include the complete set of proteins from all of the various cellular proteomes. A proteome may also include the collection of proteins in certain sub-cellular biological systems. For example, all of the proteins in a virus can be called a viral proteome. As used herein, the term "proteome" include subsets of a proteome, including but not limited to a kinome; a secretome; a receptome (e.g., GPCRome); an immunoproteome; a nutriproteome; a proteome subset defined by a post-translational modification (e.g., phosphorylation, ubiquitination, methylation, acetylation, glycosylation, oxidation, lipidation, and/or nitrosylation), such as a phosphoproteome (e.g., phosphotyrosine-proteome, tyrosine-kinome, and tyrosine-phosphatome), a glycoproteome, etc.; a proteome subset associated with a tissue or organ, a developmental stage, or a physiological or pathological condition; a proteome subset associated a cellular process, such as cell cycle, differentiation (or de-differentiation), cell death, senescence, cell migration, transformation, or metastasis; or any combination thereof. As used herein, the term "proteomics" refers to quantitative analysis of the proteome within cells, tissues, and bodily fluids, and the corresponding spatial distribution of the proteome within the cell and within tissues. Additionally, proteomics studies include the dynamic state of the proteome, continually changing in time as a function of biology and defined biological or chemical stimuli.

The terminal amino acid at one end of a peptide or polypeptide chain that has a free amino group is referred to herein as the "N-terminal amino acid" (NTAA). The terminal amino acid at the other end of the chain that has a free carboxyl group is referred to herein as the "C-terminal amino acid" (CTAA). The amino acids making up a peptide may be numbered in order, with the peptide being "n" amino acids in length. As used herein, NTAA is considered the $n^{th}$ amino acid (also referred to herein as the "n NTAA"). Using this nomenclature, the next amino acid is the n−1 amino acid, then the n−2 amino acid, and so on down the length of the peptide from the N-terminal end to C-terminal end. In certain embodiments, an NTAA, CTAA, or both may be modified or labeled with a moiety or a chemical moiety.

As used herein, the term "barcode" refers to a nucleic acid molecule of about 2 to about 30 bases (e.g., 2, 3, 4, 5, 6, 7, 8, 9, 10, 11, 12, 13, 14, 15, 16, 17, 18, 19, 20, 21, 22, 23, 24, 25, 26, 27, 28, 29 or 30 bases) providing a unique identifier tag or origin information for a polypeptide, a binding agent, a set of binding agents from a binding cycle, a sample polypeptides, a set of samples, polypeptides within a compartment (e.g., droplet, bead, or separated location), polypeptides within a set of compartments, a fraction of polypeptides, a set of polypeptide fractions, a spatial region or set of spatial regions, a library of polypeptides, or a library of binding agents. A barcode can be an artificial sequence or a naturally occurring sequence. In certain embodiments, each barcode within a population of barcodes is different. In other embodiments, a portion of barcodes in a population of barcodes is different, e.g., at least about 10%, 15%, 20%, 25%, 30%, 35%, 40%, 45%, 50%, 55%, 60%, 65%, 70%, 75%, 80%, 85%, 90%, 95%, 97%, or 99% of the barcodes in a population of barcodes is different. A population of barcodes may be randomly generated or non-randomly generated. In certain embodiments, a population of barcodes are error-correcting or error-tolerant barcodes. Barcodes can be used to computationally deconvolute the multiplexed sequencing data and identify sequence reads derived from an individual polypeptide, sample, library, etc. A barcode can also be used for deconvolution of a collection of polypeptides that have been distributed into small compartments for enhanced mapping. For example, rather than mapping a peptide back to the proteome, the peptide is mapped back to its originating protein molecule or protein complex.

As used herein, the term "coding tag" refers to a polynucleotide with any suitable length, e.g., a nucleic acid molecule of about 2 bases to about 100 bases, including any integer including 2 and 100 and in between, that comprises identifying information for its associated binding agent. A "coding tag" may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety). A coding tag may comprise an encoder sequence, which is optionally flanked by one spacer on one side or optionally flanked by a spacer on each side. A coding tag may also be comprised of an optional UMI and/or an optional binding cycle-specific barcode. A coding tag may be single stranded or double stranded. A double stranded coding tag may comprise blunt ends, overhanging ends, or both. A coding tag may refer to the coding tag that is directly attached to a binding agent, to a complementary sequence hybridized to the coding tag directly attached to a binding agent (e.g., for double stranded coding tags), or to coding tag information present in an extended recording tag. In certain embodiments, a coding tag may further comprise a binding cycle specific spacer or barcode, a unique molecular identifier, a universal priming site, or any combination thereof.

As used herein, the term "spacer" (Sp) refers to a nucleic acid molecule of about 1 base to about 20 bases (e.g., 1, 2, 3, 4, 5, 6, 7, 8, 9, 10, 11, 12, 13, 14, 15, 16, 17, 18, 19, or 20 bases) in length that is present on a terminus of a recording tag or coding tag. In certain embodiments, a spacer sequence flanks an encoder sequence of a coding tag on one end or both ends. Following binding of a binding agent to a polypeptide, annealing between complementary spacer sequences on their associated coding tag and recording tag, respectively, allows transfer of binding information through a primer extension reaction or ligation to the recording tag, coding tag, or a di-tag construct. Sp' refers to spacer sequence complementary to Sp. Preferably, spacer sequences within a library of binding agents possess the same number of bases. A common (shared or identical) spacer may be used in a library of binding agents. A spacer sequence may have a "cycle specific" sequence in order to track binding agents used in a particular binding cycle. The spacer sequence (Sp) can be constant across all binding cycles, be specific for a particular class of polypeptides, or be binding cycle number specific. Polypeptide class-specific spacers permit annealing of a cognate binding agent's coding tag information present in an extended recording tag from a completed binding/extension cycle to the coding tag of another binding agent recognizing the same class of polypeptides in a subsequent binding cycle via the class-specific spacers. Only the sequential binding of correct cognate pairs results in interacting spacer elements and effective primer extension. A spacer sequence may comprise sufficient number of bases to anneal to a complementary spacer sequence in a recording tag to initiate a primer extension (also referred to as polymerase extension) reaction, or provide a "splint" for a ligation reaction, or mediate a "sticky end" ligation reaction. A spacer sequence may comprise a fewer number of bases than the encoder sequence within a coding tag.

As used herein, the term "recording tag" refers to a moiety, e.g., a chemical coupling moiety, a nucleic acid molecule, or a sequenceable polymer molecule (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety) to which identifying information of a coding tag can be transferred, or from which identifying information about the macromolecule (e.g., UMI information) associated with the recording tag can be transferred to the coding tag. Identifying information can comprise any information characterizing a molecule such as information pertaining to sample, fraction, partition, spatial location, interacting neighboring molecule(s), cycle number, etc. Additionally, the presence of UMI information can also be classified as identifying information. In certain embodiments, after a binding agent binds to a polypeptide, information from a coding tag linked to a binding agent can be transferred to the recording tag associated with the polypeptide while the binding agent is bound to the polypeptide. In other embodiments, after a binding agent binds to a polypeptide, information from a recording tag associated with the polypeptide can be transferred to the coding tag linked to the binding agent while the binding agent is bound to the polypeptide. A recording tag may be directly linked to a polypeptide, linked to a polypeptide via a multifunctional linker, or associated with a polypeptide by virtue of its proximity (or co-localization) on a support. A recording tag may be linked via its 5' end or 3' end or at an internal site, as long as the linkage is compatible with the method used to transfer coding tag information to the recording tag or vice versa. A recording tag may further comprise other functional components, e.g., a universal priming site, unique molecular identifier, a barcode (e.g., a sample barcode, a fraction barcode, spatial barcode, a compartment tag, etc.), a spacer sequence that is complementary to a spacer sequence of a coding tag, or any combination thereof. The spacer sequence of a recording tag is preferably at the 3'-end of the recording tag in embodiments where polymerase extension is used to transfer coding tag information to the recording tag.

As used herein, the term "primer extension", also referred to as "polymerase extension", refers to a reaction catalyzed by a nucleic acid polymerase (e.g., DNA polymerase) whereby a nucleic acid molecule (e.g., oligonucleotide primer, spacer sequence) that anneals to a complementary strand is extended by the polymerase, using the complementary strand as template.

As used herein, the term "unique molecular identifier" or "UMI" refers to a nucleic acid molecule of about 3 to about 40 bases (3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 bases) in length providing a unique identifier tag for each macromolecule, polypeptide or binding agent to which the UMI is linked. A polypeptide UMI can be used to computationally deconvolute sequencing data from a plurality of extended recording tags to identify extended recording tags that originated from an individual polypeptide. A polypeptide UMI can be used to accurately count originating polypeptide molecules by collapsing NGS reads to unique UMIs. A binding agent UMI can be used to identify each individual molecular binding agent that binds to a particular polypeptide. For example, a UMI can be used to identify the number of individual binding events for a binding agent specific for a single amino acid that occurs for a particular peptide molecule. It is understood that when UMI and barcode are both referenced in the context of a binding agent or polypeptide, that the barcode refers to identifying information other that the UMI for the individual binding agent or polypeptide (e.g., sample barcode, compartment barcode, binding cycle barcode).

As used herein, the term "universal priming site" or "universal primer" or "universal priming sequence" refers to a nucleic acid molecule, which may be used for library amplification and/or for sequencing reactions. A universal priming site may include, but is not limited to, a priming site (primer sequence) for PCR amplification, flow cell adaptor sequences that anneal to complementary oligonucleotides on flow cell surfaces enabling bridge amplification in some next generation sequencing platforms, a sequencing priming site, or a combination thereof. Universal priming sites can be used for other types of amplification, including those commonly used in conjunction with next generation digital sequencing. For example, extended recording tag molecules may be circularized and a universal priming site used for rolling circle amplification to form DNA nanoballs that can be used as sequencing templates (Drmanac et al., 2009, Science 327:78-81). Alternatively, recording tag molecules may be circularized and sequenced directly by polymerase extension from universal priming sites (Korlach et al., 2008, Proc. Natl. Acad. Sci. 105:1176-1181). The term "forward" when used in context with a "universal priming site" or "universal primer" may also be referred to as "5'" or "sense".

The term "reverse" when used in context with a "universal priming site" or "universal primer" may also be referred to as "3'" or "antisense".

As used herein, the term "extended recording tag" refers to a recording tag to which information of at least one binding agent's coding tag (or its complementary sequence) has been transferred following binding of the binding agent to a polypeptide. Information of the coding tag may be transferred to the recording tag directly (e.g., ligation) or indirectly (e.g., primer extension). Information of a coding tag may be transferred to the recording tag enzymatically or chemically. An extended recording tag may comprise binding agent information of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 55, 60, 65, 70, 75, 80, 85, 90, 95, 100, 125, 150, 175, 200 or more coding tags. The base sequence of an extended recording tag may reflect the temporal and sequential order of binding of the binding agents identified by their coding tags, may reflect a partial sequential order of binding of the binding agents identified by the coding tags, or may not reflect any order of binding of the binding agents identified by the coding tags. In certain embodiments, the coding tag information present in the extended recording tag represents with at least 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, or 100% identity the polypeptide sequence being analyzed. In certain embodiments where the extended recording tag does not represent the polypeptide sequence being analyzed with 100% identity, errors may be due to off-target binding by a binding agent, or to a "missed" binding cycle (e.g., because a binding agent fails to bind to a polypeptide during a binding cycle, because of a failed primer extension reaction), or both.

As used herein, the term "solid support", "solid surface", or "solid substrate", or "sequencing substrate", or "substrate" refers to any solid material, including porous and non-porous materials, to which a polypeptide can be associated directly or indirectly, by any means known in the art, including covalent and non-covalent interactions, or any combination thereof. A solid support may be two-dimensional (e.g., planar surface) or three-dimensional (e.g., gel matrix or bead). A solid support can be any support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a silicon wafer chip, a flow through chip, a flow cell, a biochip including signal transducing electronics, a channel, a microtiter well, an ELISA plate, a spinning interferometry disc, a nitrocellulose membrane, a nitrocellulose-based polymer surface, a polymer matrix, a nanoparticle, or a microsphere. Materials for a solid support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. Solid supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, a controlled pore bead, a silica-based bead, or any combinations thereof. A bead may be spherical or an irregularly shaped. A bead or support may be porous. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 µm in diameter. In certain embodiments, "a bead" solid support may refer to an individual bead or a plurality of beads. In some embodiments, the solid surface is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, between about 100 nm and about 200 nm, or between about 200 nm and about 500 nm in diameter. In some embodiments, the nanoparticles can be about 10 nm, about 50 nm, about 100 nm, about 150 nm, about 200 nm, about 300 nm, or about 500 nm in diameter. In some embodiments, the nanoparticles are less than about 200 nm in diameter.

As used herein, the term "nucleic acid molecule" or "polynucleotide" refers to a single- or double-stranded polynucleotide containing deoxyribonucleotides or ribonucleotides that are linked by 3'-5' phosphodiester bonds, as well as polynucleotide analogs. A nucleic acid molecule includes, but is not limited to, DNA, RNA, and cDNA. A polynucleotide analog may possess a backbone other than a standard phosphodiester linkage found in natural polynucleotides and, optionally, a modified sugar moiety or moieties other than ribose or deoxyribose. Polynucleotide analogs contain bases capable of hydrogen bonding by Watson-Crick base pairing to standard polynucleotide bases, where the analog backbone presents the bases in a manner to permit such hydrogen bonding in a sequence-specific fashion between the oligonucleotide analog molecule and bases in a standard polynucleotide. Examples of polynucleotide analogs include, but are not limited to xeno nucleic acid (XNA), bridged nucleic acid (BNA), glycol nucleic acid (GNA), peptide nucleic acids (PNAs), γPNAs, morpholino polynucleotides, locked nucleic acids (LNAs), threose nucleic acid (TNA), 2'-O-Methyl polynucleotides, 2'-O-alkyl ribosyl substituted polynucleotides, phosphorothioate polynucleotides, and boronophosphate polynucleotides. A polynucleotide analog may possess purine or pyrimidine analogs, including for example, 7-deaza purine analogs, 8-halopurine analogs, 5-halopyrimidine analogs, or universal base analogs that can pair with any base, including hypoxanthine, nitroazoles, isocarbostyril analogues, azole carboxamides, and aromatic triazole analogues, or base analogs with additional functionality, such as a biotin moiety for affinity binding. In some embodiments, the nucleic acid molecule or oligonucleotide is a modified oligonucleotide. In some embodiments, the nucleic acid molecule or oligonucleotide is a DNA with pseudo-complementary bases, a DNA with protected bases, an RNA molecule, a BNA molecule, an XNA molecule, a LNA molecule, a PNA molecule, a γPNA molecule, or a morpholino DNA, or a combination thereof. In some embodiments, the nucleic acid molecule or oligonucleotide is backbone modified, sugar modified, or nucleobase modified. In some embodiments, the nucleic acid molecule or oligonucleotide has nucleobase protecting groups such as Alloc, electrophilic protecting groups such as thiranes, acetyl protecting groups, nitrobenzyl protecting groups, sulfonate protecting groups, or traditional base-labile protecting groups.

As used herein, "nucleic acid sequencing" means the determination of the order of nucleotides in a nucleic acid molecule or a sample of nucleic acid molecules.

As used herein, "next generation sequencing" refers to high-throughput sequencing methods that allow the sequencing of millions to billions of molecules in parallel. Examples of next generation sequencing methods include sequencing by synthesis, sequencing by ligation, sequencing by hybridization, polony sequencing, ion semiconductor sequencing, and pyrosequencing. By attaching primers to a solid substrate and a complementary sequence to a nucleic acid molecule, a nucleic acid molecule can be hybridized to the solid substrate via the primer and then multiple copies can be generated in a discrete area on the solid substrate by using polymerase to amplify (these groupings are sometimes referred to as polymerase colonies or polonies). Consequently, during the sequencing process, a nucleotide at a particular position can be sequenced multiple times (e.g., hundreds or thousands of times)—this depth of coverage is referred to as "deep sequencing." Examples of high throughput nucleic acid sequencing technology include platforms provided by Illumina, BGI, Qiagen, Thermo-Fisher, and Roche, including formats such as parallel bead arrays, sequencing by synthesis, sequencing by ligation, capillary electrophoresis, electronic microchips, "biochips," microarrays, parallel microchips, and single-molecule arrays (See e.g., Service, Science (2006) 311:1544-1546).

As used herein, "single molecule sequencing" or "third generation sequencing" refers to next-generation sequencing methods wherein reads from single molecule sequencing instruments are generated by sequencing of a single molecule of DNA. Unlike next generation sequencing methods that rely on amplification to clone many DNA molecules in parallel for sequencing in a phased approach, single molecule sequencing interrogates single molecules of DNA and does not require amplification or synchronization. Single molecule sequencing includes methods that need to pause the sequencing reaction after each base incorporation ('wash-and-scan' cycle) and methods which do not need to halt between read steps. Examples of single molecule sequencing methods include single molecule real-time sequencing (Pacific Biosciences), nanopore-based sequencing (Oxford Nanopore), duplex interrupted nanopore sequencing, and direct imaging of DNA using advanced microscopy.

As used herein, "analyzing" the polypeptide means to identify, detect, quantify, characterize, distinguish, or a combination thereof, all or a portion of the components of the polypeptide. For example, analyzing a peptide, polypeptide, or protein includes determining all or a portion of the amino acid sequence (contiguous or non-continuous) of the peptide. Analyzing a polypeptide also includes partial identification of a component of the polypeptide. For example, partial identification of amino acids in the polypeptide protein sequence can identify an amino acid in the protein as belonging to a subset of possible amino acids. Analysis typically begins with analysis of the n NTAA, and then proceeds to the next amino acid of the peptide (i.e., n−1, n−2, n−3, and so forth). This is accomplished by elimination of the n NTAA, thereby converting the n−1 amino acid of the peptide to an N-terminal amino acid (referred to herein as the "n−1 NTAA"). Analyzing the peptide may also include determining the presence and frequency of post-translational modifications on the peptide, which may or may not include information regarding the sequential order of the post-translational modifications on the peptide. Analyzing the peptide may also include determining the presence and frequency of epitopes in the peptide, which may or may not include information regarding the sequential order or location of the epitopes within the peptide. Analyzing the peptide may include combining different types of analysis, for example obtaining epitope information, amino acid sequence information, post-translational modification information, or any combination thereof.

It is understood that aspects and embodiments of the invention described herein include "consisting of" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Other objects, advantages and features of the present invention will become apparent from the following specification taken in conjunction with the accompanying drawings.

I. SEQUENTIAL ENCODING

Provided herein are methods and kits for analysis of macromolecules, e.g., peptides, polypeptides, and proteins, which includes a step of transferring information to a recording tag. The analysis employs nucleic acid encoding of molecular recognition events. In some aspects, the information transferred comprises identifying information regarding a binding agent that is configured to bind to the macromolecule. The provided method for information transfer includes: (a) providing a macromolecule and an associated recording tag joined to a support; (b) contacting the macromolecule with a binding agent capable of binding to the macromolecule, wherein the binding agent comprises a coding tag with identifying information regarding the binding agent, to allow binding between the macromolecule and the binding agent; (c) joining the 5' end of the recording tag to the 3' end of the coding tag by a nucleic acid joining reagent; (d) extending the recording tag using the coding tag as a template by a polymerase, generating a double stranded extended recording tag; and (e) cleaving the double stranded extended recording tag with a double strand nucleic acid cleaving reagent to generate a 3' overhang in the extended recording tag. Performing these steps, information is transferred from the coding tag to the recording tag to generate an extended recording tag. In some embodiments, the polymerase, the nucleic acid joining reagent and the double strand nucleic acid cleaving reagent are provided in a mixture or at the same time. In some aspects, steps (c), (d), and (e) are performed as a one-pot reaction. In some other aspects, steps (c), (d), and (e) are performed sequentially and separately. In some cases, each reagent can be provided separately or two of the three enzymatic reagents are provided at the same time. In some cases, the recording tag and the coding tag of the provided methods comprise nucleic acids.

One or more cycles of steps (b) to (e) can be repeated to generate an extended recording tag that includes information transferred from a plurality of coding tags. For example, steps (b), (c), (d) and (e) can be repeated sequentially one or more times in a cyclic manner. In some embodiments, the extended recording tag generated comprises a nucleic acid hairpin. The methods provided herein may include providing a plurality of binding agents and a plurality of macromolecules and allowing the binding agents and macromolecules to interact. In some embodiments, a plurality of binding agents are provided in each cycle as a mixture. In some embodiments, the present methods comprise contacting a single macromolecule with a single binding agent, contacting a plurality of macromolecules with a single binding agent, or contacting a plurality of macromolecules with a plurality of binding agents.

In some embodiments, the present disclosure provides, in part, methods for analyzing a macromolecule which includes information transfer, with direct applications to protein and peptide characterization, quantitation, and/or sequencing. In some particular embodiments, the macromolecule for analysis is not a nucleic acid. In some particular embodiments, the binding agent is not a nucleic acid. Provided herein are methods for transferring information from a coding tag associated or joined to a binding agent to a recording tag associated with the macromolecule to be analyzed (e.g., polypeptide). Transfer of information is performed using a three-part reaction which includes ligation, extension, and cleavage by a double strand nucleic acid cleaving reagent (e.g., a restriction enzyme). The information transferred from the coding tag includes identifying information regarding the identity of the binding agent, thereby providing information regarding the macromolecule or portion thereof bound by the binding agent. For example, if a protein/polypeptide/peptide macromolecule is bound by the binding agent, the identifying information may comprise information regarding the identity of the one or more amino acid(s) bound by the binding agent. In some embodiments, the information regarding the identity of the macromolecule (or portion thereof) bound by the binding agent is from the coding tag associated with said binding agent, and transferred to the recording tag. The macromolecule analysis assay may include one or more cycles of transferring identifying information of a binding agent from a coding tag to a recording tag associated with the macromolecule to be analyzed. The final extended recording tag associated with the macromolecule for analysis can comprise information from one or more coding tags. If multiple cycles are performed, the resulting extended recording tag then contains information built up from a series of binding events and multiple information transfer events from coding tags. In general, improvements for the transfer of information using the described method involving the activities of the nucleic acid joining reagent, the polymerase, and the double strand nucleic acid cleaving reagent may provide certain benefits to the macromolecule analysis assay.

In some aspects, the sequential encoding system used in the provided method for analyzing macromolecules provides certain advantages to the overall design of the assay. In particular, some advantages are provided by the sequential steps carried out by the nucleic acid joining reagent, the polymerase, and the double strand nucleic acid cleaving reagent. In some embodiments, the methods include or use a reaction system wherein mixed enzymes are provided to the reaction, such that it is performed in one step and/or the reactions are carried out in a one-pot reaction. By design of the system, the ligation, extension, and cleavage of steps (c), (d), and (e), respectively, occurs in a step-wise or sequential manner. In some other embodiments, the step-wise nature of the steps could be introduced with the use of blocking groups or by introducing additional requirements such that the ligation, extension, and/or cleavage are performed in a manner that is conditional on the completion of a previous step. The activities of the polymerase, the nucleic acid joining reagent and the double strand nucleic acid cleaving reagent, are provided with suitable conditions, for transferring information from a coding tag to the recording tag to generate an extended recording tag. Some advantages using the described methods include high information transfer (encoding) success, simple design for a step-wise reaction, option to perform in a single step/as a single pot reaction, reducing the need for spacers or the length of the spacers, minimizing DNA-DNA interactions in the system, and/or minimizing DNA-protein interactions in the system. For example, compared to a single stranded nucleic acid molecule which may be flexible and provide exposed bases for interaction, the double stranded recording tag provided herein may exhibit fewer interactions for the DNA to interact with other components (e.g. nucleic acids, peptides, binding agents, etc.) in the system.

In some embodiments, the provided methods for transferring information using sequential encoding allow for certain benefits related to the format of the nucleic acid components used. For example, in an extension-based information transfer method that depends on a spacer element to form a polymerase priming site, the size of the spacer may be required to be a certain length, such as at least 6 base pairs. Shorter spacers may have advantages such as avoiding non-specific interactions in the assay. In some cases, sequence enrichment would be more straightforward if repetitive elements were minimized or eliminated. In some cases, the provided methods avoid certain issues with specificity, bias, stability, and efficiency when compared to an extension-based method. In ligation-based methods for information transfer, efficiency with joining suitable ends of the nucleic acids and complexity with other required steps for transferring information may be an issue. In some embodiments, the provided methods employing the polymerase, the nucleic acid joining reagent and the double strand nucleic acid cleaving reagent, provide benefits over systems that are solely extension-based or ligation-based. By employing the cleaving step which occurs after the polymerase step, A-tailing issues where polymerases leave an "A" overhang can be avoided. The use of double-stranded DNA minimizes possible DNA-DNA interactions that can occur in other systems utilizing single-stranded DNA components. In some cases, the shorter spacers that can be employed in the provided methods can be reduced in length, such as to 2 bp spacers, and in some cases, the use of spacers can be eliminated entirely. In some aspects, the sequential encoding method is self-terminating after one cycle of information transfer due to incompatible overhangs.

In some embodiments, both the recording tag and the coding tag include a spacer sequence. For example, the spacer is a nucleic acid molecule of less than or equal to 10 bases, less than or equal to 9 bases, less than or equal to 8 bases, less than or equal to 7 bases, less than or equal to 6 bases, less than or equal to 5 bases, less than or equal to 4 bases, less than or equal to 3 bases, or less than or equal to 2 bases. The spacer can be a cycle-specific spacer or cycle-alternating spacer. Particular designs of the system for transferring information can utilize spacer such that information is only transferred from a second coding tag to the extended recording tag if the spacer added by the previous coding tag matches at least a portion of the spacer of the second coding tag. In this manner, subsequent encoding events are dependent and conditional on previous encoding events. In some other embodiments, neither the recording tag nor the coding includes a spacer sequence.

In some embodiments, some steps in the cycle can be optionally repeated. For example, after one cycle of providing binding agents and transferring of information from coding tags, the binding agents can be removed, and the binding agents can be provided again to permit re-binding of the binding agent and allow another opportunity for information transfer to occur, e.g. in case wherein the first information transfer did not occur. In some aspects, the methods provided using alternating spacers are suited for this repeating to permit a second opportunity for information transfer. If the first binding and information transfer event was successful, the spacer transferred along with the successful coding tag information would not allow a repeated information transfer event to occur (even if the binding agent recognizes the macromolecule for analysis). In contrast, if a first information transfer event was unsuccessful, rebinding would bring in coding tag with a spacer that would match the spacer on the existing recording tag and the second binding would allow information transfer event to occur after the re-binding step, thereby providing a mechanism to make up for the first missed event.

The provided methods employ use of a polymerase, a nucleic acid joining reagent and a double strand nucleic acid cleaving reagent. Any suitable enzymes for extension, ligation, and cleavage of double stranded nucleic acids can be used (see e.g., Patent Publication No. CN104212791B, CN101560538A, and CN100510069C).

In the provided methods, the transfer of information from the coding tag to the recording tag begins with a ligation step. The 5' end of the recording tag is joined (e.g., ligated) to the 3' end of the coding tag by a nucleic acid joining reagent. In some embodiments, the binding agent does not remain bound or does not need to remain bound to the macromolecule after the recording tag is joined to the coding tag by the nucleic acid joining reagent.

In some examples, the nucleic acid joining reagent is a chemical ligation reagent or an enzymatic ligation reagent. The ligation step may be performed by chemical ligation or enzymatic ligation (e.g., a sticky end ligation, a single-strand (ss) ligation such as a ssDNA ligation, or any combination thereof). In some designs, the ligation may be a blunt end ligation and/or sticky end ligation. The provided sequential encoding method is designed to generate a double stranded structure that comprises information transferred from the coding tag, and any joining methods that accomplishes this purpose can be applied. Examples of ligases include, but are not limited to CV DNA ligase, CircLigase, CircLigase II, T4 DNA ligase, T7 DNA ligase, T3 DNA ligase, Taq DNA ligase, *E. coli* DNA ligase, 9° N DNA ligase (See e.g., U.S. Patent Publication No. US 2014/0378315 A1 or U.S. Pat. No. 10,494,671 B2). In some preferred embodiments, the nucleic acid joining reagent refers to an enzyme (e.g., ligase) that joins two DNA segment, such as a T4DNA ligase.

The joining or ligation step is followed by an extension step, which may include a polymerase-mediated reaction (e.g., primer extension of single-stranded nucleic acid or double-stranded nucleic acid). Extension of the 3' end of the recording tag (or already extended recording tag) occurs using the ligated coding tag as a template. With the extension step, the restriction enzyme/endonuclease sites introduced and ligated from the coding tag become double-strand on the extended recording tag. In some embodiments, a DNA polymerase that is used for primer extension possesses strand-displacement activity and has limited or is devoid of 3'-5 exonuclease activity. Several of many examples of such polymerases include Klenow exo-(Klenow fragment of DNA Pol 1), T4 DNA polymerase exo-, T7 DNA polymerase exo (Sequenase 2.0), Pfu exo-, Vent exo-, Deep Vent exo-, Bst DNA polymerase large fragment exo-, Bca Pol, 9° N Pol, and Phi29 Pol exo-. In a preferred embodiment, the DNA polymerase is active at room temperature and up to 45° C. In another embodiment, a "warm start" version of a thermophilic polymerase is employed such that the polymerase is activated and is used at about 40° C.-50° C. An exemplary warm start polymerase is Bst 2.0 Warm Start DNA Polymerase (New England Biolabs). Suitable conditions for the extension reaction may also be provided, including any additives and buffers for the reaction.

Figure 1B:
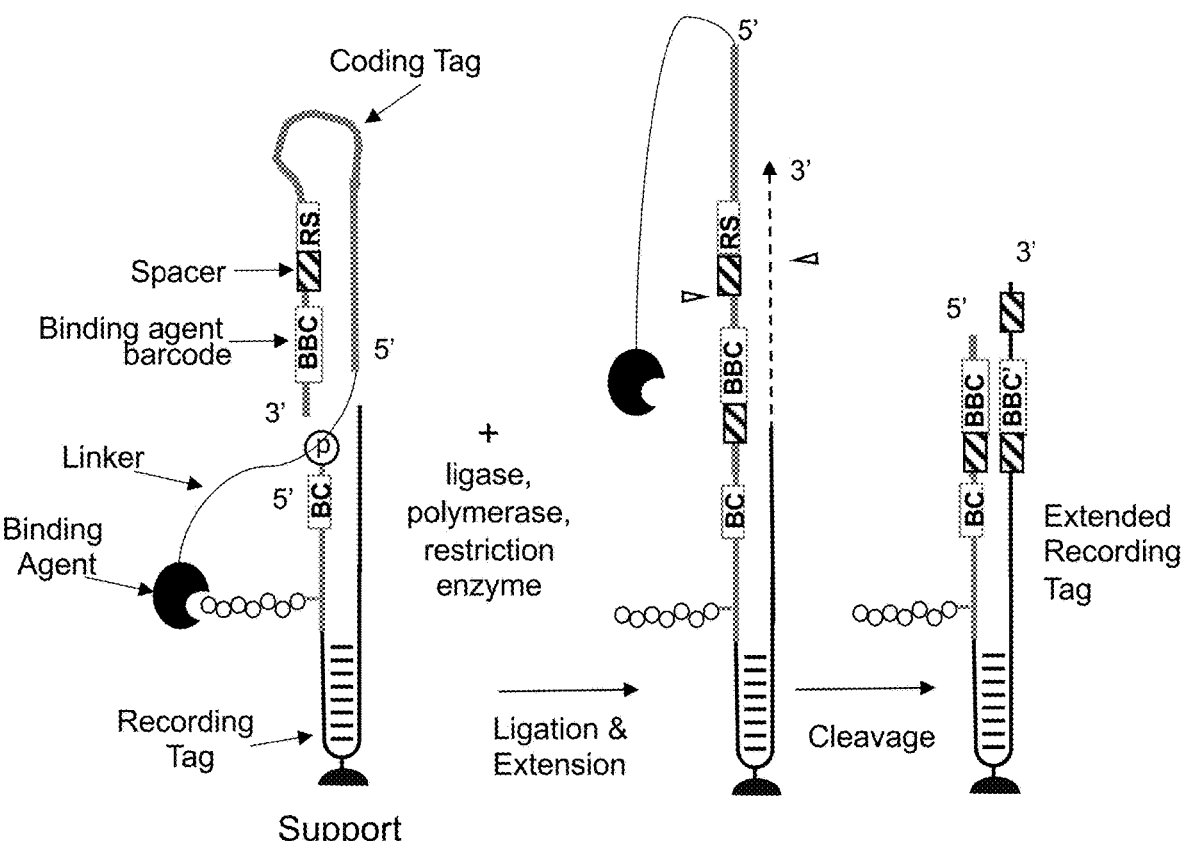

Following the extension step, a double stranded extended recording tag containing a recognition sequence capable of being recognized by a double strand nucleic acid cleaving reagent is generated. Cleaving the double stranded extended recording tag generates a 3' overhang on the recording tag. In some aspects, the 3' overhang of the extended recording tag generated by the double strand nucleic acid cleaving reagent is available to hybridize with a second coding tag when step (b) is repeated. In some aspects, cleaving the double stranded extended recording tag untethers or unlinks the binding agent from the extended recording tag. In some specific cases, cleaving the double stranded recording tag releases the binding agent from the extended recording tag. In some instances, the cleaving makes the binding agent releasable from the macromolecule being analyzed. The double strand nucleic acid cleaving reagent may be a restriction enzyme or restriction endonuclease. In some embodiments, the restriction enzyme is a type IIS restriction enzyme. The advantage of using a type IIS restriction enzyme includes that it can generate less single strand nucleotides left after the cleavage reaction in comparison to a classical palindromic restriction enzyme, as shown in FIG. 1B and Example 2 (only 2 nt spacer). In some preferred embodiments, the sequence after cleavage by the cleaving reagent leaves an 3' overhang. For example, the cleaving reagent may be the enzyme BtsI, Mva1269I, BsaI, BsmBI and others. The type IIS restriction enzyme may recognize a sequence of bases that comprises: 5' . . . GCAGTGNN . . . 3'/3' . . . CGTCACNN . . . 5'. In some particular instances, the restriction enzyme is Nb.BtsI or BtsI-v2 or a derivative thereof.

In some other embodiments, the double strand nucleic acid cleaving reagent is a type IIP restriction enzyme having palindromic specificity and cleaving within its recognition sequence. To avoid potential recreation of the restriction enzyme cutting site in the ligation site after ligation of the coding tag to the recording tag (see e.g., FIG. 1B, first step), the coding tag sequence adjacent to the ligation site should be different from the enzyme cutting site. In some preferred embodiments, a type IIP restriction enzyme generates a 3' overhang on the recording tag after cleavage, as shown in FIG. 1B. In some other embodiments, a type IIP restriction enzyme generating a blunt end can be adopted for use in the disclosed methods. In these embodiments, the 3' end of the coding tag should be ligated to the blunt end of the recording tag generated after restriction enzyme cleavage, and the coding tag sequence adjacent to the ligation site should be different from the restriction enzyme cutting site.

In some other embodiments, a combination of enzymes or endonucleases can be used to achieve cutting of both strands of the extended recording tag. For example, if a nicking enzyme or endonuclease is used to cut a first strand of the extended recoding tag, then a secondary mechanism can be employed to cut the second strand. In some specific embodiments, a nicking enzyme or a nicking endonuclease is not used. An appropriate restriction enzyme may be selected based on considerations for preferred cut sites, distance between digestion position and recognition position, precision of the digestion position, and ability to generate the needed nucleic acid end for other steps of the method.

In some embodiments, the nucleic acid joining reagent and the polymerase are provided simultaneously. In some embodiments, the polymerase and the double strand nucleic acid cleaving reagent are provided simultaneously.

In some of the provided embodiments, the steps (a), (b), (c), (d) and (e) are performed sequentially. In certain embodiments, the binding event information of the binding agent to the macromolecule (e.g., peptide) is transferred from the coding tag to the recording tag associated with the immobilized macromolecule in a cyclic fashion. In some embodiments, steps repeated one or more times include: (b) contacting the macromolecule with a binding agent capable of binding to the macromolecule, wherein the binding agent comprises a coding tag with identifying information regarding the binding agent, to allow binding between the macromolecule and the binding agent; (c) joining the 5' end of the recording tag to the 3'end of the coding tag by a nucleic acid joining reagent; (d) extending the recording tag using the coding tag as a template by a polymerase, generating a double stranded extended recording tag; and (e) cleaving the double stranded extended recording tag with a double strand nucleic acid cleaving reagent to generate a 3' overhang in the extended recording tag.

In some embodiments, the method further includes removing the binding agent. For example, the binding agent can be removed after transferring the information of the coding tag to the recording tag. Once a cycle of encoding is performed, the binding agent can be removed prior to repeating step (b). The binding agent may be removed or released by providing appropriate conditions (e.g., reagents and temperature) during a wash.

In some embodiments, the method further includes removing a portion of the macromolecule prior to repeating step (b). For example, if a polypeptide is being analyzed, the method can include removing one or more amino acids (e.g., from the terminus) of the polypeptide prior to repeating step (b). In some cases, the N-terminal amino acid (NTAA) polypeptide is removed from the polypeptide to expose a new NTAA of the polypeptide prior to repeating step (b). In some embodiments, the removed portion of the macromolecule is treated with or has been modified by a chemical agent or an enzymatic agent. In some cases, the polypeptide is treated with the reagent for modifying a terminal amino acid of the polypeptide. The modification of the polypeptide, such as the NTAA, can be performed prior to step (b). In some cases, the modification of the polypeptide, such as the NTAA, can be performed after step (e).

In some cases, the method further includes one or more wash steps before, between, or after any one or more of the steps. For example, after the binding agent is provided in step (b), a wash step may be performed before any of the enzymatic reagents (e.g., nucleic acid joining reagent, polymerase, double strand nucleic acid cleaving reagent) are introduced. Such a wash step may remove non-specifically bound binding agents. The stringency of the wash step may be tuned depending on the affinity of the binding agent. In some cases, it is preferable that no wash steps are required between steps (c), (d), and (e). In some other aspects, a wash step is performed after the ligation of step (c). After ligation and washing, the subsequent steps involving the polymerase and double strand nucleic acid cleaving reagent can be provided in one step. In some other aspects, a wash step is performed after the extension of step (d). In some cases, a wash step is performed before step (c), step (d), and/or step (e). After ligation and extension occur in one step, a wash step may be performed before the double strand nucleic acid cleaving reagent is provided. In some cases, the method further includes removing the binding agent after information is transferred to the recoding tag, such as after step (e) and/or before step (b) is repeated in a subsequent cycle.

In some embodiments, a final information transfer cycle is performed to provide a capping sequence to the extended recording tag, wherein optionally, the capping sequence comprises a universal priming site for amplification, sequencing, or both. The capping sequence may be provided to the extended recording tag by a binding agent that is configured to bind a universal feature of the macromolecules. In this manner, the binding agent for delivering a capping sequence is configured to bind to a target moiety contained by all or many macromolecules in the sample. In some examples, the universal feature is a chemical modification of the polypeptides. The capping sequence may include a sequence useful for analysis of the extended recording tag, such as a universal reverse priming site.

A. Recording Tag

The macromolecule (e.g., protein or polypeptide) for analysis may be labeled with a recording tag comprising nucleic acid molecule or an oligonucleotide. In some aspects, a plurality of macromolecules in the sample is provided with recording tags. The recording tags may be associated or attached, directly or indirectly to the macromolecules using any suitable means. In some embodiments, a macromolecule may be associated with one or more recording tags. In some aspects, the recording tags may be associated or attached, directly or indirectly to the macromolecules prior to contacting with a binding agent.

In some embodiments, at least one recording tag is associated or co-localized directly or indirectly with the macromolecule (e.g., polypeptide). Providing a macromolecule and an associated recording tag in step (a) may include treating the recording tag and any associated nucleic acids to join, cleave, or otherwise prepare the recording tag for the assay. In some embodiments, step (a) includes using ligation and/or extension to provide the barcode and/or the UMI to the recording tag. In some aspects, step (a) includes cleaving the recording tag using a restriction enzyme to generate a 3' overhang. For example, the 3' overhang of the recording tag is generated by extension using a polymerase and/or cleavage by a double strand nucleic acid cleaving reagent. An exemplary workflow for preparing and providing the recording tag is shown in FIG. 1A.

In a particular embodiment, a single recording tag is attached to a polypeptide, such as via the attachment to a N- or C-terminal amino acid. In another embodiment, multiple recording tags are attached to the polypeptide, such as to the lysine residues or peptide backbone. In some embodiments, a polypeptide labeled with multiple recording tags is fragmented or digested into smaller peptides, with each peptide labeled on average with one recording tag.

A recording tag may comprise DNA, RNA, or polynucleotide analogs including PNA, gPNA, GNA, HNA, BNA, XNA, TNA, or a combination thereof. A recording tag may be single stranded, or partially or completely double stranded. In some particular embodiments, certain advantages accompany a recording tag which comprises a double stranded region. For example, an advantage may be reduced DNA-DNA interactions with other nucleic acid components of the system. In some cases, the recording tag includes a nucleic acid hairpin. A recording tag may have a blunt end or overhanging end. In some particular embodiments, the recording tag associated with the macromolecule is processed or treated (e.g., via digestion) such that it has a 3' overhang. In certain embodiments, all or a substantial amount of the macromolecules (e.g., at least 50%, 55%, 60%, 65%, 70%, 75%, 80%, 85%, 90%, 95%, 96%, 97%, 98%, 99%, or 100%) within a sample are labeled with a recording tag. In other embodiments, a subset of macromolecules within a sample are labeled with recording tags. In a particular embodiment, a subset of macromolecules from a sample undergo targeted (analyte specific) labeling with recording tags. For example, targeted recording tag labeling of proteins may be achieved using target protein-specific binding agents (e.g., antibodies, aptamers, etc.). In some embodiments, the recording tags (or a portion thereof) are attached to the macromolecules prior to providing the sample on a support. In some embodiments, the recording tags are attached to the macromolecules after providing the sample on the support.

In some embodiments, the recording tag may comprise other nucleic acid components. In some embodiments, the recording tag may comprise a unique molecular identifier, a compartment tag, a partition barcode, sample barcode, a fraction barcode, a spacer sequence, a universal priming site, or any combination thereof. In some embodiments, the recording tag may comprise a blocking group, such as at the 3'-terminus of the recording tag. In some cases, the 3'-terminus of the recording tag is blocked to prevent extension of the recording tag by a polymerase.

In some embodiments, the recording tag can include a sample identifying barcode. A sample barcode is useful in the multiplexed analysis of a set of samples in a single reaction vessel or immobilized to a single solid substrate or collection of solid substrates (e.g., a planar slide, population of beads contained in a single tube or vessel, etc.). For example, macromolecules from many different samples can be labeled with recording tags with sample-specific barcodes, and then all the samples pooled together prior to immobilization to a support, cyclic binding of the binding agent, and recording tag analysis. Alternatively, the samples can be kept separate until after creation of a DNA-encoded library, and sample barcodes attached during PCR amplification of the DNA-encoded library, and then mixed together prior to sequencing. This approach could be useful when assaying analytes (e.g., proteins) of different abundance classes.

In certain embodiments, a recording tag comprises an optional, unique molecular identifier (UMI), which provides a unique identifier tag for each macromolecules (e.g., polypeptide) to which the UMI is associated with. A UMI can be about 3 to about 40 bases, about 3 to about 30 bases, about 3 to about 20 bases, or about 3 to about 10 bases, or about 3 to about 8 bases. In some embodiments, a UMI is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, or 40 bases in length. A UMI can be used to de-convolute sequencing data from a plurality of extended recording tags to identify sequence reads from individual macromolecules. In some embodiments, within a library of macromolecules, each macromolecule is associated with a single recording tag, with each recording tag comprising a unique UMI. In other embodiments, multiple copies of a recording tag are associated with a single macromolecule, with each copy of the recording tag comprising the same UMI. In some embodiments, a UMI has a different base sequence than the spacer or coding tags to facilitate distinguishing these components during sequence analysis. In some embodiments, the UMI may provide function as a location identifier and also provide information in the macromolecule analysis assay. For example, the UMI may be used to identify molecules that are identical by descent, and therefore originated from the same initial molecule. In some aspects, this information can be used to correct for variations in amplification, and to detect and correct sequencing errors during analysis.

In some embodiments, the recording tag comprises a spacer polymer. In certain embodiments, a recording tag comprises a spacer at its terminus, e.g., 3' end. As used herein reference to a spacer sequence in the context of a recording tag includes a spacer sequence that is identical to the spacer sequence associated with its cognate binding agent, or a spacer sequence that is complementary to the spacer sequence associated with its cognate binding agent. The terminal, e.g., 3', spacer on the recording tag permits transfer of identifying information of a cognate binding agent from a coding tag to the recording tag during the first binding cycle (e.g., via annealing of complementary spacer sequences for primer extension or sticky end ligation). In one embodiment, the spacer sequence is about 1-20 bases in length, about 2-12 bases in length, or 5-10 bases in length. In some instances, the spacer sequence is about 2-5 bases in length. The length of the spacer may depend on factors such as the temperature and reaction conditions for transferring coding tag information to the recording tag.

In some embodiments using spacer sequences, the recording tags associated with a library of polypeptides share a common spacer sequence. In other embodiments, the recording tags associated with a library of polypeptides have binding cycle specific spacer sequences that are complementary to the binding cycle specific spacer sequences of adaptor molecules. In some aspects, the spacer sequence in the recording tag is designed to have minimal complementarity to other regions in the recording tag. In some cases, the spacer sequence of the recording tags should have minimal sequence complementarity to components such unique molecular identifiers, barcodes (e.g., compartment, partition, sample, spatial location), universal primer sequences, coding tag sequences, cycle specific sequences, etc. present in the recording or coding tags. In some embodiments, the spacer is designed based on the double strand nucleic acid cleaving reagent (e.g., restriction enzyme) selected for use.

In certain embodiments, a recording tag comprises a universal priming site, e.g., a forward or 5' universal priming site. A universal priming site is a nucleic acid sequence that may be used for priming a library amplification reaction and/or for sequencing. A universal priming site may include, but is not limited to, a priming site for PCR amplification, flow cell adaptor sequences that anneal to complementary oligonucleotides on flow cell surfaces (e.g., Illumina next generation sequencing), a sequencing priming site, or a combination thereof. A universal priming site can be about 10 bases to about 60 bases. In some embodiments, a universal priming site comprises an Illumina P5 primer (AAT- GATACGGCGACCACCGA; SEQ ID NO: 1) or an Illumina P7 primer (CAAGCAGAAGACGGCATACGAGAT; SEQ ID NO: 2).

In certain embodiments, a recording tag comprises a compartment tag. In some embodiments, the compartment tag is a component within a recording tag. In some embodiments, the recording tag can also include a barcode which represents a compartment tag in which a compartment, such as a droplet, microwell, physical region on a support, etc. is assigned a unique barcode. The association of a compartment with a specific barcode can be achieved in any number of ways such as by encapsulating a single barcoded bead in a compartment, e.g., by direct merging or adding a barcoded droplet to a compartment, by directly printing or injecting a barcode reagents to a compartment, etc. The barcode reagents within a compartment are used to add compartment-specific barcodes to the macromolecule or fragments thereof within the compartment. Applied to protein partitioning into compartments, the barcodes can be used to map analyzed peptides back to their originating protein molecules in the compartment. This can greatly facilitate protein identification. Compartment barcodes can also be used to identify protein complexes. In other embodiments, multiple compartments that represent a subset of a population of compartments may be assigned a unique barcode representing the subset. In some embodiments, the recording tag comprises fraction barcode which contains identifying information for the macromolecules within a fraction.

In some embodiments, one or more of the tags (e.g., compartment tag, a partition barcode, sample barcode, a fraction barcode, etc.) further comprise a functional moiety capable of reacting with an internal amino acid, the peptide backbone, or N-terminal amino acid on the plurality of protein complexes, proteins, or polypeptides. In some embodiments, the functional moiety is a click chemistry moiety, an aldehyde, an azide/alkyne, or a maleimide/thiol, or an epoxide/nucleophile, an inverse electron demand Diels-Alder (iEDDA) group, or a moiety for a Staudinger reaction. In some specific embodiments, a plurality of compartment tags is formed by printing, spotting, ink-jetting the compartment tags into the compartment, or a combination thereof. In some embodiments, the tag is attached to a polypeptide to link the tag to the macromolecule via a polypeptide-polypeptide linkage. In some embodiments, the tag-attached polypeptide comprises a protein ligase recognition sequence.

In certain embodiments, a peptide or polypeptide macromolecule can be immobilized to a support by an affinity capture reagent (and optionally covalently crosslinked), wherein the recording tag is associated with the affinity capture reagent directly, or alternatively, the macromolecule can be directly immobilized to the support with a recording tag.

In some embodiments, the macromolecule is attached to a bait nucleic acid to form a nucleic acid-macromolecule chimera. The immobilization methods may comprise bringing the nucleic acid-macromolecule chimera into proximity with a support by hybridizing the bait nucleic acid to a capture nucleic acid attached to the support, and covalently coupling the nucleic acid-macromolecule chimera to the solid support. In some cases, the nucleic acid-macromolecule chimera is coupled indirectly to the solid support, such as via a linker. In some embodiments, a plurality of the nucleic acid-macromolecule chimeras is coupled on the solid support and any adjacently coupled nucleic acid-macromolecule chimeras are spaced apart from each other at an average distance of about 50 nm or greater. The bait nucleic acid in some cases includes a universal priming site or a portion thereof.

As shown in an exemplary format in FIG. 1A, a peptide to be analyzed is attached to a bait nucleic acid which hybridizes to a capture nucleic acid hairpin immobilized on a support. The bait nucleic acid is ligated to the capture nucleic acid which comprises a reactive coupling moiety for attaching to the support. In some examples, the bait or capture nucleic acid, or the joined bait and capture nucleic acid may serve as a recording tag to which information regarding the polypeptide can be transferred from a coding tag.

FIG. 1A shows exemplary steps for preparing the recording tag which uses a capture nucleic acid that comprises or is a nucleic acid hairpin with a recessed 5' phosphorylated end. In the second panel of FIG. 1A, the bait nucleic acid with the attached peptide hybridizes with and is ligated to the capture nucleic acid hairpin. The bait nucleic acid may comprise one or more barcodes as shown and can also contain a restriction enzyme site (or a partial restriction enzyme site). In the third panel of FIG. 1A, a polymerase reaction is used to extend 3' end of the capture nucleic acid hairpin, generating a double stranded recording tag construct with the peptide attached. Once extension occurs using the bait nucleic acid as a template, the digestion site is double stranded and able to be recognized by a type IIS restriction enzyme for cleavage, and cleavage produces a recording tag with a 3' overhang (2-base pair sequence) with a recessed 5' phosphorylated end. This recording tag containing one or more barcodes is available for information transfer from a coding tag. In some embodiments, the preparation of the macromolecule for analysis with a recording tag and immobilization on a support can be performed using any of the methods as described in International Patent Application No. PCT/US2020/27840. The preparation and/or immobilization of the macromolecules can be performed prior to the information transfer steps and/or separately from the information transfer steps.

In some embodiments, the density or number of macromolecules provided with a recording tag is controlled or titrated. In some examples, the desired spacing, density, and/or amount of recording tags in the sample may be titrated by providing a diluted or controlled number of recording tags. In some examples, the desired spacing, density, and/or amount of recording tags may be achieved by spiking a competitor or "dummy" competitor molecule when providing, associating, and/or attaching the recording tags. In some cases, the "dummy" competitor molecule reacts in the same way as a recording tag being associated or attached to a macromolecule in the sample but the competitor molecule does not function as a recording tag. In some specific examples, if a desired density is 1 functional recording tag per 1,000 available sites for attachment in the sample, then spiking in 1 functional recording tag for every 1,000 "dummy" competitor molecules is used to achieve the desired spacing. In some examples, the ratio of functional recording tags is adjusted based on the reaction rate of the functional recording tags compared to the reaction rate of the competitor molecules.

In some examples, the labeling of the macromolecule with a recording tag is performed using standard amine coupling chemistries. For example, the e-amino group (e.g., of lysine residues) and the N-terminal amino group may be susceptible to labeling with amine-reactive coupling agents, depending on the pH of the reaction (Mendoza et al., Mass Spectrom Rev (2009) 28(5): 785-815). In a particular embodiment, the recording tag comprises a reactive moiety (e.g., for conjugation to a solid surface, a multifunctional linker, or a macromolecule), a linker, a universal priming sequence, a barcode (e.g., compartment tag, partition barcode, sample barcode, fraction barcode, or any combination thereof), an optional UMI, and a spacer (Sp) sequence for facilitating information transfer. In another embodiment, the protein can be first labeled with a universal DNA tag, and the barcode-Sp sequence (representing a sample, a compartment, a physical location on a slide, etc.) are attached to the protein later through and enzymatic or chemical coupling step. A universal DNA tag comprises a short sequence of nucleotides that are used to label a protein or polypeptide macromolecule and can be used as point of attachment for a barcode (e.g., compartment tag, recording tag, etc.). For example, a recording tag may comprise at its terminus a sequence complementary to the universal DNA tag. In certain embodiments, a universal DNA tag is a universal priming sequence. Upon hybridization of the universal DNA tags on the labeled protein to complementary sequence in recording tags (e.g., bound to beads), the annealed universal DNA tag may be extended via primer extension, transferring the recording tag information to the DNA tagged protein. In a particular embodiment, the protein is labeled with a universal DNA tag prior to proteinase digestion into peptides. The universal DNA tags on the labeled peptides from the digest can then be converted into an informative and effective recording tag.

The recording tags may comprise a reactive moiety for a cognate reactive moiety present on the macromolecule, e.g., protein, (e.g., click chemistry labeling, photoaffinity labeling). For example, recording tags may comprise an azide moiety for interacting with alkyne-derivatized proteins, or recording tags may comprise a benzophenone for interacting with native proteins, etc. Upon binding of the target protein by the target protein specific binding agent, the recording tag and target protein are coupled via their corresponding reactive moieties. After the target protein is labeled with the recording tag, the target-protein specific binding agent may be removed by digestion of the DNA capture probe linked to the target-protein specific binding agent. For example, the DNA capture probe may be designed to contain uracil bases, which are then targeted for digestion with a uracil-specific excision reagent (e.g., USER™), and the target-protein specific binding agent may be dissociated from the target protein. In some embodiments, other types of linkages besides hybridization can be used to link the recording tag to a macromolecule. A suitable linker can be attached to various positions of the recording tag, such as the 3' end, at an internal position, or within the linker attached to the 5' end of the recording tag.

The information from one or more coding tags is transferred to the recording tag to generate an extended recording tag. In some embodiments, an extended recording tag comprises a universal forward (or 5') priming sequence, information transferred from one or more coding tag(s), and a spacer sequence. In some embodiments, an extended recording tag comprises a universal forward (or 5') priming sequence, any optional barcodes and/or UMI (e.g., sample barcode, partition barcode, compartment barcode, or any combination thereof), information transferred from one or more coding tag(s), a spacer sequence, and a universal reverse (or 3') priming sequence.

B. Binding Agent

The methods described herein use a binding agent configured for interacting with the macromolecules to be analyzed (e.g., polypeptides, peptides, proteins). The assay can include contacting a plurality of binding agents to a plurality of macromolecules. In some embodiments, the present methods comprise contacting a single macromolecule with a single binding agent, contacting a plurality of macromolecules with a single binding agent, or contacting a plurality of macromolecules with a plurality of binding agents. In some embodiments, the plurality of binding agents includes a mixture of binding agents configured to bind different target moieties.

A binding agent can be any molecule (e.g., peptide, polypeptide, protein, nucleic acid, carbohydrate, small molecule, and the like) capable of binding to a component or feature of a polypeptide. A binding agent can be a naturally occurring, synthetically produced, or recombinantly expressed molecule. In some embodiments, the scaffold used to engineer a binding agent can be from any species, e.g., human, non-human, transgenic. A binding agent may bind to a portion of a target macromolecule or a motif. A binding agent may bind to a single monomer or subunit of a polypeptide (e.g., a single amino acid) or bind to multiple linked subunits of a polypeptide (e.g., dipeptide, tripeptide, or higher order peptide of a longer polypeptide molecule).

In some examples, the binding agent comprises an antibody, an antigen-binding antibody fragment, a single-domain antibody (sdAb), a recombinant heavy-chain-only antibody (VHH), a single-chain antibody (scFv), a shark-derived variable domain (vNARs), a Fv, a Fab, a Fab', a F(ab')2, a linear antibody, a diabody, an aptamer, a peptide mimetic molecule, a fusion protein, a reactive or non-reactive small molecule, or a synthetic molecule.

In certain embodiments, a binding agent may be designed to bind covalently. Covalent binding can be designed to be conditional or favored upon binding to the correct moiety. For example, an target and its cognate binding agent may each be modified with a reactive group such that once the target-specific binding agent is bound to the target, a coupling reaction is carried out to create a covalent linkage between the two. Non-specific binding of the binding agent to other locations that lack the cognate reactive group would not result in covalent attachment. In some embodiments, the target comprises a ligand that is capable of forming a covalent bond to a binding agent. In some embodiments, the target comprises a ligand group that is capable of covalent binding to a binding agent. Covalent binding between a binding agent and its target may allow for more stringent washing to be used to remove binding agents that are non-specifically bound, thus increasing the specificity of the assay. In some embodiments, the method includes a wash step after contacting the binding agent to the macromolecule to remove non-specifically bound binding agents. The stringency of the wash step may be tuned depending on the affinity of the binding agent to the target and/or the strength and stability of the complex formed.

In some embodiments, the binding agents are configured to provide specificity for binding of the binding agent to the macromolecule. In certain embodiments, a binding agent may be a selective binding agent. As used herein, selective binding refers to the ability of the binding agent to preferentially bind to a specific ligand (e.g., amino acid or class of amino acids) relative to binding to a different ligand (e.g., amino acid or class of amino acids). Selectivity is commonly referred to as the equilibrium constant for the reaction of displacement of one ligand by another ligand in a complex with a binding agent. Typically, such selectivity is associated with the spatial geometry of the ligand and/or the manner and degree by which the ligand binds to a binding agent, such as by hydrogen bonding, hydrophobic binding, and Van der Waals forces (non-covalent interactions) or by reversible or non-reversible covalent attachment to the binding agent. It should also be understood that selectivity may be relative, and as opposed to absolute, and that different factors can affect the same, including ligand concentration. Thus, in one example, a binding agent selectively binds one of the twenty standard amino acids. In some examples, a binding agent binds to an N-terminal amino acid residue, a C-terminal amino acid residue, or an internal amino acid residue.

In some embodiments, the binding agent is partially specific or selective. In some aspects, the binding agent preferentially binds one or more amino acids. In some examples, a binding agent may bind to or is capable of binding to two or more of the twenty standard amino acids. For example, a binding agent may preferentially bind the amino acids A, C, and G over other amino acids. In some other examples, the binding agent may selectively or specifically bind more than one amino acid. In some aspects, the binding agent may also have a preference for one or more amino acids at the second, third, fourth, fifth, etc. positions from the terminal amino acid. In some cases, the binding agent preferentially binds to a specific terminal amino acid and a penultimate amino acid. For example, a binding agent may preferentially bind AA, AC, and AG or a binding agent may preferentially bind AA, CA, and GA. In some embodiments, a binding agent may exhibit flexibility and variability in target binding preference in some or all of the positions of the targets. In some examples, a binding agent may have a preference for one or more specific target terminal amino acids and have a flexible preference for a target at the penultimate position. In some other examples, a binding agent may have a preference for one or more specific target amino acids in the penultimate amino acid position and have a flexible preference for a target at the terminal amino acid position. In some embodiments, a binding agent is selective for a target comprising a terminal amino acid and other components of a macromolecule. In some examples, a binding agent is selective for a target comprising a terminal amino acid and at least a portion of the peptide backbone. In some particular examples, a binding agent is selective for a target comprising a terminal amino acid and an amide peptide backbone. In some cases, the peptide backbone comprises a natural peptide backbone or a post-translational modification. In some embodiments, the binding agent exhibits allosteric binding.

In some embodiments, the method comprises contacting a mixture of binding agents with a mixture of macromolecules and selectivity need only be relative to the other binding agents to which the target is exposed. It should also be understood that selectivity of a binding agent need not be absolute to a specific molecule but could be to a portion of a molecule. In some examples, selectivity of a binding agent need not be absolute to a specific amino acid, but could be selective to a class of amino acids, such as amino acids with polar or non-polar side chains, or with electrically (positively or negatively) charged side chains, or with aromatic side chains, or some specific class or size of side chains, and the like. In some embodiments, the ability of a binding agent to selectively bind a feature or component of a macromolecule is characterized by comparing binding abilities of binding agents. For example, the binding ability of a binding agent to the target can be compared to the binding ability of a binding agent which binds to a different target, for example, comparing a binding agent selective for a class of amino acids to a binding agent selective for a different class of amino acids. In some examples, a binding agent selective for non-polar side chains is compared to a binding agent selective for polar side chains. In some embodiments, a binding agent selective for a feature, component of a peptide, or one or more amino acid exhibits at least 1x, at least 2x, at least 5x, at least 10x, at least 50x, at least 100x, or at least 500x more binding compared to a binding agent selective for a different feature, component of a peptide, or one or more amino acid.

In a particular embodiment, the binding agent has a high affinity and high selectivity for the macromolecule, e.g., the polypeptide, of interest. In particular, a high binding affinity with a low off-rate may be efficacious for hybridization of the adaptor molecule to the coding tag. In certain embodiments, a binding agent has a Kd of about <500 nM, <200 nM, <100 nM, <50 nM, <10 nM, <5 nM, <1 nM, <0.5 nM, or <0.1 nM. In a particular embodiment, the binding agent is added to the polypeptide at a concentration >1x, >5x, >10x, >100x, or >1000x its Kd to drive binding to completion. For example, binding kinetics of an antibody to a single protein molecule is described in Chang et al., J Immunol Methods (2012) 378(1-2): 102-115.

In certain embodiments, a binding agent may bind to a terminal amino acid of a peptide, an intervening amino acid, dipeptide (sequence of two amino acids), tripeptide (sequence of three amino acids), or higher order peptide of a peptide molecule. In some embodiments, each binding agent in a library of binding agents selectively binds to a particular amino acid, for example one of the twenty standard naturally occurring amino acids. The standard, naturally-occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). In some embodiments, the binding agent binds to an unmodified or native (e.g., natural) amino acid. In some examples, the binding agent binds to an unmodified or native dipeptide (sequence of two amino acids), tripeptide (sequence of three amino acids), or higher order peptide of a peptide molecule. A binding agent may be engineered for high affinity for a native or unmodified N-terminal amino acid (NTAA), high specificity for a native or unmodified NTAA, or both. In some embodiments, binding agents can be developed through directed evolution of promising affinity scaffolds using phage display.

In certain embodiments, a binding agent may bind to a post-translational modification of an amino acid. In some embodiments, a peptide comprises one or more post-translational modifications, which may be the same of different. The NTAA, CTAA, an intervening amino acid, or a combination thereof of a peptide may be post-translationally modified. Post-translational modifications to amino acids include acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation, glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation (see, also, Seo and Lee, 2004, J. Biochem. Mol. Biol. 37:35-44).

In certain embodiments, a lectin is used as a binding agent for detecting the glycosylation state of a protein, polypeptide, or peptide. Lectins are carbohydrate-binding proteins that can selectively recognize glycan epitopes of free carbohydrates or glycoproteins. A list of lectins recognizing various glycosylation states (e.g., core-fucose, sialic acids, N-acetyl-D-lactosamine, mannose, N-acetyl-glucosamine) include: A, AAA, AAL, ABA, ACA, ACG, ACL, AOL, ASA, BanLec, BC2L-A, BC2LCN, BPA, BPL, Calsepa, CGL2, CNL, Con, ConA, DBA, Discoidin, DSA, ECA, EEL, F17AG, Gal1, Gal1-S, Gal2, Gal3, Gal3C-S, Gal7-S, Gal9, GNA, GRFT, GS-I, GS-II, GSL-I, GSL-II, HHL, HIHA, HPA, I, II, Jacalin, LBA, LCA, LEA, LEL, Lentil, Lotus, LSL-N, LTL, MAA, MAH, MAL_I, Malectin, MOA, MPA, MPL, NPA, Orysata, PA-IIL, PA-IL, PALa, PHA-E, PHA-L, PHA-P, PHAE, PHAL, PNA, PPL, PSA, PSL1a, PTL, PTL-I, PWM, RCA120, RS-Fuc, SAMB, SBA, SJA, SNA, SNA-I, SNA-II, SSA, STL, TJA-I, TJA-II, TxLCI, UDA, UEA-I, UEA-II, VFA, VVA, WFA, WGA (see, Zhang et al., 2016, MABS 8:524-535).

In some embodiments, a binding agent may bind to a native or unmodified or unlabeled or native terminal amino acid. In some examples, the binding agent binds to an unmodified or native dipeptide (sequence of two amino acids), tripeptide (sequence of three amino acids), or higher order peptide of a peptide molecule. A binding agent may be engineered for high affinity for a modified NTAA, high specificity for a modified NTAA, or both. In some embodiments, binding agents can be developed through directed evolution of promising affinity scaffolds using phage display.

Directed evolution of protein/enzyme scaffolds can be used to generate higher affinity, higher specificity binding agents that recognized the N-terminal amino acids in the context of an N-terminal label. In an example, Havranak et al. (U.S. Patent Publication No. US 2014/0273004) describes engineering aminoacyl tRNA synthetases (aaRSs) as specific NTAA binders. The amino acid binding pocket of the aaRSs has an intrinsic ability to bind cognate amino acids, but generally exhibits poor binding affinity and specificity. Moreover, these natural amino acid binders don't recognize N-terminal labels. Directed evolution of aaRS scaffolds can be used to generate higher affinity, higher specificity binding agents that recognized the N-terminal amino acids in the context of an N-terminal label.

In certain embodiments, a binding agent may bind to a modified or labeled terminal amino acid (e.g., an NTAA that has been functionalized or modified). In some embodiments, a binding agent may bind to a chemically or enzymatically modified terminal amino acid. A modified or labeled NTAA can be one that is functionalized with phenylisothiocyanate, PITC, 1-fluoro-2,4-dinitrobenzene (Sanger's reagent, DNFB), benzyloxycarbonyl chloride or carbobenzoxy chloride (Cbz-Cl), N-(Benzyloxycarbonyloxy)succinimide (Cbz-OSu or Cbz-O-NHS), dansyl chloride (DNS-Cl, or 1-dimethylaminonaphthalene-5-sulfonyl chloride), 4-sulfonyl-2-nitrofluorobenzene (SNFB), N-Acetyl-Isatoic Anhydride, Isatoic Anhydride, 2-Pyridinecarboxaldehyde, 2-Formylphenylboronic acid, 2-Acetylphenylboronic acid, 1-Fluoro-2,4-dinitrobenzene, Succinic anhydride, 4-Chloro-7-nitrobenzofurazan, Pentafluorophenylisothiocyanate, 4-(Trifluoromethoxy)-phenylisothiocyanate, 4-(Trifluoromethyl)-phenylisothiocyanate, 3-(Carboxylic acid)-phenylisothiocyanate, 3-(Trifluoromethyl)-phenylisothiocyanate, 1-Naphthylisothiocyanate, N-nitroimidazole-1-carboximidamide, N,N,Ä≤-Bis(pivaloyl)-1H-pyrazole-1-carboxamidine, N,N,Ä≤-Bis(benzyloxycarbonyl)-1H-pyrazole-1-carboxamidine, an acetylating reagent, a guanidinylation reagent, a thioacylation reagent, a thioacetylation reagent, or a thiobenzylation reagent, or a diheterocyclic methanimine reagent. In some examples, the binding agent binds an amino acid labeled by contacting with a reagent or using a method as described in International Patent Publication No. WO 2019/089846. In some cases, the binding agent binds an amino acid labeled by an amine modifying reagent.

A binding agent may bind to an N-terminal peptide, a C-terminal peptide, or an intervening peptide of a peptide, polypeptide, or protein molecule. A binding agent may bind to an N-terminal amino acid, C-terminal amino acid, or an intervening amino acid of a peptide molecule. A binding agent may bind to an N-terminal or C-terminal diamino acid moiety. An N-terminal diamino acid is comprised of the N-terminal amino acid and the penultimate N-terminal amino acid. A C-terminal diamino acid is similarly defined for the C-terminus. In some embodiments, the binding agent binds to a chemically modified N-terminal amino acid residue or a chemically modified C-terminal amino acid residue. To increase the affinity of a binding agent to small N-terminal amino acids (NTAAs) of peptides, the NTAA may be modified with an "immunogenic" hapten, such as dinitrophenol (DNP). This can be implemented in a cyclic sequencing approach using Sanger's reagent, dinitrofluorobenzene (DNFB), which attaches a DNP group to the amine group of the NTAA. Commercial anti-DNP antibodies have affinities in the low nM range (~8 nM, LO-DNP-2) (Bilgicer et al., J Am Chem Soc (2009) 131(26): 9361-9367); as such it stands to reason that it should be possible to engineer high-affinity NTAA binding agents to a number of NTAAs modified with DNP (via DNFB) and simultaneously achieve good binding selectivity for a particular NTAA. In another example, an NTAA may be modified with sulfonyl nitrophenol (SNP) using 4-sulfonyl-2-nitrofluorobenzene (SNFB). Similar affinity enhancements may also be achieved with alternative NTAA modifiers, such as an acetyl group or an amidinyl (guanidinyl) group.

In certain embodiments, a binding agent can be an aptamer (e.g., peptide aptamer, DNA aptamer, or RNA aptamer), a peptoid, an antibody or a specific binding fragment thereof, an amino acid binding protein or enzyme, an antibody binding fragment, an antibody mimetic, a peptide, a peptidomimetic, a protein, or a polynucleotide (e.g., DNA, RNA, peptide nucleic acid (PNA), a gPNA, bridged nucleic acid (BNA), xeno nucleic acid (XNA), glycerol nucleic acid (GNA), or threose nucleic acid (TNA), or a variant thereof).

As used herein, the terms antibody and antibodies are used in a broad sense, to include not only intact antibody molecules, for example but not limited to immunoglobulin A, immunoglobulin G, immunoglobulin D, immunoglobulin E, and immunoglobulin M, but also any immunoreactive component(s) of an antibody molecule or portion thereof that immuno-specifically bind to at least one epitope. An antibody may be naturally occurring, synthetically produced, or recombinantly expressed. An antibody may be a fusion protein. An antibody may be an antibody mimetic. Examples of antibodies include but are not limited to, Fab fragments, Fab' fragments, F(ab), fragments, single chain antibody fragments (scFv), miniantibodies, nanobodies, diabodies, crosslinked antibody fragments, Affibody™, nanobodies, single domain antibodies, DVD-Ig molecules, alphabodies, affimers, affitins, cyclotides, molecules, and the like. Immunoreactive products derived using antibody engineering or protein engineering techniques are also expressly within the meaning of the term antibodies. Detailed descriptions of antibody and/or protein engineering, including relevant protocols, can be found in, among other places, J. Maynard and G. Georgiou, 2000, Ann. Rev. Biomed. Eng. 2:339-76; Antibody Engineering, R. Kontermann and S. Dubel, eds., Springer Lab Manual, Springer Verlag (2001); U.S. Pat. No. 5,831,012; and S. Paul, Antibody Engineering Protocols, Humana Press (1995).

As with antibodies, nucleic acid and peptide aptamers that specifically recognize a macromolecule, e.g., a peptide or a polypeptide, can be produced using known methods. Aptamers bind target molecules in a highly specific, conformation-dependent manner, typically with very high affinity, although aptamers with lower binding affinity can be selected if desired. Aptamers have been shown to distinguish between targets based on very small structural differences such as the presence or absence of a methyl or hydroxyl group and certain aptamers can distinguish between D- and L-enantiomers. Aptamers have been obtained that bind small molecular targets, including drugs, metal ions, and organic dyes, peptides, biotin, and proteins, including but not limited to streptavidin, VEGF, and viral proteins. Aptamers have been shown to retain functional activity after biotinylation, fluorescein labeling, and when attached to glass surfaces and microspheres. (see, e.g., Jayasena, 1999, Clin Chem 45:1628-50; Kusser2000, J. Biotechnol. 74: 27-39; Colas, 2000, Curr Opin Chem Biol 4:54-9). Aptamers which specifically bind arginine and AMP have been described as well (see, Patel and Suri, 2000, J. Biotech. 74:39-60). Oligonucleotide aptamers that bind to a specific amino acid have been disclosed in Gold et al. (1995, Ann. Rev. Biochem. 64:763-97). RNA aptamers that bind amino acids have also been described (Ames and Breaker, 2011, RNA Biol. 8; 82-89; Mannironi et al., 2000, RNA 6:520-27; Famulok, 1994, J. Am. Chem. Soc. 116:1698-1706).

A binding agent can be made by modifying naturally-occurring or synthetically-produced proteins by genetic engineering to introduce one or more mutations in the amino acid sequence to produce engineered proteins that bind to a specific component or feature of a polypeptide (e.g., NTAA, CTAA, or post-translationally modified amino acid or a peptide). For example, exopeptidases (e.g., aminopeptidases, carboxypeptidases, dipeptidyl peptidase, dipeptidyl aminopeptidase), exoproteases, mutated exoproteases, mutated anticalins, mutated ClpSs, antibodies, or tRNA synthetases can be modified to create a binding agent that selectively binds to a particular NTAA. In another example, carboxypeptidases can be modified to create a binding agent that selectively binds to a particular CTAA. A binding agent can also be designed or modified, and utilized, to specifically bind a modified NTAA or modified CTAA, for example one that has a post-translational modification (e.g., phosphorylated NTAA or phosphorylated CTAA) or one that has been modified with a label (e.g., PTC, 1-fluoro-2,4-dinitrobenzene (using Sanger's reagent, DNFB), dansyl chloride (using DNS-Cl, or 1-dimethylaminonaphthalene-5-sulfonyl chloride), or using a thioacylation reagent, a thioacetylation reagent, an acetylation reagent, an amidination (guanidinylation) reagent, or a thiobenzylation reagent). Strategies for directed evolution of proteins are known in the art (e.g., Yuan et al., 2005, Microbiol. Mol. Biol. Rev. 69:373-392), and include phage display, ribosomal display, mRNA display, CIS display, CAD display, emulsions, cell surface display method, yeast surface display, bacterial surface display, etc.

In another example, highly-selective engineered ClpSs have also been described in the literature. Emili et al. describe the directed evolution of an E. coli. ClpS protein via phage display, resulting in four different variants with the ability to selectively bind NTAAs for aspartic acid, arginine, tryptophan, and leucine residues (U.S. Pat. No. 9,566,335, incorporated by reference in its entirety). In one embodiment, the binding moiety of the binding agent comprises a member of the evolutionarily conserved ClpS family of adaptor proteins involved in natural N-terminal protein recognition and binding or a variant thereof. (See e.g., Schuenemann et al., (2009) EMBO Reports 10(5); Roman-Hernandez et al., (2009) PNAS 106(22):8888-93; Guo et al., (2002) JBC 277(48): 46753-62; Wang et al., (2008) Molecular Cell 32: 406-414). In some embodiments, the amino acid residues corresponding to the ClpS hydrophobic binding pocket identified in Schuenemann et al. are modified in order to generate a binding moiety with the desired selectivity.

In one embodiment, the binding moiety comprises a member of the UBR box recognition sequence family, or a variant of the UBR box recognition sequence family. UBR recognition boxes are described in Tasaki et al., (2009), JBC 284(3): 1884-95. For example, the binding moiety may comprise UBR1, UBR2, or a mutant, variant, or homologue thereof.

In certain embodiments, the binding agent further comprises one or more detectable labels such as fluorescent labels, in addition to the binding moiety. In some embodiments, the binding agent does not comprise a polynucleotide such as a coding tag. Optionally, the binding agent comprises a synthetic or natural antibody. In some embodiments, the binding agent comprises an aptamer. In one embodiment, the binding agent comprises a polypeptide, such as a modified member of the ClpS family of adaptor proteins, such as a variant of an E. coli ClpS binding polypeptide, and a detectable label. In one embodiment, the detectable label is optically detectable. In some embodiments, the detectable label comprises a fluorescently moiety, a color-coded nanoparticle, a quantum dot or any combination thereof. In one embodiment the label comprises a polystyrene dye encompassing a core dye molecule such as a FluoSphere™, Nile Red, fluorescein, rhodamine, derivatized rhodamine dyes, such as TAMRA, phosphor, polymethadine dye, fluorescent phosphoramidite, TEXAS RED, green fluorescent protein, acridine, cyanine, cyanine 5 dye, cyanine 3 dye, 5-(2'-aminoethyl)-aminonaphthalene-1-sulfonic acid (EDANS), BODIPY, 120 ALEXA or a derivative or modification of any of the foregoing. In one embodiment, the detectable label is resistant to photobleaching while producing lots of signal (such as photons) at a unique and easily detectable wavelength, with high signal-to-noise ratio.

In a particular embodiment, anticalins are engineered for both high affinity and high specificity to labeled NTAAs (e.g. PTC, modified-PTC, Cbz, DNP, SNP, acetyl, guanidinyl, amino guanidinyl, heterocyclic methanimine, etc.). Certain varieties of anticalin scaffolds have suitable shape for binding single amino acids, by virtue of their beta barrel structure. An N-terminal amino acid (either with or without modification) can potentially fit and be recognized in this "beta barrel" bucket. High affinity anticalins with engineered novel binding activities have been described (reviewed by Skerra, 2008, FEBS J. 275: 2677-2683). For example, anticalins with high affinity binding (low nM) to fluorescein and digoxygenin have been engineered (Gebauer et al., 2012, Methods Enzymol 503: 157-188). Engineering of alternative scaffolds for new binding functions has also been reviewed by Banta et al. (2013, Annu. Rev. Biomed. Eng. 15:93-113).

In some embodiments, the binding agent is linked, directly or indirectly, to a multimerization domain. Thus, monomeric, dimeric, and higher order (e.g., 3, 4, 5, or more) multimeric polypeptides comprising one or more binding agents are provided herein. In some specific embodiments, the binding agent is dimeric. In some examples, two polypeptides of the invention can be covalently or non-covalently attached to each other to form a dimer.

In some embodiments, the binding agent is derived from a biological, naturally occurring, non-naturally occurring, or synthetic source. In some examples, the binding agent is derived from de novo protein design (Huang et al., (2016) 537(7620):320-327). In some examples, the binding agent has a structure, sequence, and/or activity designed from first principles.

In some embodiments, a binding agent can be utilized that selectively binds a modified C-terminal amino acid (CTAA). Carboxypeptidases are proteases that cleave/eliminate terminal amino acids containing a free carboxyl group. A number of carboxypeptidases exhibit amino acid preferences, e.g., carboxypeptidase B preferentially cleaves at basic amino acids, such as arginine and lysine. A carboxypeptidase can be modified to create a binding agent that selectively binds to particular amino acid. In some embodiments, the carboxypeptidase may be engineered to selectively bind both the modification moiety as well as the alpha-carbon R group of the CTAA. Thus, engineered carboxypeptidases may specifically recognize 20 different CTAAs representing the standard amino acids in the context of a C-terminal label. Control of the stepwise degradation from the C-terminus of the peptide is achieved by using engineered carboxypeptidases that are only active (e.g., binding activity or catalytic activity) in the presence of the label. In one example, the CTAA may be modified by a para-Nitroanilide or 7-amino-4-methylcoumarinyl group.

Other potential scaffolds that can be engineered to generate binding agents for use in the methods described herein include: an anticalin, a lipocalin, an amino acid tRNA synthetase (aaRS), ClpS, an Affilin®, an Adnectin™, a T cell receptor, a zinc finger protein, a thioredoxin, GST A1-1, DARPin, an affimer, an affitin, an alphabody, an avimer, a monobody, an antibody, a single domain antibody, a nanobody, EETI-II, HPSTI, intrabody, PHD-finger, V(NAR) LDTI, evibody, Ig(NAR), knottin, maxibody, microbody, neocarzinostatin, pVIII, tendamistat, VLR, protein A scaffold, MTI-II, ecotin, GCN4, Im9, kunitz domain, PBP, trans-body, tetranectin, WW domain, CBM4-2, DX-88, GFP, iMab, Ldl receptor domain A, Min-23, PDZ-domain, avian pancreatic polypeptide, charybdotoxin/10Fn3, domain antibody (Dab), a2p8 ankyrin repeat, insect defensing A peptide, Designed AR protein, C-type lectin domain, staphylococcal nuclease, Src homology domain 3 (SH3), or Src homology domain 2 (SH2). See e.g., El-Gebali et al., (2019) Nucleic Acids Research 47:D427-D432 and Finn et al., (2013) Nucleic Acids Res. 42(Database issue):D222-D230. In some embodiments, a binding agent is derived from an enzyme which binds one or more amino acids (e.g., an aminopeptidase). In certain embodiments, a binding agent can be derived from an anticalin or a Clp protease adaptor protein (ClpS).

In some cases, a binding agent may bind to a post-translationally modified amino acid. In some embodiments, detection of internal post-translationally modified amino acids (e.g., phosphorylation, glycosylation, succinylation, ubiquitination, S-Nitrosylation, methylation, N-acetylation, lipidation, etc.) is be accomplished prior to detection and elimination of terminal amino acids (e.g., NTAA or CTAA). In one example, a peptide is contacted with binding agents for PTM modifications, and information from a corresponding coding tag is transferred to the recording tag associated with the immobilized peptide. Once the detection and transfer of information relating to amino acid modifications is complete, the PTM modifying groups can be removed before detection and transfer of coding tag information for the primary amino acid sequence using N-terminal or C-terminal degradation methods. Thus, resulting extended nucleic acids indicate the presence of post-translational modifications in a peptide sequence, though not the sequential order, along with primary amino acid sequence information.

In some embodiments, detection of internal post-translationally modified amino acids may occur concurrently with detection of primary amino acid sequence. In one example, an NTAA (or CTAA) is contacted with a binding agent specific for a post-translationally modified amino acid, either alone or as part of a library of binding agents (e.g., library composed of binding agents for the 20 standard amino acids and selected post-translational modified amino acids). Successive cycles of terminal amino acid elimination and contact with a binding agent (or library of binding agents) follow. Thus, resulting extended nucleic acids on the recording tag associated with the immobilized peptide indicate the presence and order of post-translational modifications in the context of a primary amino acid sequence.

In certain embodiments, a macromolecule, e.g., a polypeptide, is also contacted with a non-cognate binding agent. As used herein, a non-cognate binding agent is referring to a binding agent that is selective for a different target (e.g. polypeptide feature or component) than the particular target being considered. For example, if the n NTAA is phenylalanine, and the peptide is contacted with three binding agents selective for phenylalanine, tyrosine, and asparagine, respectively, the binding agent selective for phenylalanine would be first binding agent capable of selectively binding to the n, NTAA (i.e., phenylalanine), while the other two binding agents would be non-cognate binding agents for that peptide (since they are selective for NTAAs other than phenylalanine). The tyrosine and asparagine binding agents may, however, be cognate binding agents for other peptides in the sample. If the n NTAA (phenylalanine) was then cleaved from the peptide, thereby converting the n−1 amino acid of the peptide to the n−1 NTAA (e.g., tyrosine), and the peptide was then contacted with the same three binding agents, the binding agent selective for tyrosine would be second binding agent capable of selectively binding to the n−1 NTAA (i.e., tyrosine), while the other two binding agents would be non-cognate binding agents (since they are selective for NTAAs other than tyrosine).

Thus, it should be understood that whether an agent is a binding agent or a non-cognate binding agent will depend on the nature of the particular polypeptide feature or component currently available for binding. Also, if multiple polypeptides are analyzed in a multiplexed reaction, a binding agent for one polypeptide may be a non-cognate binding agent for another, and vice versa. According, it should be understood that the following description concerning binding agents is applicable to any type of binding agent described herein (i.e., both cognate and non-cognate binding agents).

In certain embodiments, the concentration of the binding agents in a solution is controlled to reduce background and/or false positive results of the assay. In some embodiments, the concentration of a binding agent can be at any suitable concentration, e.g., at about 0.0001 nM, about 0.001 nM, about 0.01 nM, about 0.1 nM, about 1 nM, about 2 nM, about 5 nM, about 10 nM, about 20 nM, about 50 nM, about 100 nM, about 200 nM, about 500 nM, or about 1,000 nM. In other embodiments, the concentration of a soluble conjugate used in the assay is between about 0.0001 nM and about 0.001 nM, between about 0.001 nM and about 0.01 nM, between about 0.01 nM and about 0.1 nM, between about 0.1 nM and about 1 nM, between about 1 nM and about 2 nM, between about 2 nM and about 5 nM, between about 5 nM and about 10 nM, between about 10 nM and about 20 nM, between about 20 nM and about 50 nM, between about 50 nM and about 100 nM, between about 100 nM and about 200 nM, between about 200 nM and about 500 nM, between about 500 nM and about 1000 nM, or more than about 1,000 nM.

In some embodiments, the ratio between the soluble binding agent molecules and the immobilized macromolecule, e.g., polypeptides, can be at any suitable range, e.g., at about 0.00001:1, about 0.0001:1, about 0.001:1, about 0.01:1, about 0.1:1, about 1:1, about 2:1, about 5:1, about 10:1, about 15:1, about 20:1, about 25:1, about 30:1, about 35:1, about 40:1, about 45:1, about 50:1, about 55:1, about 60:1, about 65:1, about 70:1, about 75:1, about 80:1, about 85:1, about 90:1, about 95:1, about 100:1, about 104:1, about 105:1, about 106:1, or higher, or any ratio in between the above listed ratios. Higher ratios between the soluble binding agent molecules and the immobilized polypeptide(s) and/or the nucleic acids can be used to drive the binding and/or the coding tag information transfer to completion. This may be particularly useful for detecting and/or analyzing low abundance polypeptides in a sample.

C. Coding Tag

The binding agent described comprises or is associated with a coding tag containing identifying information regarding (e.g., representing or correlating to) the binding agent. In some embodiments, the identifying information from the coding tag comprises information regarding the identity of the target bound by the binding agent. In some embodiments, the identifying information from the coding tag comprises or is associated with information regarding the identity of the one or more amino acid(s) on the peptide bound by the binding agent. In some cases, the coding tag includes a partial restriction enzyme recognition sequence used for the cleavage step. For example, the coding tag may include a sequence (or portion thereof) that can be recognized by a double strand nucleic acid cleaving reagent (e.g., a restriction enzyme). In some cases, the coding tag may include a single stranded sequence that can be recognized by the double strand nucleic acid cleaving reagent (e.g., a restriction enzyme) once it is double stranded.

The coding tag associated with the binding agent is or comprises a polynucleotide with any suitable length, e.g., a nucleic acid molecule of about 2 bases to about 100 bases, including any integer including 2 and 100 and in between, that comprises identifying information for its associated binding agent. A "coding tag" may also be made from a "sequenceable polymer" (see, e.g., Niu et al., 2013, Nat. Chem. 5:282-292; Roy et al., 2015, Nat. Commun. 6:7237; Lutz, 2015, Macromolecules 48:4759-4767; each of which are incorporated by reference in its entirety). A coding tag may comprise an encoder sequence or a sequence with identifying information, which is optionally flanked by one spacer on one side or optionally flanked by a spacer on each side. A coding tag may also be comprised of an optional UMI and/or an optional binding cycle-specific barcode. A coding tag may refer to the coding tag that is directly attached to a binding agent, to a complementary sequence hybridized to the coding tag directly attached to a binding agent (e.g., for double stranded coding tags), or to coding tag information present in an extended nucleic acid on the recording tag. In certain embodiments, a coding tag may further comprise a binding cycle specific spacer or barcode, a unique molecular identifier, a universal priming site, or any combination thereof.

A coding tag may be a single stranded molecule, a double stranded molecule, or a partially double stranded. A coding tag may comprise blunt ends, overhanging ends, or one of each. In some embodiments, a coding tag is partially double stranded, which prevents annealing of the coding tag to internal encoder and spacer sequences in a growing extended recording tag.

In some embodiments, the coding tag may comprise a hairpin. In certain embodiments, the hairpin comprises mutually complementary nucleic acid regions are connected through a nucleic acid strand. In some embodiments, the nucleic acid hairpin can also further comprise 3' and/or 5' single-stranded region(s) extending from the double-stranded stem segment. In some examples, the hairpin comprises a single strand of nucleic acid.

In some embodiments, a binding agent described comprises a coding tag containing identifying information regarding the binding agent. In some embodiments, the identifying information from the coding tag comprises information regarding the identity of the target bound by the binding agent. In some embodiments, the identifying information from the coding tag comprises information regarding the identity of the one or more amino acid(s) on the peptide bound by the binding agent.

A coding tag is a nucleic acid molecule of about 3 bases to about 100 bases that provides unique identifying information for its associated binding agent. A coding tag may comprise about 3 to about 90 bases, about 3 to about 80 bases, about 3 to about 70 bases, about 3 to about 60 bases, about 3 bases to about 50 bases, about 3 bases to about 40 bases, about 3 bases to about 30 bases, about 3 bases to about 20 bases, about 3 bases to about 10 bases, or about 3 bases to about 8 bases. In some embodiments, a coding tag is about 3 bases, 4 bases, 5 bases, 6 bases, 7 bases, 8 bases, 9 bases, 10 bases, 11 bases, 12 bases, 13 bases, 14 bases, 15 bases, 16 bases, 17 bases, 18 bases, 19 bases, 20 bases, 25 bases, 30 bases, 35 bases, 40 bases, 55 bases, 60 bases, 65 bases, 70 bases, 75 bases, 80 bases, 85 bases, 90 bases, 95 bases, or 100 bases in length. A coding tag may be composed of DNA, RNA, polynucleotide analogs, or a combination thereof. Polynucleotide analogs include PNA, gPNA, BNA, GNA, TNA, LNA, morpholino polynucleotides, 2'-O-Methyl polynucleotides, alkyl ribosyl substituted polynucleotides, phosphorothioate polynucleotides, and 7-deaza purine analogs.

The binding agent may be attached to the coding tag in any suitable manner and position such that it does not disrupt the enzymatic reactions (e.g., function of the nucleic acid joining reagent, polymerase and double strand nucleic acid cleaving reagent) of the provided methods. For example, the binding agent may be attached to the coding tag in any suitable manner as along as the coding tag is attached in a way that the coding tag has an available 3' end. In some particular embodiments, the coding tag has a spacer that is a 3' overhang. In some embodiments, the binding agent is attached to the coding tag at the 5' end of the coding tag. In some embodiments, the binding agent is attached to the coding tag at the loop region. In some embodiments, the binding agent is attached to the coding tag at a location that is near the loop to the 5' end of the recoding tag. A coding tag can be joined to a binding agent directly or indirectly (e.g., via a linker), by any means known in the art, including covalent and non-covalent interactions. In some embodiments, a coding tag may be joined to binding agent enzymatically or chemically. In some embodiments, a coding tag may be joined to a binding agent via ligation. In other embodiments, a coding tag is joined to a binding agent via affinity binding pairs (e.g., biotin and streptavidin). In some cases, a coding tag may be joined to a binding agent to an unnatural amino acid, such as via a covalent interaction with an unnatural amino acid.

In some embodiments, a binding agent is joined to a coding tag via SpyCatcher-SpyTag interaction. The SpyTag peptide forms an irreversible covalent bond to the Spy-Catcher protein via a spontaneous isopeptide linkage, thereby offering a genetically encoded way to create peptide interactions that resist force and harsh conditions (Zakeri et al., 2012, Proc. Natl. Acad. Sci. 109:E690-697; Li et al., 2014, J. Mol. Biol. 426:309-317). A binding agent may be expressed as a fusion protein comprising the SpyCatcher protein. In some embodiments, the SpyCatcher protein is appended on the N-terminus or C-terminus of the binding agent. The SpyTag peptide can be coupled to the coding tag using standard conjugation chemistries (Hermanson, Bioconjugate Techniques, (2013) Academic Press).

In some embodiments, an enzyme-based strategy is used to join the binding agent to a coding tag. For example, the binding agent may be joined to a coding tag using a formylglycine (FGly)-generating enzyme (FGE). In one example, a protein, e.g., SpyLigase, is used to join the binding agent to the coding tag (Fierer et al., Proc Natl Acad Sci USA. 2014; 111(13): E1176-E1181).

In other embodiments, a binding agent is joined to a coding tag via SnoopTag-SnoopCatcher peptide-protein interaction. The SnoopTag peptide forms an isopeptide bond with the SnoopCatcher protein (Veggiani et al., Proc. Natl. Acad. Sci. USA, 2016, 113:1202-1207). A binding agent may be expressed as a fusion protein comprising the Snoop-Catcher protein. In some embodiments, the SnoopCatcher protein is appended on the N-terminus or C-terminus of the binding agent. The SnoopTag peptide can be coupled to the coding tag using standard conjugation chemistries.

In yet other embodiments, a binding agent is joined to a coding tag via the HaloTag® protein fusion tag and its chemical ligand. HaloTag is a modified haloalkane dehalogenase designed to covalently bind to synthetic ligands (HaloTag ligands) (Los et al., 2008, ACS Chem. Biol. 3:373-382). The synthetic ligands comprise a chloroalkane linker attached to a variety of useful molecules. A covalent bond forms between the HaloTag and the chloroalkane linker that is highly specific, occurs rapidly under physiological conditions, and is essentially irreversible.

In some cases, a binding agent is joined to a coding tag by attaching (conjugating) using an enzyme, such as sortase-mediated labeling (See e.g., Antos et al., Curr Protoc Protein Sci. (2009) CHAPTER 15: Unit-15.3; International Patent Publication No. WO2013003555). The sortase enzyme catalyzes a transpeptidation reaction (See e.g., Falck et al, Antibodies (2018) 7(4):1-19). In some aspects, the binding agent is modified with or attached to one or more N-terminal or C-terminal glycine residues.

In some embodiments, a binding agent is joined to a coding tag using a cysteine bioconjugation method. In some embodiments, a binding agent is joined to a coding tag using 7c-clamp-mediated cysteine bioconjugation (See e.g., Zhang et al., Nat Chem. (2016) 8(2):120-128). In some cases, a binding agent is joined to a coding tag using 3-arylpropiolonitriles (APN)-mediated tagging (e.g. Koniev et al., Bioconjug Chem. 2014; 25(2):202-206).

In some embodiments, a set of coding tags used in a cycle of binding and information transfer may include cycle information, such as using cycle specific sequences. In one embodiment, the coding tags comprise binding cycle-specific sequences. In some embodiments, the coding tags within a collection of binding agents share a common spacer sequence used in an assay (e.g. the entire library of binding agents used in a multiple binding cycle method possess a common spacer in their coding tags). In another embodiment, the coding tags are comprised of a binding cycle tags, identifying a particular binding cycle. In other embodiments, the coding tags within a library of binding agents have a binding cycle specific spacer sequence. In some embodiments, a coding tag comprises one binding cycle specific spacer sequence. For example, a coding tag for binding agents used in the first binding cycle comprise a "cycle 1" specific spacer sequence, a coding tag for binding agents used in the second binding cycle comprise a "cycle 2" specific spacer sequence, and so on up to "n" binding cycles. In further embodiments, coding tags for binding agents used in the first binding cycle comprise a "cycle 1" specific spacer sequence and a "cycle 2" specific spacer sequence, coding tags for binding agents used in the second binding cycle comprise a "cycle 2" specific spacer sequence and a "cycle 3" specific spacer sequence, and so on up to "n" binding cycles. This embodiment is useful for subsequent PCR assembly of non-concatenated extended recording tags after the binding cycles are completed. In some embodiments, a spacer sequence comprises a sufficient number of bases to anneal to a complementary spacer sequence in a recording tag or extended recording tag to initiate a primer extension reaction or sticky end ligation reaction.

A cycle specific spacer sequence can also be designed such that information transfer occurs on a conditional basis. In one example, the first binding cycle transfers information from the coding tag to a recording tag, and subsequent binding cycles can in a manner that is dependent on previously added spacer sequences. More specifically, coding tags for binding agents used in the first binding cycle comprise a "cycle 1" specific spacer sequence and a "cycle 2" specific spacer sequence, coding tags for binding agents used in the second binding cycle comprise a "cycle 2" specific spacer sequence and a "cycle 3" specific spacer sequence, and so on up to "n" binding cycles. Coding tags of binding agents from the first binding cycle are capable of annealing to recording tags via complementary cycle 1 specific spacer sequences. Upon transfer of the coding tag information to the recording tag, the cycle 2 specific spacer sequence is positioned at the 3' terminus of the extended recording tag at the end of binding cycle 1. Coding tags of binding agents from the second binding cycle are capable of annealing to the extended recording tags via complementary cycle 2 specific spacer sequences. Upon transfer of the coding tag information to the extended recording tag, the cycle 3 specific spacer sequence is positioned at the 3' terminus of the extended recording tag at the end of binding cycle 2, and so on through "n" binding cycles. This embodiment provides that transfer of binding information in a particular binding cycle among multiple binding cycles will only occur on (extended) recording tags that have experienced the previous binding cycles. In some cases, information is transferred from a second (or higher order) coding tag to the extended recording tag if the spacer added by the previous coding tag matches at least a portion of the spacer of the second coding tag.

In some embodiments, a binding agent may fail to bind to a cognate macromolecule. Oligonucleotides comprising binding cycle specific spacers after each binding cycle as a "chase" step can be used to keep the binding cycles synchronized even if the event of a binding cycle failure. For example, if a cognate binding agent fails to bind to a macromolecule during binding cycle 1, adding a chase step following binding cycle 1 using oligonucleotides comprising both a cycle 1 specific spacer, a cycle 2 specific spacer, and a "null" encoder sequence. The "null" encoder sequence can be the absence of an encoder sequence or, preferably, a specific barcode that positively identifies a "null" binding cycle. The "null" oligonucleotide is capable of annealing to the recording tag via the cycle 1 specific spacer, and the cycle 2 specific spacer is transferred to the recording tag. Thus, binding agents from binding cycle 2 are capable of annealing to the extended recording tag via the cycle 2 specific spacer despite the failed binding cycle 1 event. The "null" oligonucleotide marks binding cycle 1 as a failed binding event within the extended recording tag.

In preferred embodiment, binding cycle-specific encoder sequences are used in coding tags. Binding cycle-specific encoder sequences may be accomplished either via the use of completely unique analyte (e.g., NTAA)-binding cycle encoder barcodes or through a combinatoric use of an analyte (e.g., NTAA) encoder sequence joined to a cycle-specific barcode. The advantage of using a combinatoric approach is that fewer total barcodes need to be designed. For a set of 20 analyte binding agents used across 10 cycles, only 20 analyte encoder sequence barcodes and 10 binding cycle specific barcodes need to be designed. In contrast, if the binding cycle is embedded directly in the binding agent encoder sequence, then a total of 200 independent encoder barcodes may need to be designed. An advantage of embedding binding cycle information directly in the encoder sequence is that the total length of the coding tag can be minimized when employing error-correcting barcodes on a nanopore readout. The use of error-tolerant barcodes allows highly accurate barcode identification using sequencing platforms and approaches that are more error-prone, but have other advantages such as rapid speed of analysis, lower cost, and/or more portable instrumentation. One such example is a nanopore-based sequencing readout.

II. MACROMOLECULE ANALYSIS ASSAY

The provided methods for analysis of macromolecules, e.g., peptides, polypeptides, and proteins, including a step of transferring information using the sequential encoding methods described to a recording tag may include additional steps, treatments, and reactions. In some embodiments, the macromolecule is a polypeptide and a polypeptide analysis assay is performed. In some embodiments, the sequence (or a portion of the sequence thereof) and/or the identity of a protein is determined using a polypeptide analysis assay. In some examples, the polypeptide analysis assay includes assessing at least a partial sequence or identity of the polypeptide using suitable techniques or procedures. For example, at least a partial sequence of the polypeptide can be assessed by N-terminal amino acid analysis or C-terminal amino acid analysis. In some embodiments, at least a partial sequence of the polypeptide can be assessed using a ProteoCode assay. In some examples, at least a partial sequence of the polypeptide can be assessed by applying some of the techniques or procedures disclosed and/or claimed in U.S. Patent Publications Nos. US 20190145982 A1, US 20200348308 A1, US 20200348307 A1, US 20210208150 A1.

In embodiments relating to methods of analyzing peptides or polypeptides, the method generally includes contacting a binding agent to at least a terminal amino acid (e.g., NTAA or CTAA) of a polypeptide, protein or peptide, and upon contacting, transferring the information from the coding tag to the recording tag associated with the polypeptide, protein or peptide, thereby generating a first order extended recording tag (a cycle of encoding). An exemplary cycle of encoding according to the methods described herein is shown in FIG. 1B. The binding agent as shown in FIG. 1B is attached to the coding tag comprising identifying information regarding the binding agent (the binding agent barcode, BBC) by a linker. In some embodiments, the binding agent can be attached or joined to the coding tag in locations other than depicted (e.g., at the loop region of the coding tag or others). To transfer the BBC information, a polymerase, a nucleic acid joining reagent (such as DNA ligase) and a double strand nucleic acid cleaving reagent (such as restriction enzyme) is provided. These reagents can be added either subsequently (one enzyme at a time, or two enzymes (polymerase and DNA ligase) followed by restriction enzyme), or as a mixture of three enzymes. Upon ligation of the 5' end of the recording tag to the 3' end of the coding tag, polymerase extends the 3' (non-ligated) end of the recording tag to create a dsDNA molecule containing 2-base pair spacers adjacent to their respective restriction enzyme sites. Following double strand generation, the restriction enzyme binds and cuts adjacent to its recognition site. After cleavage, the dsDNA on the recording tag now contains the binding agent-specific barcode (BBC) and a 2 nt 3' overhang, which serves as the spacer sequence in the next rounds of encoding. In some embodiments, after a cycle of information transfer (encoding), a portion of the polypeptide for analysis can be removed from the polypeptide (such as the terminal amino acid or a terminal dipeptide). The cycle of steps shown in FIG. 1B may be repeated one or more times with additional binding agents and corresponding coding tags to further extend the recording tag.

In some further embodiment, the method comprises labeling or modifying the macromolecule (e.g. peptide) prior to or after the macromolecule is contacted with the binding agent. For example, the terminal amino acid of the polypeptide, protein or peptide bound by the binding agent may be a chemically labeled or modified terminal amino acid. In some further embodiments, the method further includes removing or eliminating the terminal amino acid (e.g., NTAA or CTAA) from the polypeptide, protein or peptide after the information transfer step. The terminal amino acid eliminated may be a chemically labeled or modified terminal amino acid. Removal of the NTAA by contacting with an enzyme or chemical reagents converts the penultimate amino acid of the polypeptide, protein or peptide to a terminal amino acid. The polypeptide analysis may include one or more cycles of binding with additional binding agents to the terminal amino acid, and transferring information from the coding tags to the extended nucleic acid thereby generating a higher order extended recording tag containing information regarding two or more binding agents, and eliminating the terminal amino acid in a cyclic manner. Additional binding, transferring information, and removal, can occur as described up to n amino acids to generate an $n^{th}$ order extended nucleic acid, which collectively represent the polypeptide, protein or peptide. The recording tag is used to record information gathered from one or more binding events between one or more binding agents and the macromolecule to be analyzed.

In some of any provided embodiments, steps including the NTAA in the described exemplary approach can be performed instead with a C terminal amino acid (CTAA).

In some embodiments, the order of the steps in the process for a degradation-based peptide or polypeptide sequencing assay can be reversed or be performed in various orders. For example, in some embodiments, the terminal amino acid labeling can be conducted before and/or after the polypeptide is bound to the binding agent.

Provided herein is a method for analyzing a macromolecule comprising the steps of: (a) providing a macromolecule and an associated recording tag joined to a support; (b) contacting the macromolecule with a binding agent capable of binding to the macromolecule, wherein the binding agent comprises a coding tag with identifying information regarding the binding agent, to allow binding between the macromolecule and the binding agent; (c) joining the 5' end of the recording tag to the 3'end of the coding tag by a nucleic acid joining reagent; (d) extending the recording tag using the coding tag as a template by a polymerase, generating a double stranded extended recording tag; and (e) cleaving the double stranded extended recording tag with a double strand nucleic acid cleaving reagent to generate a 3' overhang in the extended recording tag. In some cases, the binding agent is removed after step (e). In some embodiments, the method further includes analyzing the extended recoding tag. In some aspects, the method further includes adding a universal priming site to the extended recording tag, prior to analyzing the extended recording tag.

In some examples, step (a) is performed before steps (b), (c), (d) and (e). Steps (c), (d) and (e) may be performed in a step-wise manner by nature of the design, but the reagents may be provided in a mixture. In some embodiments, step (b) is performed before step (c) and step (d), for example, by first providing a nucleic acid joining reagent, then providing the polymerase and the double strand nucleic acid cleaving reagent together. In some cases, the steps occur in the order (c), (d), and (e). In some particular embodiments, the steps are performed in the order: (a), (b), (c), (d), and (e) optionally repeating steps (b), (c), (d) and (e) one or more times.

In some embodiments, the method further includes step removing a portion of the polypeptide, such as the terminal amino acid (e.g., N-terminal amino acid (NTAA)) of the polypeptide, protein or peptide to expose a new terminal amino acid of the polypeptide, protein or peptide. In some cases, a second cycle of steps (b), (c), (d), (e) is repeated after removing at least a portion of the polypeptide after the first cycle of steps (b), (c), (d), (e).

In some embodiments, the method includes treating the target polypeptide, protein or peptide with a reagent for modifying a terminal amino acid of the polypeptide, protein or peptide. In some aspects, the reagent for modifying a terminal amino acid of a polypeptide comprises a chemical agent or an enzymatic agent. In some embodiments, the target polypeptide, protein or peptide is contacted with the reagent for modifying a terminal amino acid before step (b). In some embodiments, the target polypeptide, protein or peptide is contacted with the reagent for modifying a terminal amino acid before removing the terminal amino acid.

In some embodiments, the method further includes removing the binding agent after transferring information from the coding ag to the recording tag. In some aspects, the binding agent is removed after step (e). In some aspects, the binding agent is removed before repeating step (b). In some aspects, removing the binding agent is performed after transferring information from the coding tag to the recording tag associated with the macromolecule for analysis.

A. Sample and Macromolecule

In some embodiments, the analysis assay is performed on one or more macromolecules of unknown identity that is obtained from a sample. In some cases, the macromolecules are from a mixture of molecules obtained from a sample. A macromolecule can be a large molecule composed of smaller subunits. In certain embodiments, a macromolecule is a protein, a protein complex, polypeptide, peptide, nucleic acid molecule, carbohydrate, lipid, macrocycle, or a chimeric macromolecule. A macromolecule (e.g., protein, polypeptide, peptide) in the methods disclosed herein may be obtained from any suitable source or sample.

The methods disclosed herein can be used for analysis, including detection, identification, quantitation and/or sequencing, of a plurality of macromolecules simultaneously (multiplexing). Multiplexing as used herein refers to analysis of a plurality of macromolecules (e.g. polypeptides) in the same assay. The plurality of macromolecules can be derived from the same sample or different samples. The plurality of macromolecules can be derived from the same subject or different subjects. The plurality of macromolecules that are analyzed can be different macromolecules, or the same macromolecule derived from different samples. A plurality of macromolecules includes 2 or more macromolecules, 5 or more macromolecules, 10 or more macromolecules, 50 or more macromolecules, 100 or more macromolecules, 500 or more macromolecules, 1000 or more macromolecules, 5,000 or more macromolecules, 10,000 or more macromolecules, 50,000 or more macromolecules, 100,000 or more macromolecules, 500,000 or more macromolecules, or 1,000,000 or more macromolecules.

In some embodiments, the macromolecules (e.g., proteins, polypeptides, or peptides) are obtained from a sample that is a biological sample. In some embodiments, the sample comprises but is not limited to, mammalian or human cells, yeast cells, and/or bacterial cells. In some embodiments, the sample contains cells that are from a sample obtained from a multicellular organism. For example, the sample may be isolated from an individual. In some embodiments, the sample may comprise a single cell type or multiple cell types. In some embodiments, the sample may be obtained from a mammalian organism or a human, for example by puncture, or other collecting or sampling procedures. In some embodiments, the sample comprises two or more cells.

In some embodiments, the biological sample may contain whole cells and/or live cells and/or cell debris. In some examples, a suitable source or sample, may include but is not limited to: biological samples, such as biopsy samples, cell cultures, cells (both primary cells and cultured cell lines), sample comprising cell organelles or vesicles, tissues and tissue extracts; of virtually any organism. For example, a suitable source or sample, may include but is not limited to: biopsy; fecal matter; bodily fluids (such as blood, whole blood, serum, plasma, urine, lymph, bile, aqueous humor, breast milk, cerumen (earwax), chyle, chyme, endolymph, perilymph, exudates, cerebrospinal fluid, interstitial fluid, aqueous or vitreous humor, colostrum, sputum, amniotic fluid, saliva, anal and vaginal secretions, gastric acid, gastric juice, lymph, mucus (including nasal drainage and phlegm), pericardial fluid, peritoneal fluid, pleural fluid, pus, rheum, saliva, sebum (skin oil), sputum, synovial fluid, perspiration and semen, a transudate, vomit and mixtures of one or more thereof, an exudate (e.g., fluid obtained from an abscess or any other site of infection or inflammation) or fluid obtained from a joint (normal joint or a joint affected by disease such as rheumatoid arthritis, osteoarthritis, gout or septic arthritis) of virtually any organism, with mammalian-derived samples, including microbiome-containing samples, being preferred and human-derived samples, including microbiome-containing samples, being particularly preferred; environmental samples (such as air, agricultural, water and soil samples); microbial samples including samples derived from microbial biofilms and/or communities, as well as microbial spores; tissue samples including tissue sections, research samples including extracellular fluids, extracellular supernatants from cell cultures, inclusion bodies in bacteria, cellular components including mitochondria and cellular periplasm. In some embodiments, the biological sample comprises a body fluid or is derived from a body fluid, wherein the body fluid is obtained from a mammal or a human. In some embodiments, the sample includes bodily fluids, or cell cultures from bodily fluids.

In some embodiments, the macromolecules (e.g., polypeptides and proteins) may be obtained and prepared from a single cell type or multiple cell types. In some embodiments, the sample comprises a population of cells. In some embodiments, the macromolecules (e.g., proteins, polypeptides, or peptides) are from a cellular or subcellular component, an extracellular vesicle, an organelle, or an organized subcomponent thereof. The macromolecules (e.g., proteins, polypeptides, or peptides) may be from organelles, for example, mitochondria, nuclei, or cellular vesicles. In one embodiment, one or more specific types of single cells or subtypes thereof may be isolated. In some embodiments, the sample may include but are not limited to cellular organelles, (e.g., nucleus, golgi apparatus, ribosomes, mitochondria, endoplasmic reticulum, chloroplast, cell membrane, vesicles, etc.).

In certain embodiments, the macromolecule is or comprises a protein, a protein complex, a polypeptide, or peptide. Amino acid sequence information and post-translational modifications of a peptide, polypeptide, or protein are transduced into a nucleic acid encoded library that can be analyzed via next generation sequencing methods. A peptide may comprise L-amino acids, D-amino acids, or both. A peptide, polypeptide, protein, or protein complex may comprise a standard, naturally occurring amino acid, a modified amino acid (e.g., post-translational modification), an amino acid analog, an amino acid mimetic, or any combination thereof. In some embodiments, a peptide, polypeptide, or protein is naturally occurring, synthetically produced, or recombinantly expressed. In any of the aforementioned peptide embodiments, a peptide, polypeptide, protein, or protein complex may further comprise a post-translational modification. Standard, naturally occurring amino acids include Alanine (A or Ala), Cysteine (C or Cys), Aspartic Acid (D or Asp), Glutamic Acid (E or Glu), Phenylalanine (F or Phe), Glycine (G or Gly), Histidine (H or His), Isoleucine (I or Ile), Lysine (K or Lys), Leucine (L or Leu), Methionine (M or Met), Asparagine (N or Asn), Proline (P or Pro), Glutamine (Q or Gln), Arginine (R or Arg), Serine (S or Ser), Threonine (T or Thr), Valine (V or Val), Tryptophan (W or Trp), and Tyrosine (Y or Tyr). Non-standard amino acids include selenocysteine, pyrrolysine, and N-formylmethionine, β-amino acids, homo-amino acids, Proline and Pyruvic acid derivatives, 3-substituted Alanine derivatives, Glycine derivatives, ring-substituted Phenylalanine and Tyrosine Derivatives, linear core amino acids, and N-methyl amino acids.

A post-translational modification (PTM) of a peptide, polypeptide, or protein may be a covalent modification or enzymatic modification. Examples of post-translation modifications include, but are not limited to, acylation, acetylation, alkylation (including methylation), biotinylation, butyrylation, carbamylation, carbonylation, deamidation, deiminiation, diphthamide formation, disulfide bridge formation, eliminylation, flavin attachment, formylation, gamma-carboxylation, glutamylation, glycylation, glycosylation (e.g., N-linked, O-linked, C-linked, phosphoglycosylation), glypiation, heme C attachment, hydroxylation, hypusine formation, iodination, isoprenylation, lipidation, lipoylation, malonylation, methylation, myristolylation, oxidation, palmitoylation, pegylation, phosphopantetheinylation, phosphorylation, prenylation, propionylation, retinylidene Schiff base formation, S-glutathionylation, S-nitrosylation, S-sulfenylation, selenation, succinylation, sulfination, ubiquitination, and C-terminal amidation. A post-translational modification includes modifications of the amino terminus and/or the carboxyl terminus of a peptide, polypeptide, or protein. Modifications of the terminal amino group include, but are not limited to, des-amino, N-lower alkyl, N-di-lower alkyl, and N-acyl modifications. Modifications of the terminal carboxy group include, but are not limited to, amide, lower alkyl amide, dialkyl amide, and lower alkyl ester modifications (e.g., wherein lower alkyl is $C_1$-$C_4$ alkyl). A post-translational modification also includes modifications, such as but not limited to those described above, of amino acids falling between the amino and carboxy termini of a peptide, polypeptide, or protein. Post-translational modification can regulate a protein's "biology" within a cell, e.g., its activity, structure, stability, or localization. For example, phosphorylation plays an important role in regulation of protein, particularly in cell signaling (Prabakaran et al., 2012, Wiley Interdiscip Rev Syst Biol Med 4: 565-583). In another example, the addition of sugars to proteins, such as glycosylation, has been shown to promote protein folding, improve stability, and modify regulatory function and the attachment of lipids to proteins enables targeting to the cell membrane. A post-translational modification can also include peptide, polypeptide, or protein modifications to include one or more detectable labels.

In certain embodiments, a peptide, polypeptide, or protein can be fragmented. Peptides, polypeptides, or proteins can be fragmented by any means known in the art, including fragmentation by a protease or endopeptidase. In some embodiments, fragmentation of a peptide, polypeptide, or protein is targeted by use of a specific protease or endopeptidase. A specific protease or endopeptidase binds and cleaves at a specific consensus sequence (e.g., TEV protease). In other embodiments, fragmentation of a peptide, polypeptide, or protein is non-targeted or random by use of a non-specific protease or endopeptidase. A non-specific protease may bind and cleave at a specific amino acid residue rather than a consensus sequence (e.g., proteinase K is a non-specific serine protease). In some embodiments, proteinases and endopeptidases, such as those known in the art, can be used to cleave a protein or polypeptide into smaller peptide fragments include proteinase K, trypsin, chymotrypsin, pepsin, thermolysin, thrombin, Factor Xa, furin, endopeptidase, papain, pepsin, subtilisin, elastase, enterokinase, Genenase™ I, Endoproteinase LysC, Endoproteinase AspN, Endoproteinase GluC, etc. (Granvogl et al., 2007, Anal Bioanal Chem 389: 991-1002). In certain embodiments, a peptide, polypeptide, or protein is fragmented by proteinase K, or optionally, a thermolabile version of proteinase K to enable rapid inactivation. In some cases, Proteinase K is stable in denaturing reagents, such as urea and SDS, and enables digestion of completely denatured proteins. Protein and polypeptide fragmentation into peptides can be performed before or after attachment of a DNA tag or DNA recording tag.

Chemical reagents can also be used to digest proteins into peptide fragments. A chemical reagent may cleave at a specific amino acid residue (e.g., cyanogen bromide hydrolyzes peptide bonds at the C-terminus of methionine residues). Chemical reagents for fragmenting polypeptides or proteins into smaller peptides include cyanogen bromide (CNBr), hydroxylamine, hydrazine, formic acid, BNPS-skatole [2-(2-nitrophenylsulfenyl)-3-methylindole], iodosobenzoic acid, •NTCB+Ni (2-nitro-5-thiocyanobenzoic acid), etc.

In certain embodiments, following enzymatic or chemical cleavage, the resulting peptide fragments are approximately the same desired length, e.g., from about 10 amino acids to about 70 amino acids, from about 10 amino acids to about 60 amino acids, from about 10 amino acids to about 50 amino acids, about 10 to about 40 amino acids, from about 10 to about 30 amino acids, from about 20 amino acids to about 70 amino acids, from about 20 amino acids to about 60 amino acids, from about 20 amino acids to about 50 amino acids, about 20 to about 40 amino acids, from about 20 to about 30 amino acids, from about 30 amino acids to about 70 amino acids, from about 30 amino acids to about 60 amino acids, from about 30 amino acids to about 50 amino acids, or from about 30 amino acids to about 40 amino acids. A cleavage reaction may be monitored, preferably in real time, by spiking the protein or polypeptide sample with a short test FRET (fluorescence resonance energy transfer) peptide comprising a peptide sequence containing a proteinase or endopeptidase cleavage site. In the intact FRET peptide, a fluorescent group and a quencher group are attached to either end of the peptide sequence containing the cleavage site, and fluorescence resonance energy transfer between the quencher and the fluorophore leads to low fluorescence. Upon cleavage of the test peptide by a protease or endopeptidase, the quencher and fluorophore are separated giving a large increase in fluorescence. A cleavage reaction can be stopped when a certain fluorescence intensity is achieved, allowing a reproducible cleavage endpoint to be achieved.

In some aspects, a sample of macromolecules (e.g., peptides, polypeptides, or proteins) can undergo protein fractionation methods where proteins or peptides are separated by one or more properties such as cellular location, molecular weight, hydrophobicity, isoelectric point, or protein enrichment methods. In some embodiments, a subset of macromolecules (e.g., proteins) within a sample is fractionated such that a subset of the macromolecules is sorted from the rest of the sample. For example, the sample may undergo fractionation methods prior to attachment to a support. Alternatively, or additionally, protein enrichment methods may be used to select for a specific protein or peptide (see, e.g., Whiteaker et al., 2007, Anal. Biochem. 362:44-54, incorporated by reference in its entirety) or to select for a particular post translational modification (see, e.g., Huang et al., 2014. J. Chromatogr. A 1372:1-17, incorporated by reference in its entirety). Alternatively, a particular class or classes of proteins such as immunoglobulins, or immunoglobulin (Ig) isotypes such as IgG, can be affinity enriched or selected for analysis. In the case of immunoglobulin molecules, analysis of the sequence and abundance or frequency of hypervariable sequences involved in affinity binding are of particular interest, particularly as they vary in response to disease progression or correlate with healthy, immune, and/or or disease phenotypes. Overly abundant proteins can also be subtracted from the sample using standard immunoaffinity methods. Depletion of abundant proteins can be useful for plasma samples where over 80% of the protein constituent is albumin and immunoglobulins. Several commercial products are available for depletion of plasma samples of overly abundant proteins, including depletion spin columns that remove top 2-20 plasma proteins (Pierce, Agilent), or PROTIA and PROT20 (Sigma-Aldrich).

In certain embodiments, a protein sample dynamic range can be modulated by fractionating the protein sample using standard fractionation methods, including electrophoresis and liquid chromatography (Zhou et al., 2012, Anal Chem 84(2): 720-734), or partitioning the fractions into compartments (e.g., droplets) loaded with limited capacity protein binding beads/resin (e.g. hydroxylated silica particles) (McCormick, 1989, Anal Biochem 181(1): 66-74) and eluting bound protein. Excess protein in each compartmentalized fraction is washed away. Examples of electrophoretic methods include capillary electrophoresis (CE), capillary isoelectric focusing (CIEF), capillary isotachophoresis (CITP), free flow electrophoresis, gel-eluted liquid fraction entrapment electrophoresis (GELFrEE). Examples of liquid chromatography protein separation methods include reverse phase (RP), ion exchange (IE), size exclusion (SE), hydrophilic interaction, etc. Examples of compartment partitions include emulsions, droplets, microwells, physically separated regions on a flat substrate, etc. Exemplary protein binding beads/resins include silica nanoparticles derivatized with phenol groups or hydroxyl groups (e.g., StrataClean Resin from Agilent Technologies, RapidClean from LabTech, etc.). By limiting the binding capacity of the beads/resin, highly-abundant proteins eluting in a given fraction will only be partially bound to the beads, and excess proteins removed.

In some embodiments, a partition barcode is used which comprises assignment of a unique barcode to a subsampling of macromolecules from a population of macromolecules within a sample. This partition barcode may be comprised of identical barcodes arising from the partitioning of macromolecules within compartments labeled with the same barcode (e.g., a barcoded bead population in which multiple beads share the same barcode). The use of physical compartments effectively subsamples the original sample to provide assignment of partition barcodes. For instance, a set of beads labeled with 10,000 different compartment barcodes is provided. Furthermore, suppose in a given assay, that a population of 1 million beads are used in the assay. On average, there are 100 beads per compartment barcode (Poisson distribution). Further suppose that the beads capture an aggregate of 10 million macromolecules. On average, there are 10 macromolecules per bead, with 100 compartments per compartment barcode, there are effectively 1,000 macromolecules per partition barcode (comprised of 100 compartment barcodes for 100 distinct physical compartments).

In another embodiment, single molecule partitioning and partition barcoding of polypeptides is accomplished by labeling polypeptides (chemically or enzymatically) with an amplifiable DNA UMI tag (e.g., recording tag) at the N or C terminus, or both. DNA tags are attached to the body of the polypeptide (internal amino acids) via non-specific photo-labeling or specific chemical attachment to reactive amino acids such as lysines. Information from the recording tag attached to the terminus of the peptide is transferred to the DNA tags via an enzymatic emulsion PCR (Williams et al., Nat Methods, (2006) 3(7):545-550; Schutze et al., Anal Biochem. (2011) 410(1):155-157) or emulsion in vitro transcription/reverse transcription (IVT/RT) step. In the preferred embodiment, a nanoemulsion is employed such that, on average, there is fewer than a single polypeptide per emulsion droplet with size from 50 nm-1000 nm (Nishikawa et al., J Nucleic Acids. (2012) 2012: 923214; Gupta et al., Soft Matter. (2016) 12(11):2826-41; Sole et al., Langmuir (2006, 22(20):8326-8332). Additionally, all the components of PCR are included in the aqueous emulsion mix including primers, dNTPs, Mg2+, polymerase, and PCR buffer. If IVT/RT is used, then the recording tag is designed with a T7/SP6 RNA polymerase promoter sequence to generate transcripts that hybridize to the DNA tags attached to the body of the polypeptide (Ryckelynck et al., RNA. (2015) 21(3):458-469). A reverse transcriptase (RT) copies the information from the hybridized RNA molecule to the DNA tag. In this way, emulsion PCR or IVT/RT can be used to effectively transfer information from the terminus recording tag to multiple DNA tags attached to the body of the polypeptide.

In some embodiments, a sample of macromolecule targets (e.g., peptides, polypeptides, or proteins) can be processed into a physical area or volume e.g., into a compartment. Various processing and/or labeling steps may be performed on the sample. In some embodiments, the compartment separates or isolates a subset of macromolecules from a sample of macromolecules. In some examples, the compartment may be an aqueous compartment (e.g., microfluidic droplet), a solid compartment (e.g., picotiter well or microtiter well on a plate, tube, vial, bead), or a separated region on a surface. In some cases, a compartment may comprise one or more beads to which macromolecules may be immobilized. In some embodiments, macromolecules in a compartment is labeled with a compartment tag including a barcode. For example, the macromolecules in one compartment can be labeled with the same barcode or macromolecules in multiple compartments can be labeled with the same barcode. See e.g., Valihrach et al., Int J Mol Sci. 2018 Mar. 11; 19(3). pii: E807. Encapsulation of cellular contents via gelation in beads is a useful approach to single cell analysis (Tamminen et al., Front Microbiol (2015) 6: 195; Spencer et al., ISME J (2016) 10(2): 427-436). Barcoding single cell droplets enables all components from a single cell to be labeled with the same identifier (Klein et al., Cell (2015) 161(5): 1187-1201; Zilionis et al., Nat Protoc (2017) 12(1): 44-73; International Patent Publication No. WO 2016/130704). Compartment barcoding can be accomplished in a number of ways including direct incorporation of unique barcodes into each droplet by droplet joining (Bio-Rad Laboratories), by introduction of barcoded beads into droplets (10×Genomics), or by combinatorial barcoding of components of the droplet post encapsulation and gelation using and split-pool combinatorial barcoding as described by Gunderson et al. (International Patent Publication No. WO 2016/130704, incorporated by reference in its entirety). A similar combinatorial labeling scheme can also be applied to nuclei (Vitak et al., Nat Methods (2017) 14(3):302-308).

In some embodiments, the macromolecule is joined to a support before contacting with a binding agent. In some cases, it is desirable to use a support with a large carrying capacity to immobilize a large number of macromolecules in a sample. In some embodiments, it is preferred to immobilize the macromolecules using a three-dimensional support (e.g., a porous matrix or a bead). In some examples, the preparation includes joining the macromolecule to nucleic acid molecule or a oligonucleotide prior to or after immobilizing the macromolecule. In some embodiments, a plurality of macromolecules is attached to a support prior to contacting with a binding agent.

A support can be any solid or porous support including, but not limited to, a bead, a microbead, an array, a glass surface, a silicon surface, a plastic surface, a filter, a membrane, a PTFE membrane, nylon, a microtiter well, an ELISA plate, a spinning interferometry disc, a nitrocellulose membrane, a nitrocellulose-based polymer surface, a nanoparticle, or a microsphere. Materials for a support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, silica, polyanhydrides, polyglycolic acid, polyvinylchloride, polylactic acid, polyorthoesters, functionalized silane, polypropylfumerate, collagen, glycosaminoglycans, polyamino acids, or any combination thereof. In certain embodiments, a support is a bead, for example, a polystyrene bead, a polymer bead, a polyacrylate bead, an agarose bead, a cellulose bead, a dextran bead, an acrylamide bead, a solid core bead, a porous bead, a paramagnetic bead, a glass bead, a silica-based bead, or a controlled pore bead or any combinations thereof. In some specific embodiments, the support is a porous agarose bead.

In some embodiments, the support may comprise any suitable solid material, including porous and non-porous materials, to which a macromolecule, e.g., a polypeptide, can be associated directly or indirectly, by any means known in the art, including covalent and non-covalent interactions, or any combination thereof. A support may be two-dimensional (e.g., planar surface) or three-dimensional (e.g., gel matrix or bead). A support can be any support surface including, but not limited to, a bead, a microbead, an array, a glass surface, a silicon surface, a plastic surface, a filter, a membrane, a PTFE membrane, a PTFE membrane, a nitrocellulose membrane, a nitrocellulose-based polymer surface, nylon, a microtiter well, an ELISA plate, a spinning interferometry disc, a polymer matrix, a nanoparticle, or a microsphere. Materials for a support include but are not limited to acrylamide, agarose, cellulose, dextran, nitrocellulose, glass, gold, quartz, polystyrene, polyethylene vinyl acetate, polypropylene, polyester, polymethacrylate, polyacrylate, polyethylene, polyethylene oxide, polysilicates, polycarbonates, poly vinyl alcohol (PVA), Teflon, fluorocarbons, nylon, silicon rubber, polyanhydrides, polyglycolic acid, polyvinylchloride, polylactic acid, polyorthoesters, functionalized silane, polypropylfumerate, collagen, glycosaminoglycans, polyamino acids, dextran, or any combination thereof. Supports further include thin film, membrane, bottles, dishes, fibers, woven fibers, shaped polymers such as tubes, particles, beads, microspheres, microparticles, or any combination thereof. For example, when solid surface is a bead, the bead can include, but is not limited to, a ceramic bead, a polystyrene bead, a polymer bead, a polyacrylate bead, a methylstyrene bead, an agarose bead, a cellulose bead, a dextran bead, an acrylamide bead, a solid core bead, a porous bead, a paramagnetic bead, a glass bead, or a controlled pore bead, a silica-based bead, or any combinations thereof. A bead may be spherical or an irregularly shaped. A bead or support may be porous. A bead's size may range from nanometers, e.g., 100 nm, to millimeters, e.g., 1 mm. In certain embodiments, beads range in size from about 0.2 micron to about 200 microns, or from about 0.5 micron to about 5 micron. In some embodiments, beads can be about 1, 1.5, 2, 2.5, 2.8, 3, 3.5, 4, 4.5, 5, 5.5, 6, 6.5, 7, 7.5, 8, 8.5, 9, 9.5, 10, 10.5, 15, or 20 μm in diameter. In certain embodiments, "a bead" support may refer to an individual bead or a plurality of beads. In some embodiments, the solid surface is a nanoparticle. In certain embodiments, the nanoparticles range in size from about 1 nm to about 500 nm in diameter, for example, between about 1 nm and about 20 nm, between about 1 nm and about 50 nm, between about 1 nm and about 100 nm, between about 10 nm and about 50 nm, between about 10 nm and about 100 nm, between about 10 nm and about 200 nm, between about 50 nm and about 100 nm, between about 50 nm and about 150, between about 50 nm and about 200 nm, between about 100 nm and about 200 nm, or between about 200 nm and about 500 nm in diameter. In some embodiments, the nanoparticles can be about 10 nm, about 50 nm, about 100 nm, about 150 nm, about 200 nm, about 300 nm, or about 500 nm in diameter. In some embodiments, the nanoparticles are less than about 200 nm in diameter.

Various reactions may be used to attach the macromolecules to a support (e.g., a solid or a porous support The macromolecules may be attached directly or indirectly to the support. In some cases, the macromolecules are attached to the support via a nucleic acid. Exemplary reactions include the copper catalyzed reaction of an azide and alkyne to form a triazole (Huisgen 1, 3-dipolar cycloaddition), strain-promoted azide alkyne cycloaddition (SPAAC), reaction of a diene and dienophile (Diels-Alder), strain-promoted alkyne-nitrone cycloaddition, reaction of a strained alkene with an azide, tetrazine or tetrazole, alkene and azide [3+2] cycloaddition, alkene and tetrazine inverse electron demand Diels-Alder (IEDDA) reaction (e.g., m-tetrazine (mTet) or phenyl tetrazine (pTet) and trans-cyclooctene (TCO)); or pTet and an alkene), alkene and tetrazole photoreaction, Staudinger ligation of azides and phosphines, and various displacement reactions, such as displacement of a leaving group by nucleophilic attack on an electrophilic atom (Horisawa 2014, Knall, Hollauf et al. 2014). Exemplary displacement reactions include reaction of an amine with: an activated ester; an N-hydroxysuccinimide ester; an isocyanate; an isothioscyanate, an aldehyde, an epoxide, or the like. In some embodiments, iEDDA click chemistry is used for immobilizing macromolecules (e.g., polypeptides) to a support since it is rapid and delivers high yields at low input concentrations. In another embodiment, m-tetrazine rather than tetrazine is used in an iEDDA click chemistry reaction, as m-tetrazine has improved bond stability. In another embodiment, phenyl tetrazine (pTet) is used in an iEDDA click chemistry reaction. In one case, a polypeptide is labeled with a bifunctional click chemistry reagent, such as alkyne-NHS ester (acetylene-PEG-NETS ester) reagent or alkyne-benzophenone to generate an alkyne-labeled polypeptide. In some embodiments, an alkyne can also be a strained alkyne, such as cyclooctynes including Dibenzocyclooctyl (DBCO), etc.

In certain embodiments where multiple macromolecules are immobilized on the same support, the macromolecules can be spaced appropriately to accommodate the analysis steps to be used to assess the target. For example, it may be advantageous to space the macromolecules that optimally to allow a nucleic acid-based method for assessing and sequencing the proteins to be performed. In some cases, spacing of the macromolecules on the support is determined based on the consideration that information transfer from an adaptor molecule hybridized to the coding tag of a binding agent bound to one immobilized macromolecule may reach a neighboring macromolecule.

In some embodiments, the surface of the support is passivated (blocked). A "passivated" surface refers to a surface that has been treated with outer layer of material. Methods of passivating surfaces include standard methods from the fluorescent single molecule analysis literature, including passivating surfaces with polymer like polyethylene glycol (PEG) (Pan et al., 2015, Phys. Biol. 12:045006), polysiloxane (e.g., Pluronic F-127), star polymers (e.g., star PEG) (Groll et al., 2010, Methods Enzymol. 472:1-18), hydrophobic dichlorodimethylsilane (DDS)+self-assembled Tween-20 (Hua et al., 2014, Nat. Methods 11:1233-1236), diamond-like carbon (DLC), DLC+PEG (Stavis et al., 2011, Proc. Natl. Acad. Sci. USA 108:983-988), and zwitterionic moiety (e.g., U.S. Patent Application Publication US 2006/0183863). In addition to covalent surface modifications, a number of passivating agents can be employed as well including surfactants like Tween-20, polysiloxane in solution (Pluronic series), poly vinyl alcohol (PVA), and proteins like BSA and casein. Alternatively, density of macromolecules (e.g., proteins, polypeptide, or peptides) can be titrated on the surface or within the volume of a solid substrate by spiking a competitor or "dummy" reactive molecule when immobilizing the proteins, polypeptides or peptides to the solid substrate.

To control spacing of the immobilized targets on the support, the density of functional coupling groups for attaching the target (e.g., TCO or carboxyl groups (COOH)) may be titrated on the substrate surface. In some embodiments, multiple target molecules (e.g., macromolecules) are spaced apart on the surface or within the volume (e.g., porous supports) of a support such that adjacent molecules are spaced apart at a distance of about 50 nm to about 500 nm, or about 50 nm to about 400 nm, or about 50 nm to about 300 nm, or about 50 nm to about 200 nm, or about 50 nm to about 100 nm. In some embodiments, multiple molecules are spaced apart on the surface of a support with an average distance of at least 50 nm, at least 60 nm, at least 70 nm, at least 80 nm, at least 90 nm, at least 100 nm, at least 150 nm, at least 200 nm, at least 250 nm, at least 300 nm, at least 350 nm, at least 400 nm, at least 450 nm, or at least 500 nm. In some embodiments, multiple molecules are spaced apart on the surface of a support with an average distance of at least 50 nm. In some embodiments, molecules are spaced apart on the surface or within the volume of a support such that, empirically, the relative frequency of inter- to intra-molecular events (e.g. transfer of information) is <1:10; <1:100; <1:1,000; or <1:10,000.

In some embodiments, the plurality of macromolecules is coupled on the support spaced apart at an average distance between two adjacent molecules which ranges from about 50 to 100 nm, from about 50 to 250 nm, from about 50 to 500 nm, from about 50 to 750 nm, from about 50 to 1,000 nm, from about 50 to 1,500 nm, from about 50 to 2,000 nm, from about 100 to 250 nm, from about 100 to 500 nm, from about 200 to 500 nm, from about 300 to 500 nm, from about 100 to 1000 nm, from about 500 to 600 nm, from about 500 to 700 nm, from about 500 to 800 nm, from about 500 to 900 nm, from about 500 to 1,000 nm, from about 500 to 2,000 nm, from about 500 to 5,000 nm, from about 1,000 to 5,000 nm, or from about 3,000 to 5,000 nm.

In some embodiments, appropriate spacing of the macromolecules on the support is accomplished by titrating the ratio of available attachment molecules on the substrate surface. In some examples, the substrate surface (e.g., bead surface) is functionalized with a carboxyl group (COOH)

which is treated with an activating agent (e.g., activating agent is EDC and Sulfo-NHS). In some examples, the substrate surface (e.g., bead surface) comprises NHS moieties. In some embodiments, a mixture of $mPEG_n$-$NH_2$ and $NH_2$-$PEG_n$-mTet is added to the activated beads (wherein n is any number, such as 1-100). The ratio between the $mPEG_3$-$NH_2$ (not available for coupling) and $NH_2$-$PEG_{24}$-mTet (available for coupling) is titrated to generate an appropriate density of functional moieties available to attach the polypeptides on the substrate surface. In certain embodiments, the mean spacing between coupling moieties (e.g., $NH_2$-$PEG_4$-mTet) on the solid surface is at least 50 nm, at least 100 nm, at least 250 nm, or at least 500 nm. In some specific embodiments, the ratio of $NH_2$-$PEG_n$-mTet to $mPEG_3$-$NH_2$ is about or greater than 1:1000, about or greater than 1:10,000, about or greater than 1:100,000, or about or greater than 1:1,000,000. In some further embodiments, the recording tag attaches to the $NH_2$-$PEG_n$-mTet. In some embodiments, the spacing of the macromolecules on the support is achieved by controlling the concentration and/or number of available COOH or other functional groups on the support.

B. Cleavage

In some embodiments, the provided methods further include removing a portion of the macromolecule following information transfer. The removal of a portion of the macromolecule exposes a new portion of the macromolecule for analysis, e.g., available for binding by a binding agent provided in the next cycle of analysis. If a polypeptide is being analyzed, the methods may include removal of a portion of the polypeptide that includes one or more amino acids (e.g., terminal amino acid). In embodiments relating to methods of analyzing peptides or polypeptides using a degradation based approach, following contacting and binding of a first binding agent to an n NTAA of a peptide of n amino acids, and transferring of the coding tag information to a nucleic acid associated with the peptide thereby generating a first order extended nucleic acid (e.g., on the recording tag), the n NTAA is eliminated. Removal of the n labeled NTAA by contacting with an enzyme or chemical reagents converts the n−1 amino acid of the peptide to an N-terminal amino acid, which is referred to herein as an n−1 NTAA. A second binding agent is contacted with the peptide or polypeptides and binds to the n−1 NTAA, and the second binding agent's information is transferred from the coding tag to the first order extended nucleic acid thereby generating a second order extended nucleic acid (e.g., for generating a concatenated $n^{th}$ order extended nucleic acid representing the peptide). Elimination of the n−1 labeled NTAA converts the n−2 amino acid of the peptide or polypeptides to an N-terminal amino acid, which is referred to herein as n−2 NTAA. Additional binding, transferring information, and removal, can occur as described above up to n amino acids to generate an $n^{th}$ order extended nucleic acid or n separate extended nucleic acids, which collectively represent the peptide or polypeptides. As used herein, an n "order" when used in reference to a binding agent, coding tag, or extended nucleic acid, refers to the n binding cycle, wherein the binding agent and its associated coding tag is used or the n binding cycle where the extended nucleic acid is created (e.g. on recording tag). In some embodiments, steps including the NTAA in the described exemplary approach can be performed instead with a C terminal amino acid (CTAA).

In certain embodiments relating to analyzing peptides or polypeptides, the terminal amino acid is removed or cleaved from the peptide or polypeptides to expose a new terminal amino acid. A portion of the polypeptide for removal can be a labeled (e.g., chemically labeled or modified) portion of the polypeptide. In some embodiments, the terminal amino acid is an NTAA. In other embodiments, the terminal amino acid is a CTAA. Cleavage of a terminal amino acid can be accomplished by any number of known techniques, including chemical cleavage and enzymatic cleavage. In some embodiments, an engineered enzyme that catalyzes or reagent that promotes the removal of a labeled (e.g., chemically labeled or modified)N-terminal amino acid is used. In some embodiments, the terminal amino acid is removed or eliminated using any of the methods as described in International Patent Publication No. WO 2019/089846 and International Patent Application No. PCT/US2020/29969 and PCT/US2020/24521.

In some embodiments, the reagent for removing a terminal amino acid includes a carboxypeptidase or an aminopeptidase or a variant, mutant, or modified protein thereof a hydrolase or a variant, mutant, or modified protein thereof; a mild Edman degradation reagent; an Edmanase enzyme; anhydrous TFA, a base; or any combination thereof. In some embodiments, the mild Edman degradation uses a dichloro or monochloro acid; the mild Edman degradation uses TFA, TCA, or DCA; or the mild Edman degradation uses triethylamine, triethanolamine, or triethylammonium acetate ($Et_3NHOAc$).

In some cases, the reagent for removing the amino acid comprises a base. In some embodiments, the base is a hydroxide, an alkylated amine, a cyclic amine, a carbonate buffer, trisodium phosphate buffer, or a metal salt. In some examples, the hydroxide is sodium hydroxide; the alkylated amine is selected from methylamine, ethylamine, propylamine, dimethylamine, diethylamine, dipropylamine, trimethylamine, triethylamine, tripropylamine, cyclohexylamine, benzylamine, aniline, diphenylamine, N,N-Diisopropylethylamine (DIPEA), and lithium diisopropylamide (LDA); the cyclic amine is selected from pyridine, pyrimidine, imidazole, pyrrole, indole, piperidine, prolidine, 1,8-diazabicyclo[5.4.0]undec-7-ene (DBU), and 1,5-diazabicyclo[4.3.0]non-5-ene (DBN); the carbonate buffer comprises sodium carbonate, potassium carbonate, calcium carbonate, sodium bicarbonate, potassium bicarbonate, or calcium bicarbonate; the metal salt comprises silver; or the metal salt is $AgClO_4$.

In some embodiments, the provided methods include cleavage of an N-terminal amino acid if it is modified by a group such as PTC, modified-PTC, Cbz, DNP, SNP, acetyl, guanidinyl, diheterocyclic methanimine, etc. Enzymatic cleavage of a NTAA may be accomplished by an aminopeptidase or other peptidases. Aminopeptidases naturally occur as monomeric and multimeric enzymes, and may be metal or ATP-dependent. Natural aminopeptidases have very limited specificity, and generically cleave N-terminal amino acids in a processive manner, cleaving one amino acid off after another. For the methods described here, aminopeptidases (e.g., metalloenzymatic aminopeptidase) may be engineered to possess specific binding or catalytic activity to the NTAA only when modified with an N-terminal label. In this way, the aminopeptidase cleaves only a single amino acid at a time from the N-terminus, and allows control of the degradation cycle. In some embodiments, the modified aminopeptidase is non-selective as to amino acid residue identity while being selective for the N-terminal label. In other embodiments, the modified aminopeptidase is selective for both amino acid residue identity and the N-terminal label. Engineered aminopeptidase mutants that bind to and cleave individual or small groups of labelled (biotinylated) NTAAs have been described (see, PCT Publication No. WO2010/065322).

Engineered aminopeptidase mutants that bind to and cleave individual or small groups of labeled (biotinylated) NTAAs have been described (see, PCT Publication No. WO2010/065322, incorporated by reference in its entirety). Aminopeptidases are enzymes that cleave amino acids from the N-terminus of proteins or peptides. Natural aminopeptidases have very limited specificity, and generically eliminate N-terminal amino acids in a processive manner, cleaving one amino acid off after another (Kishor et al., 2015, Anal. Biochem. 488:6-8). However, residue specific aminopeptidases have been identified (Eriquez et al., J. Clin. Microbiol. 1980, 12:667-71; Wilce et al., 1998, Proc. Natl. Acad. Sci. USA 95:3472-3477; Liao et al., 2004, Prot. Sci. 13:1802-10). Control of the stepwise degradation of the N-terminus of the peptide can be achieved by using engineered aminopeptidases that are only active (e.g., binding activity or catalytic activity) in the presence of the label. In certain embodiments, the aminopeptidase may be engineered to be non-specific, such that it does not selectively recognize one particular amino acid over another, but rather just recognizes the labeled N-terminus. In yet another embodiment, cyclic cleavage is attained by using an engineered acylpeptide hydrolase (APH) to cleave an acetylated NTAA. In yet another embodiment, amidination (guanidinylation) of the NTAA is employed to enable mild cleavage of the labeled NTAA using NaOH (Hamada, (2016) Bioorg Med Chem Lett 26(7): 1690-1695).

In some embodiments, the method further comprises contacting the polypeptide with a proline aminopeptidase under conditions suitable to cleave an N-terminal proline before step (b). In some examples, a proline aminopeptidase (PAP) is an enzyme that is capable of specifically cleaving an N-terminal proline from a polypeptide. PAP enzymes that cleave N-terminal prolines are also referred to as proline iminopeptidases (PIPs). Known monomeric PAPs include family members from *B. coagulans, L. delbrueckii, N. gonorrhoeae, F. meningosepticum, S. marcescens, T. acidophilum, L. plantarum* (MEROPS 533.001) Nakajima et al., J Bacteriol. (2006) 188(4):1599-606; Kitazono et al., Bacteriol (1992) 174(24):7919-7925). Known multimeric PAPs including *D. hansenii* (Bolumar et al., (2003) 86(1-2):141-151) and similar homologues from other species (Basten et al., Mol Genet Genomics (2005) 272(6):673-679). Either native or engineered variants/mutants of PAPs may be employed.

For embodiments relating to CTAA binding agents, methods of cleaving CTAA from peptides or polypeptides are also known in the art. For example, U.S. Pat. No. 6,046,053 discloses a method of reacting the peptide or protein with an alkyl acid anhydride to convert the carboxy-terminal into oxazolone, liberating the C-terminal amino acid by reaction with acid and alcohol or with ester. Enzymatic cleavage of a CTAA may also be accomplished by a carboxypeptidase. Several carboxypeptidases exhibit amino acid preferences, e.g., carboxypeptidase B preferentially cleaves at basic amino acids, such as arginine and lysine. As described above, carboxypeptidases may also be modified in the same fashion as aminopeptidases to engineer carboxypeptidases that specifically bind to CTAAs having a C-terminal label. In this way, the carboxypeptidase cleaves only a single amino acid at a time from the C-terminus, and allows control of the degradation cycle. In some embodiments, the modified carboxypeptidase is non-selective as to amino acid residue identity while being selective for the C-terminal label. In other embodiments, the modified carboxypeptidase is selective for both amino acid residue identity and the C-terminal label.

C. Analysis

In some embodiments, the extended recording tag generated from performing the provided methods comprises information transferred from one or more coding tags. In some embodiments, the extended recording tags comprises a series of information transferred from a plurality of coding tags indicative of the order of binding by the binding agents. This extended recording tag can be analyzed by any suitable methods. In some embodiments, the extended recording tags (or a portion thereof) are amplified prior to determining at least the sequence of the coding tag(s) in the extended recording tag. In some embodiments, the extended recording tags (or a portion thereof) are released prior to determining at least the sequence of the coding tag(s) in the extended recording tag.

The length of the final extended recording tag generated by the methods described herein is dependent upon multiple factors, including the length of the coding tag(s) (e.g., barcode and spacer), the length of the nucleic acids (e.g., optionally including any unique molecular identifier, spacer, universal priming site, barcode, or combinations thereof). After transfer of the final tag information to the extended nucleic acid (e.g., from any coding tags), the tag can be capped by addition of a universal reverse priming site via ligation, primer extension or other methods known in the art. In some embodiments, the universal forward priming site in the nucleic acid (e.g., on the recording tag) is compatible with the universal reverse priming site that is appended to the final extended nucleic acid. In some embodiments, a universal reverse priming site is an Illumina P7 primer or an Illumina P5 primer. The sense or antisense P7 may be appended, depending on strand sense of the nucleic acid to which the identifying information from the coding tag is transferred to. An extended nucleic acid library can be cleaved or amplified directly from the support (e.g., beads) and used in traditional next generation sequencing assays and protocols.

In some embodiments, a primer extension reaction is performed on a library of single stranded extended nucleic acids (e.g., extended on the recording tag) to copy complementary strands thereof. In some embodiments, the peptide sequencing assay (e.g., ProteoCode assay), comprises several chemical and enzymatic steps in a cyclical progression.

Extended nucleic acids recording tags can be processed and analysed using a variety of nucleic acid sequencing methods. In some embodiments, extended recording tags containing the information from one or more coding tags and any other nucleic acid components are processed and analysed. In some embodiments, the collection of extended recording tags can be concatenated. In some embodiments, the extended recording tag can be amplified prior to determining the sequence.

Examples of sequencing methods include, but are not limited to, chain termination sequencing (Sanger sequencing); next generation sequencing methods, such as sequencing by synthesis, sequencing by ligation, sequencing by hybridization, polony sequencing, ion semiconductor sequencing, and pyrosequencing; and third generation sequencing methods, such as single molecule real time sequencing, nanopore-based sequencing, duplex interrupted sequencing, and direct imaging of DNA using advanced microscopy.

Suitable sequencing methods for use in the invention include, but are not limited to, sequencing by hybridization, sequencing by synthesis technology (e.g., HiSeq™ and Solexa™, Illumina), SMRT™ (Single Molecule Real Time) technology (Pacific Biosciences), true single molecule sequencing (e.g., HeliScope™, Helicos Biosciences), massively parallel next generation sequencing (e.g., SOLiD™, Applied Biosciences; Solexa and HiSeg™ Illumina), massively parallel semiconductor sequencing (e.g., Ion Torrent), pyrosequencing technology (e.g., GS FLX and GS Junior Systems, Roche/454), nanopore sequence (e.g., Oxford Nanopore Technologies).

A library of nucleic acids (e.g., extended nucleic acids) may be amplified in a variety of ways. A library of nucleic acids (e.g., recording tags comprising information from one or more coding tags) undergo exponential amplification, e.g., via PCR or emulsion PCR. Emulsion PCR is known to produce more uniform amplification (Hori, Fukano et al., Biochem Biophys Res Commun (2007) 352(2): 323-328). Alternatively, a library of nucleic acids (e.g., extended nucleic acids) may undergo linear amplification, e.g., via in vitro transcription of template DNA using T7 RNA polymerase. The library of nucleic acids (e.g., extended nucleic acids) can be amplified using primers compatible with the universal forward priming site and universal reverse priming site contained therein. A library of nucleic acids (e.g., the recording tag) can also be amplified using tailed primers to add sequence to either the 5'-end, 3'-end or both ends of the extended nucleic acids. Sequences that can be added to the termini of the extended nucleic acids include library specific index sequences to allow multiplexing of multiple libraries in a single sequencing run, adaptor sequences, read primer sequences, or any other sequences for making the library of extended nucleic acids compatible for a sequencing platform. An example of a library amplification in preparation for next generation sequencing is as follows: a 20 μl PCR reaction volume is set up using an extended nucleic acid library eluted from ~1 mg of beads (~10 ng), 200 μM dNTP, 1 μM of each forward and reverse amplification primers, 0.5 μl (1U) of Phusion Hot Start enzyme (New England Biolabs) and subjected to the following cycling conditions: 98° C. for 30 sec followed by 20 cycles of 98° C. for 10 sec, 60° C. for 30 sec, 72° C. for 30 sec, followed by 72° C. for 7 min, then hold at 4° C.

In certain embodiments, either before, during or following amplification, the library of nucleic acids (e.g., extended nucleic acids) can undergo target enrichment. In some embodiments, target enrichment can be used to selectively capture or amplify extended nucleic acids representing macromolecules (e.g., polypeptides) of interest from a library of extended nucleic acids before sequencing. In some aspects, target enrichment for protein sequencing is challenging because of the high cost and difficulty in producing highly-specific binding agents for target proteins. In some cases, antibodies are notoriously non-specific and difficult to scale production across thousands of proteins. In some embodiments, the methods of the present disclosure circumvent this problem by converting the protein code into a nucleic acid code which can then make use of a wide range of targeted DNA enrichment strategies available for DNA libraries. In some cases, peptides of interest can be enriched in a sample by enriching their corresponding extended nucleic acids. Methods of targeted enrichment are known in the art, and include hybrid capture assays, PCR-based assays such as TruSeq custom Amplicon (Illumina), padlock probes (also referred to as molecular inversion probes), and the like (see, Mamanova et al., (2010) Nature Methods 7: 111-118; Bodi et al., J. Biomol. Tech. (2013) 24:73-86; Ballester et al., (2016) Expert Review of Molecular Diagnostics 357-372; Mertes et al., (2011) Brief Funct. Genomics 10:374-386; Nilsson et al., (1994) Science 265:2085-8; each of which are incorporated herein by reference in their entirety).

In one embodiment, a library of nucleic acids (e.g., extended recording tags) is enriched via a hybrid capture-based assay. In a hybrid-capture based assay, the library of extended nucleic acids is hybridized to target-specific oligonucleotides that are labeled with an affinity tag (e.g., biotin). Extended nucleic acids hybridized to the target-specific oligonucleotides are "pulled down" via their affinity tags using an affinity ligand (e.g., streptavidin coated beads), and background (non-specific) extended nucleic acids are washed away. The enriched extended nucleic acids (e.g., extended nucleic acids) are then obtained for positive enrichment (e.g., eluted from the beads). In some embodiments, oligonucleotides complementary to the corresponding extended nucleic acid library representations of peptides of interest can be used in a hybrid capture assay. In some embodiments, sequential rounds or enrichment can also be carried out, with the same or different bait sets.

In another embodiment, primer extension and ligation-based mediated amplification enrichment (AmpliSeq, PCR, TruSeq TSCA, etc.) can be used to select and module fraction enriched of library elements representing a subset of polypeptides. Competing oligonucleotides can also be employed to tune the degree of primer extension, ligation, or amplification. In the simplest implementation, this can be accomplished by having a mix of target specific primers comprising a universal primer tail and competing primers lacking a 5' universal primer tail. After an initial primer extension, only primers with the 5' universal primer sequence can be amplified. The ratio of primer with and without the universal primer sequence controls the fraction of target amplified. In other embodiments, the inclusion of hybridizing but non-extending primers can be used to modulate the fraction of library elements undergoing primer extension, ligation, or amplification.

Targeted enrichment methods can also be used in a negative selection mode to selectively remove extended nucleic acids from a library before sequencing. Examples of undesirable extended nucleic acids that can be removed are those representing over abundant polypeptide species, e.g., for proteins, albumin, immunoglobulins, etc.

A competitor oligonucleotide bait, hybridizing to the target but lacking a biotin moiety, can also be used in the hybrid capture step to modulate the fraction of any particular locus enriched. The competitor oligonucleotide bait competes for hybridization to the target with the standard biotinylated bait effectively modulating the fraction of target pulled down during enrichment. The ten orders dynamic range of protein expression can be compressed by several orders using this competitive suppression approach, especially for the overly abundant species such as albumin. Thus, the fraction of library elements captured for a given locus relative to standard hybrid capture can be modulated from 100% down to 0% enrichment.

Additionally, library normalization techniques can be used to remove overly abundant species from the extended nucleic acid library. This approach works best for defined length libraries originating from peptides generated by site-specific protease digestion such as trypsin, LysC, GluC, etc. In one example, normalization can be accomplished by denaturing a double-stranded library and allowing the library elements to re-anneal. The abundant library elements re-anneal more quickly than less abundant elements due to the second-order rate constant of bimolecular hybridization kinetics (Bochman, Paeschke et al. 2012). The ssDNA library elements can be separated from the abundant dsDNA library elements using methods known in the art, such as chromatography on hydroxyapatite columns (VanderNoot, et al., 2012, Biotechniques 53:373-380) or treatment of the library with a duplex-specific nuclease (DSN) from Kamchatka crab (Shagin et al., (2002) Genome Res. 12:1935-42) which destroys the dsDNA library elements.

Any combination of fractionation, enrichment, and subtraction methods, of the polypeptides before attachment to the support and/or of the resulting extended nucleic acid library can economize sequencing reads and improve measurement of low abundance species.

In some embodiments, a library of nucleic acids (e.g., extended nucleic acids) is concatenated by ligation or end-complementary PCR to create a long DNA molecule comprising multiple different extended recorder tags, extended coding tags, or di-tags, respectively (Du et al., (2003) BioTechniques 35:66-72; Muecke et al., (2008) Structure 16:837-841; U.S. Pat. No. 5,834,252, each of which is incorporated by reference in its entirety). This embodiment is preferable for nanopore sequencing in which long strands of DNA are analyzed by the nanopore sequencing device.

In some embodiments, direct single molecule analysis is performed on the nucleic acids (e.g., extended nucleic acids) (see, e.g., Harris et al., (2008) Science 320:106-109). The nucleic acids (e.g., extended nucleic acids) can be analysed directly on the support, such as a flow cell or beads that are compatible for loading onto a flow cell surface (optionally microcell patterned), wherein the flow cell or beads can integrate with a single molecule sequencer or a single molecule decoding instrument. For single molecule decoding, hybridization of several rounds of pooled fluorescently-labeled of decoding oligonucleotides (Gunderson et al., (2004) Genome Res. 14:970-7) can be used to ascertain both the identity and order of the coding tags within the extended nucleic acids (e.g., on the recording tag). In some embodiments, the binding agents may be labeled with cycle-specific coding tags as described above (see also, Gunderson et al., (2004) Genome Res. 14:970-7).

Following sequencing of the nucleic acid libraries (e.g., of extended nucleic acids), the resulting sequences can be collapsed by their UMIs if used and then associated to their corresponding polypeptides and aligned to the totality of the proteome. Resulting sequences can also be collapsed by their compartment tags and associated to their corresponding compartmental proteome, which in a particular embodiment contains only a single or a very limited number of protein molecules. Both protein identification and quantification can easily be derived from this digital peptide information.

The methods disclosed herein can be used for analysis, including detection, quantitation and/or sequencing, of a plurality of macromolecules simultaneously (multiplexing). Multiplexing as used herein refers to analysis of a plurality of macromolecules (e.g. polypeptides) in the same assay. The plurality of macromolecules can be derived from the same sample or different samples. The plurality of macromolecules can be derived from the same subject or different subjects. The plurality of macromolecules that are analyzed can be different macromolecules, or the same macromolecule derived from different samples. A plurality of macromolecules includes 2 or more macromolecules, 5 or more macromolecules, 10 or more macromolecules, 50 or more macromolecules, 100 or more macromolecules, 500 or more macromolecules, 1,000 or more macromolecules, 5,000 or more macromolecules, 10,000 or more macromolecules, 50,000 or more macromolecules, 100,000 or more macromolecules, 500,000 or more macromolecules, or 1,000,000 or more macromolecules.

III. KITS AND ARTICLES OF MANUFACTURE

Provided herein are kits and articles of manufacture comprising components for preforming a macromolecule analysis assay. In some embodiments, the kit includes a binding agent comprising a coding tag which comprises identifying information regarding the binding agent. In some aspects, the kit includes a plurality or set of binding agents each comprising a coding tag. In some embodiment, the binding agent is configured to bind to a macromolecule associated with a recording tag and reagents for transferring information from the coding tag to the recording tag are also provided. Also provided in the kits are a nucleic acid joining reagent, a polymerase, and a double strand nucleic acid cleaving reagent. In some aspects, the nucleic acid joining reagent, polymerase, and double strand nucleic acid cleaving reagent are provided as a mixture. For example, the nucleic acid joining reagent is a chemical or enzymatic ligation reagent. In some cases, the double strand nucleic acid cleaving reagent is a restriction enzyme.

In some embodiments, the kits further contain other reagents for treating and analyzing the target macromolecules (e.g., proteins, polypeptides, or peptides). The kits and articles of manufacture may include any one or more of the reagents and components used in the methods described in Section I and II. In some embodiments, the kit comprises reagents for preparing samples, such as for preparing macromolecules from a sample and joining to a support. In some embodiments, the kits optionally include instructions for performing the macromolecule analysis assay. In some embodiments, the kits comprise one or more of the following components: binding agent(s), nucleic acid joining reagent(s), polymerase(s), double strand nucleic acid cleaving reagent(s), solid support(s), recording tag(s), reagent(s) for transferring information, sequencing reagent(s), and/or any needed buffer(s), etc. The recording tags, binding agents, and coding tags may have particular structure and features as described in Sections IA, IB, and IC, respectively In one aspect, provided herein are components used to prepare a reaction mixture. In some preferred embodiments, the reaction mixture is a solution. In preferred embodiments, the reaction mixture includes one or more of the following: binding agent(s) and associated coding tag(s), solid support(s), recording tag(s), reagent(s) for transferring information including nucleic acid joining reagent(s), polymerase(s), double strand nucleic acid cleaving reagent(s), sequencing reagent(s), buffer(s) and/or other additive(s).

In another aspect, disclosed herein is a kit for performing a macromolecule analysis assay comprising a library of binding agents, wherein each binding agent comprises or is associated with a coding tag. In some aspects, the coding tag comprises identifying information regarding the binding moiety of the binding agent. In some examples, the binding moiety is capable of binding to one or more N-terminal, internal, or C-terminal amino acids of the target peptide or polypeptide, or capable of binding to the one or more N-terminal, internal, or C-terminal amino acids of a peptide modified by a functionalizing/modification reagent.

In some embodiments, the kits and articles of manufacture further comprise a plurality of nucleic acid molecules or oligonucleotides. In some embodiments, the kits include a plurality of barcodes. The barcode(s) may include a compartment barcode, a partition barcode, a sample barcode, a fraction barcode, or any combination thereof. In some cases, the barcode comprises a unique molecule identifier (UMI). In some examples, the barcode comprises a DNA molecule, DNA with pseudo-complementary bases, an RNA molecule, a BNA molecule, an XNA molecule, a LNA molecule, a PNA molecule, a γPNA molecule, a non-nucleic acid sequenceable polymer, e.g., a polysaccharide, a polypeptide, a peptide, or a polyamide, or a combination thereof. In some embodiments, the barcodes are configured to attach the macromolecules for analysis, e.g., the proteins, in the sample or to attach to nucleic components associated with the macromolecules.

In some embodiments, the kit further comprises reagents for treating the macromolecules, e.g., the proteins. Any combination of fractionation, enrichment, and subtraction methods, of the proteins may be performed. For example, the reagent may be used to fragment or digest the proteins. In some cases, the kit comprises reagents and components to fractionate, isolate, subtract, enrich proteins. In some examples, the kits further comprises a protease such as trypsin, LysN, or LysC. In some embodiments, the kit comprises a support for immobilizing the one or more targets and reagents for immobilizing the target on a support. In some embodiments, the kit further includes a reagent for removing the N-terminal amino acid (NTAA) of the polypeptide, such as a chemical agent or an enzymatic agent. In some embodiments, the kit further includes a reagent for modifying the terminal amino acid of the polypeptide, such as a chemical agent or an enzymatic agent.

In some embodiments, the kit also comprises one or more buffers or reaction fluids necessary for performing any of the steps of the macromolecule analysis assay. Buffers including wash buffers, reaction buffers, and binding buffers, elution buffers and the like are known to those or ordinary skill in the arts. In some embodiments, the kits further include buffers and other components to accompany other reagents described herein. The reagents, buffers, and other components may be provided in vials (such as sealed vials), vessels, ampules, bottles, jars, flexible packaging (e.g., sealed Mylar or plastic bags), and the like. Any of the components of the kits may be sterilized and/or sealed.

In some embodiments, the kit includes one or more reagents for nucleic acid sequence analysis. In some examples, the reagent for sequence analysis is for use in sequencing by synthesis, sequencing by ligation, single molecule sequencing, single molecule fluorescent sequencing, sequencing by hybridization, polony sequencing, ion semiconductor sequencing, pyrosequencing, single molecule real-time sequencing, nanopore-based sequencing, or direct imaging of DNA using advanced microscopy, or any combination thereof.

In addition to above-mentioned components, the subject kits may further include instructions for using the components of the kit to practice the subject methods, i.e., instructions for sample preparation, treatment and/or analysis. The kits described herein may also include other materials desirable from a commercial and user standpoint, including other buffers, diluents, filters, syringes, and package inserts with instructions for performing any methods described herein.

Any of the above-mentioned kit components, and any molecule, molecular complex or conjugate, reagent (e.g., chemical or biological reagents), agent, structure (e.g., support, surface, particle, or bead), reaction intermediate, reaction product, binding complex, or any other article of manufacture disclosed and/or used in the exemplary kits and methods, may be provided separately or in any suitable combination in order to form a kit.

IV. EXEMPLARY EMBODIMENTS

Among the provided embodiments are:

1. A method for analyzing a macromolecule, comprising the steps of:
   (a) providing a macromolecule and an associated recording tag joined to a support;
   (b) contacting the macromolecule with a binding agent capable of binding to the macromolecule, wherein the binding agent comprises a coding tag with identifying information regarding the binding agent, to allow binding between the macromolecule and the binding agent;
   (c) joining the 5' end of the recording tag to the 3'end of the coding tag by a nucleic acid joining reagent;
   (d) extending the recording tag using the coding tag as a template by a polymerase, generating a double stranded extended recording tag; and
   (e) cleaving the double stranded extended recording tag with a double strand nucleic acid cleaving reagent to generate a 3' overhang in the extended recording tag;
   whereby information is transferred from the coding tag to the recording tag to generate the extended recording tag.

2. The method of embodiment 1, wherein in step (d), the double stranded extended recording tag comprises a recognition sequence capable of being recognized by the double strand nucleic acid cleaving reagent.

3. The method of embodiment 1 or embodiment 2, wherein the cleavage in step (e) releases the binding agent from the macromolecule.

4. The method of any one of embodiments 1-3, wherein the recording tag and coding tag comprise nucleic acids.

5. The method of any one of embodiments 1-4, wherein the extended recording tag comprises a nucleic acid hairpin.

6. The method of any one of embodiments 1-5, wherein steps (a), (b), (c), (d) and (e) are performed sequentially.

7. The method of any one of embodiments 1-6, wherein steps (b), (c), (d) and (e) are repeated sequentially one or more times in a cyclic manner.

8. The method of any one of embodiments 1-7, wherein the macromolecule is a lipid, a carbohydrate, a protein, a polypeptide or a peptide.

9. The method of embodiment 8, wherein the peptide is obtained by fragmenting a protein from a biological sample.

10. The method of any one of embodiments 1-9, wherein the macromolecule for analysis is not a nucleic acid.

11. The method of any one of embodiments 7-10, further comprising removing a portion of the macromolecule prior to repeating step (b).

12. The method of any one of embodiments 8-11, further comprising removing the N-terminal amino acid (NTAA) of the polypeptide to expose a new NTAA of the polypeptide prior to repeating step (b).

13. The method of any one of embodiments 7-12, wherein the 3' overhang of the extended recording tag generated by the double strand nucleic acid cleaving reagent in step (e) is available to hybridize with a second coding tag when step (b) is repeated.

14. The method of any one of embodiments 1-13, further comprising removing the binding agent.

15. The method of embodiment 14, wherein the binding agent is removed after transferring the information of the coding tag to the recording tag.

16. The method of embodiment 14 or embodiment 15, wherein the binding agent is removed prior to repeating step (b).

17. The method of any one of embodiments 1-16, wherein the method comprises contacting a plurality of macromolecules with a single binding agent or a plurality of binding agents in step (b).

18. The method of any one of embodiments 8-17, further comprising treating the polypeptide with a reagent for modifying a terminal amino acid of the polypeptide.

19. The method of embodiment 18, wherein the reagent for modifying a terminal amino acid of the polypeptide comprises a chemical agent or an enzymatic agent.

20. The method of embodiment 18 or embodiment 19, wherein the polypeptide is treated with the reagent for modifying a terminal amino acid of the polypeptide prior to step (b).

21. The method of any one of embodiments 1-20, wherein the recording tag associated with the macromolecule comprises a double stranded region.

22. The method of embodiment 21, wherein the recording tag associated with the macromolecule comprises a nucleic acid hairpin.

23. The method of any one of embodiments 1-22, wherein the recording tag associated with the macromolecule has a 3' overhang.

24. The method of any one of embodiments 1-23, wherein the recording tag comprises a barcode.

25. The method of any one of embodiments 1-24, wherein the recording tag comprises a unique molecule identifier (UMI).

26. The method of embodiment 24 or embodiment 25, wherein step (a) comprises providing the barcode and/or the UMI to the recording tag.

27. The method of embodiment 24 or embodiment 26, wherein the barcode is a sample barcode, a fraction barcode, spatial barcode, and/or a compartment tag.

28. The method of embodiment 24 or embodiment 25, wherein step (a) comprises using ligation and/or extension to provide the barcode and/or the UMI to the recording tag.

29. The method of any one of embodiments 23-28, wherein step (a) comprises cleaving the recording tag to generate a 3' overhang.

30. The method of any one of embodiments 23-29, wherein the 3' overhang of the recording tag is generated by extension and/or cleavage by a double strand nucleic acid cleaving reagent.

31. The method of any one of embodiments 1-30, wherein the recording tag comprises a universal priming site.

32. The method of embodiment 31, wherein the universal priming site comprises a priming site for amplification, sequencing, or both.

33. The method of any one of embodiments 1-32, wherein steps (c), (d), and (e) are performed as a one-pot reaction.

34. The method of embodiment 33, wherein the nucleic acid joining reagent, the polymerase and the double strand nucleic acid cleaving reagent of steps (c), (d), and (e), respectively, are provided as a mixture.

35. The method of any one of embodiments 1-32, wherein steps (c), (d), and (e) are performed sequentially and separately.

36. The method of any one of embodiments 1-32, wherein the nucleic acid joining reagent of step (c) and the polymerase of step (d) are provided simultaneously.

37. The method of any one of embodiments 1-32, wherein the polymerase of step (d) and the double strand nucleic acid cleaving reagent of step (e) are provided simultaneously.

38. The method of any one of embodiments 1-37, wherein the coding tag comprises a partial restriction enzyme recognition sequence.

39. The method of embodiment 38, wherein the partial restriction enzyme recognition sequence of the coding tag is single stranded.

40. The method of any one of embodiments 1-39, wherein the coding tag comprises a barcode and/or unique molecule identifier (UMI).

41. The method of any one of embodiments 1-40, wherein the recording tag and coding tag each comprises a spacer.

42. The method of embodiment 41, wherein the spacer is a nucleic acid molecule of less than or equal to 10 bases, less than or equal to 9 bases, less than or equal to 8 bases, less than or equal to 7 bases, less than or equal to 6 bases, less than or equal to 5 bases, less than or equal to 4 bases, less than or equal to 3 bases, or less than or equal to 2 bases.

43. The method of embodiment 41 or embodiment 42, wherein the recording tag or extended recording tag comprises a spacer that is the cut site overhang generated by the double strand nucleic acid cleaving reagent.

44. The method of any one of embodiments 41-43, wherein the spacer is a cycle-specific spacer or cycle-alternating spacer.

45. The method of embodiment 44, wherein the method is self-terminating after one cycle of information transfer due to incompatible overhangs.

46. The method of any one of embodiments 41-45, wherein information is transferred from a second coding tag to the extended recording tag if the spacer added by the previous coding tag matches at least a portion of the spacer of the second coding tag.

47. The method of any one of embodiments 1-47, wherein the recording tag and coding tag do not comprise a spacer.

48. The method of any one of embodiments 1-47, wherein the coding tag has a 3' end available for a reaction.

49. The method of embodiment 48, wherein the binding agent is attached to the 5' end of the coding tag.

50. The method of any one of embodiments 1-49, wherein the method comprises one or more wash step(s).

51. The method of embodiment 50, wherein a wash step is performed before step (c).

52. The method of embodiment 50, wherein a wash step is performed before step (d).

53. The method of embodiment 50, wherein a wash step is performed before step (e).

54. The method of any one of embodiments 1-53, wherein the nucleic acid joining reagent is a chemical ligation reagent or an enzymatic ligation reagent.

55. The method of embodiment 54, wherein the enzymatic nucleic acid joining reagent is a ligase.

56. The method of any one of embodiments 1-55, wherein the double strand nucleic acid cleaving reagent is a restriction enzyme.

57. The method of embodiment 55, wherein the restriction enzyme is a type IIS restriction enzyme.

58. The method of embodiment 57, wherein the type IIS restriction enzyme recognizes a sequence of bases that comprises:

```
5'...GCAGTGNN...3'

3'...CGTCACNN...5'.
```

59. The method of embodiment 57 or embodiment 58, wherein the restriction enzyme is Nb.BtsI or BtsI-v2 or a derivative thereof.

60. The method of any one of embodiments 1-59, wherein the ligation, extension, and cleavage of steps (c), (d), and (e), respectively, occurs in a step-wise manner.

61. The method of any one of embodiments 1-60, wherein the binding agent does not remain bound to the macromolecule after the recording tag is joined to the coding tag by the nucleic acid joining reagent.

62. The method of any one of embodiments 1-61, wherein a final information transfer cycle is performed to provide a capping sequence to the extended recording tag, wherein optionally, the capping sequence comprises a universal priming site for amplification, sequencing, or both.

63. The method of embodiment 62, wherein the capping sequence is provided in a coding tag associated with a binding agent that is capable of binding to a universal feature of the macromolecules.

64. The method of embodiment 63, wherein the universal feature is a chemical modification of the N-terminal amino acid of the polypeptide.

65. The method of any one of embodiments 8-64, wherein the extended recoding tag comprises a series of information transferred from a plurality of coding tags.

66. The method of any one of embodiments 1-65, further comprising analyzing one or more of the extended recording tags.

67. The method of embodiment 66, wherein the one or more of the extended recording tags are amplified prior to analysis.

68. The method of embodiment 66 or embodiment 67, wherein analyzing the extended recording tag(s) comprises a nucleic acid sequencing method.

69. The method of embodiment 68, wherein the nucleic acid sequencing method is sequencing by synthesis, sequencing by ligation, sequencing by hybridization, polony sequencing, ion semiconductor sequencing, pyrosequencing, single molecule real-time sequencing, nanopore-based sequencing, or direct imaging of DNA using advanced microscopy.

70. The method of any one of embodiments 1-69, wherein the binding agent is a polypeptide or a protein.

71. The method of embodiment 70, wherein the binding agent is an aminopeptidase or variant, mutant, or modified protein thereof; an aminoacyl tRNA synthetase or variant, mutant, or modified protein thereof; an anticalin or variant, mutant, or modified protein thereof; a ClpS, ClpS2, or variant, mutant, or modified protein thereof; a UBR box protein or variant, mutant, or modified protein thereof; or a modified small molecule that binds amino acid(s), i.e. vancomycin or a variant, mutant, or modified molecule thereof; or an antibody or binding fragment thereof; or any combination thereof.

72. The method of any one of embodiments 8-71, wherein the binding agent binds to a single amino acid residue, a dipeptide, a tripeptide or a post-translational modification of a polypeptide macromolecule.

73. The method of embodiment 72, wherein the binding agent is configured to bind to an N-terminal amino acid residue of the polypeptide.

74. The method of embodiment 73, wherein the binding agent is configured to bind to a chemically modified or labeled N-terminal amino acid residue of the polypeptide.

75. A kit for macromolecule analysis, comprising:
a binding agent comprising a coding tag, which comprises identifying information regarding the binding agent;
a nucleic acid joining reagent;
a polymerase; and
a double strand nucleic acid cleaving reagent;
wherein the binding agent is configured to bind to a macromolecule associated with a recording tag and the identifying information from the coding tag is configured for transfer from the coding tag to the recording tag associated with the macromolecule.

76. The kit of embodiment 75, wherein the macromolecule is a lipid or a carbohydrate.

77. The kit of embodiment 75, wherein the macromolecule is a protein, a polypeptide or a peptide.

78. The kit of embodiment 77, further comprising a reagent for removing the N-terminal amino acid (NTAA) of the polypeptide.

79. The kit of embodiment 78, wherein the reagent for removing the terminal amino acid of the polypeptide comprises a chemical agent or an enzymatic agent.

80. The kit of any one of embodiments 77-79, further comprising a reagent for modifying the terminal amino acid of the polypeptide.

81. The kit of embodiment 80, wherein the reagent for modifying the terminal amino acid of the polypeptide comprises a chemical agent or an enzymatic agent.

82. The kit of any one of embodiments 75-81, wherein the recording tag associated with the macromolecule comprises a double stranded region.

83. The kit of embodiment 82, wherein the recording tag associated with the macromolecule comprises a nucleic acid hairpin.

84. The kit of any one of embodiments 75-83, wherein the recording tag associated with the macromolecule has a 3' overhang.

85. The kit of any one of embodiments 75-84, wherein the recording tag comprises a barcode.

86. The kit of embodiment 85, wherein the barcode is a sample barcode, a fraction barcode, spatial barcode, and/or a compartment tag.

87. The kit of any one of embodiments 75-86, wherein the recording tag comprises a unique molecule identifier (UMI).

88. The kit of any one of embodiments 75-87, wherein the recording tag comprises a universal priming site.

89. The kit of embodiment 88, wherein the universal priming site comprises a priming site for amplification, sequencing, or both.

90. The kit of any one of embodiments 75-89, wherein the kit comprises a mixture comprising the nucleic acid joining reagent, the polymerase and the double strand nucleic acid cleaving reagent.

91. The kit of any one of embodiments 75-90, wherein the coding tag comprises a partial restriction enzyme recognition sequence.

92. The kit of embodiment 91, wherein the partial restriction enzyme recognition sequence of the coding tag is single stranded.

93. The kit of any one of embodiments 75-92, wherein the coding tag comprises a barcode and/or unique molecule identifier (UMI).

94. The kit of any one of embodiments 75-93, wherein the recording tag and coding tag each comprises a spacer.

95. The kit of embodiment 94, wherein the spacer is a nucleic acid molecule of less than or equal to 10 bases, less than or equal to 9 bases, less than or equal to 8 bases, less than or equal to 7 bases, less than or equal to 6 bases, less than or equal to 5 bases, less than or equal to 4 bases, less than or equal to 3 bases, or less than or equal to 2 bases.

96. The kit of embodiment 94 or embodiment 95, wherein the spacer is a cycle-specific spacer or cycle-alternating spacer.

97. The kit of any one of embodiments 75-93, wherein the recording tag and coding tag do not comprise a spacer.

98. The kit of any one of embodiments 75-97, wherein the coding tag has a 3' end available for a reaction.

99. The kit of any one of embodiments 75-98, wherein the enzymatic nucleic acid joining reagent is a ligase.

100. The kit of any one of embodiments 75-99, wherein the double strand nucleic acid cleaving reagent is a restriction enzyme.

101. The kit of embodiment 100, wherein the restriction enzyme is a type IIS restriction enzyme.

102. The kit of embodiment 101, wherein the type IIS restriction enzyme recognizes a sequence of bases that comprises:

```
5'...GCAGTGNN...3'

3'...CGTCACNN...5'.
```

103. The kit of embodiment 101 or embodiment 102, wherein the restriction enzyme is Nb.BtsI or BtsI-v2 or a derivative thereof.

104. The kit of any one of embodiments 75-103, further comprising a binding agent capable of binding to a universal feature of the macromolecules, wherein the binding agent comprises a capping sequence.

105. The kit of any one of embodiments 75-104, wherein the kit comprises a mixture comprising a plurality of binding agents.

106. The kit of any one of embodiments 75-105, wherein the binding agent is a polypeptide or a protein.

107. The kit of embodiment 106, wherein the binding agent is an aminopeptidase or variant, mutant, or modified protein thereof; an aminoacyl tRNA synthetase or variant, mutant, or modified protein thereof; an anticalin or variant, mutant, or modified protein thereof; a ClpS, ClpS2, or variant, mutant, or modified protein thereof; a UBR box protein or variant, mutant, or modified protein thereof; or a modified small molecule that binds amino acid(s), i.e. vancomycin or a variant, mutant, or modified molecule thereof; or an antibody or binding fragment thereof; or any combination thereof.

108. The kit of any one of embodiments 77-107, wherein the binding agent binds to a single amino acid residue, a dipeptide, a tripeptide or a post-translational modification of a polypeptide macromolecule.

109. The kit of embodiment 108, wherein the binding agent is configured to bind to an N-terminal amino acid residue of the polypeptide.

110. The kit of any one of embodiments 80-109, wherein the binding agent is configured to bind to an N-terminal amino acid residue of the polypeptide that is modified by the reagent for modifying the terminal amino acid of the polypeptide.

111. The kit of any one of embodiments 75-110, further comprising one or more wash buffers.

112. The kit of any one of embodiments 75-111, further comprising a support for immobilizing the macromolecule and/or the recording tag.

113. The kit of embodiment 112, wherein the support is a three-dimensional support (e.g., a porous matrix or a bead).

114. The kit of embodiment 113, wherein the support comprises a polystyrene bead, a polyacrylate bead, a polymer bead, an agarose bead, a cellulose bead, a dextran bead, an acrylamide bead, a solid core bead, a porous bead, a paramagnetic bead, a glass bead, a controlled pore bead, a silica-based bead, or any combination thereof.

V. EXAMPLES

The following examples are offered to illustrate but not to limit the methods, compositions, and uses provided herein. Certain aspects of the present invention, including, but not limited to, embodiments for the Proteocode™ polypeptide sequencing assay, information transfer between coding tags and recording tags, methods of making nucleotide-polypeptide conjugates, methods for attachment of nucleotide-polypeptide conjugates to a support, methods of generating barcodes, methods of generating specific binders recognizing an N-terminal amino acid of a polypeptide, reagents and methods for modifying and/or removing an N-terminal amino acid from a polypeptide, methods for analyzing extended recording tags were disclosed in earlier published application US 2019/0145982 A1, US 2020/0348308 A1, US 2020/0348307 A1, US 2021/0208150 A1, WO 2020/223000, the contents of which are incorporated herein by reference in their entireties.

Example 1. Assessment of Analyte Immobilization Using Nucleic Acid Hybridization and Joining to a Solid Support This example describes exemplary methods for joining (immobilizing) nucleic acid-polypeptide conjugates to a solid support.

In a hybridization based method of immobilization, nucleic acid-polypeptide conjugates were hybridized and ligated to hairpin capture DNAs that were chemically immobilized on magnetic beads. The capture nucleic acids were conjugated to the beads using trans-cyclooctene (TCO) and methyltetrazine (mTet)-based click chemistry. TCO-modified short hairpin capture nucleic acids (16 basepair stem, 5 base loop, 24 base 5' overhang) were reacted with mTet-coated magnetic beads. Phosphorylated nucleic acid-polypeptide conjugates (10 nM) were annealed to the hairpin DNAs attached to beads in 5×SSC, 0.02% SDS, and incubated for 30 minutes at 37° C. The beads were washed once with PBST and resuspended in 1×Quick ligation solution (New England Biolabs, USA) with T4 DNA ligase. After a 30-minute incubation at 25° C., the beads were washed twice with PBST and resuspended in the 50 µL of PBST. The total immobilized nucleic acid-polypeptide conjugates including amino FA-terminal peptides (FAGVAMPGAE-DDVVGSGSK; SEQ ID NO: 3), amino AFA-terminal peptides (AFAGVAMPGAEDDVVGSGSK; SEQ ID NO: 4), and an amino AA-terminal peptides (AAGVAMPGAE-DDVVGSGSK; SEQ ID NO: 5) were quantified by qPCR using specific primer sets. For comparison, peptides were immobilized onto beads using a non-hybridization based method that did not involve a ligation step. The non-hybridization based method was performed by incubating 30 µM TCO-modified DNA-tagged peptides including amino FA-terminal peptides, amino AFA-terminal peptides, and amino AA-terminal peptides, with mTet-coated magnetic beads overnight at 25° C.

As shown in Table 1, similar Ct values were observed in the non-hybridization preparation method with 1:100,000 grafting density and the hybridization based preparation method with 1:10,000 grafting density. Loading amount of DNA-tagged peptides for the hybridization based preparation method was 1/3000 compared to that for the non-hybridization preparation method. In general, it was observed that less starting material was needed for the hybridization based immobilization method.

TABLE 1

| Comparison of Loading Hybridization and Non-hybridization Immobilization Methods | | |
|---|---|---|
| Grafting:Passivation | Non-hybridization based immobilization method (−Ligation) | Hybridization based immobilization method (+Ligation) |
| 1:100,000 | 19.4 | 25.4 |
| 1:10,000 | — | 21.1 |

Example 2. Exemplary Sequential Encoding Assay

In this example two exemplary binding agents were used to specifically bind to nucleic acid-polypeptide conjugates immobilized on a solid support. One binding agent binds to N-terminal phenylalanine residues of polypeptides (F-binder; 31-F), and the other binding agent binds to N-terminal leucine residues of polypeptides (L-binder; 44-L). Both binding agents were engineered from lipocalin scaffolds by directed evolution, specifically as described in Example 1 of US 2021/0208150 A1. The binding agents were conjugated to corresponding nucleic acid coding tags comprising barcodes with identifying information regarding the binding agent. The coding tags specific for each binding agent were attached to SpyTag via a PEG linker, and the resulting fusions were reacted with binding agent-Spy-Catcher fusion protein via SpyTag-SpyCatcher interaction, essentially as described in US 2021/0208150 A1.

For encoding assay, two test macromolecules (FSG-VARGDVRGGK(azide); hereafter F-peptide; SEQ ID NO: 6 and LAESAFSGVARGDVRGGK(azide); hereafter L-peptide; SEQ ID NO: 7) were joined to immobilized bead-attached capture DNA (SEQ ID NO: 8) via a alkyne-azide reaction (essentially as described in Example 1). DNA-polypeptide conjugates (20 nM) were annealed to the capture DNAs attached to beads in 5×SSC, 0.02% SDS, and incubated for 30 minutes at 37° C. The beads were washed once with PBST and resuspended in 1×Quick ligation solution (New England Biolabs, USA) with T4 DNA ligase. After a 30-minute incubation at 25° C., and the beads were washed with PBST, two times of 0.1M NaOH+0.1% Tween 20 and twice of PBST. The recording tags in the conjugates contain a barcode for the macromolecule, 2 nt overhang complementary region, Type II restriction enzyme binding region, and flanking region. After hybridization and ligation, the samples were incubated with Klenow fragment (3'→5' exo-) (MCLAB, USA), BtsI-V2 (0.5 U/uL, New England Biolabs, USA), dNTPs (each at 125 uM), and CutSmart buffer (50 mM Potassium acetate, 20 mM Tris-acetate, 10 mM Magnesium acetate, 100 μg/ml BSA, pH 7.9, New England Biolabs, USA) at 25° C. for 30 min and washed with PBST, twice of 0.1M NaOH+0.1% Tween 20 and twice of PBST. As a result, 2nt overhang at 3' was generated (see FIG. 1A).

The beads were treated with 18 mM PMI reagent (pyra-zole methanimine, 4-trifluoromethyl-1H-pyrazole) in DMA and MOPS mixture (60% DMA and 40% MOPS, pH 7.6) at 25° C. for 30 min to modify the N-terminal of the immobilized peptides and washed with PBST for 3 times. The coding tags attached to the F-binder and L-binder each form a loop with 8 bp duplex and 2 nt overhang at the 3', which is complementary to the 3' overhang of the recording tag on the beads. The coding tags contain unique barcodes for identification of the binders, and also have the BtsI-V2 binding sequence and the 2 nt complimentary overhang region for the next binding cycle. The two binding agents (100 nM each) were incubated with the beads in presence of 0.125 U/uL of Klenow fragment (3'→5' exo-) (MCLAB, USA), dNTP mixture (125 uM of each), 0.5 U/uL of BtsI-V2, and as well as different concentrations of T4 DNA ligase ((New England Biolabs, USA) in the quick ligase buffer (66 mM Tris-HCl, 10 mM MgCl2, 1 mM Dithiothrei-tol, 1 mM ATP, 7.5% Polyethylene glycol (PEG6000), pH at 7.6) at 25° C. for 15 min, followed by washes of PB ST once, twice of 0.1M NaOH+0.1% Tween 20, and twice of PB ST. During binding, extension of recording tags has occurred, which resulted in transfer of barcode information from the coding tag to the recording tag, forming extended recording tags (see FIG. 1B).

After the binding cycle, capping was performed to introduce a primer site for downstream PCR that will amplify extended recording tags for analysis. Capping oligos was introduced that contain a loop DNA with 2 nt 3' overhang complimentary to the 3' overhang of the extended or unextended recording tags. Instead of performing a separate capping step, a primer site for downstream PCR can be introduced during the extension reaction using a longer coding tags that contain a complementary primer sequence. 400 nM of capping oligos were incubated with the beads in presence of 12.5 U/uL of T4 DNA ligase in the quick ligase buffer (66 mM Tris-HCl, 10 mM MgCl$_2$, 1 mM Dithiothrei-tol, 1 mM ATP, 7.5% Polyethylene glycol (PEG6000), pH at 7.6) at 25° C. for 15 min. The sample were washed with 1 time of PBST, twice of 0.1M NaOH+0.1% Tween 20, and twice of PBST. The extended recording tags of the assay were subjected to PCR amplification and analyzed by next-generation sequencing (NGS), revealing barcode information about binding agents that were interacted with the macromolecules.

Figure 2:
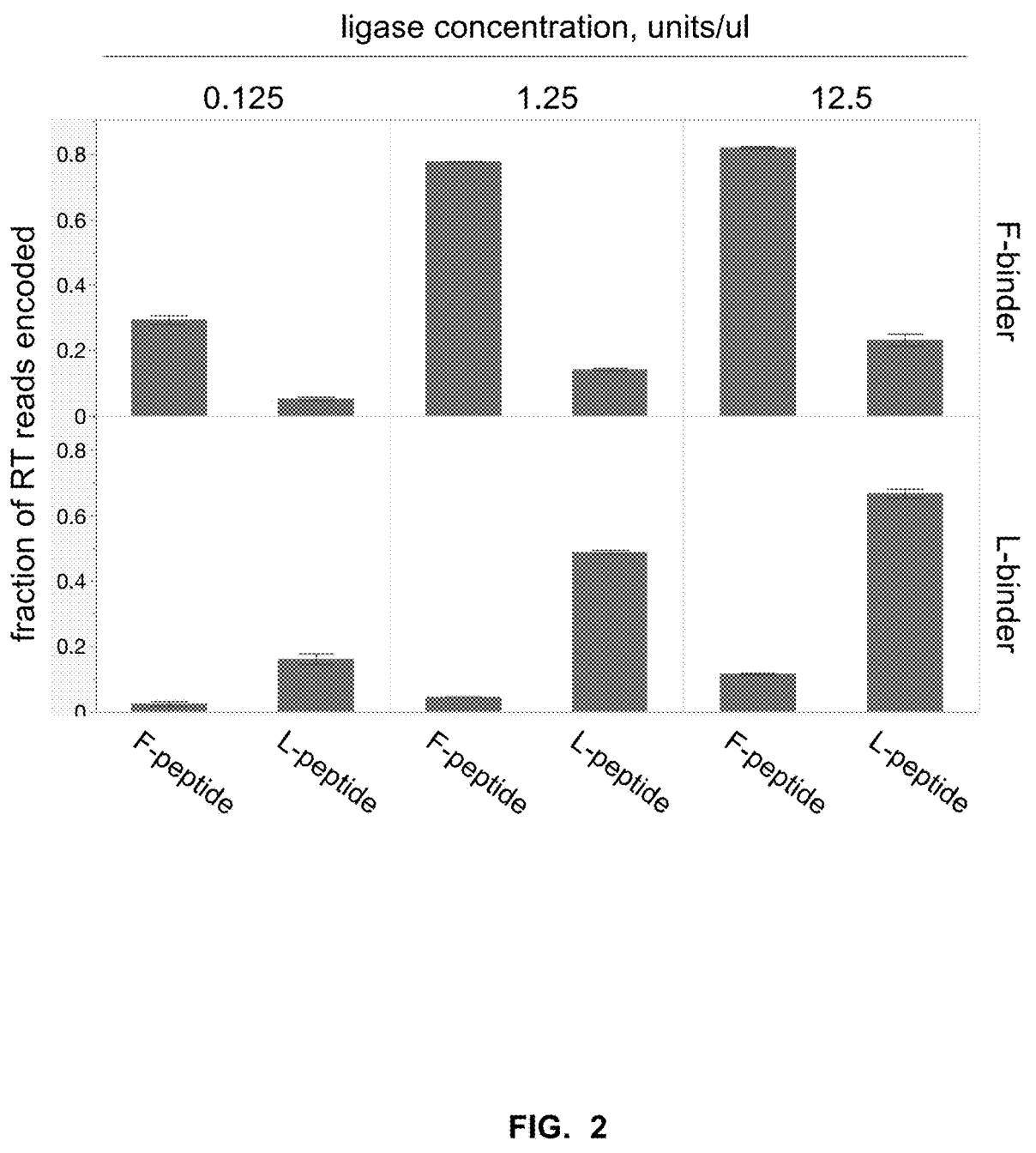

Exemplary encoding results generated by the described encoding method are shown in FIG. 2. For ligation step, 3 different concentrations of T4 DNA ligase (0.125, 1.25, 12.5 units/up were tested. After ligation, Klenow fragment was added for the extension step and BtsI-V2 enzyme was added for the cleavage step. Fractions of encoded recording tags (percentage of extended recording tags to total amount of recording tags on the beads (extended and unextended)) were evaluated by NGS sequencing and showed specific encoding results for both binding agents.

Example 3. Encoding Assay for Other Types of Macromolecules

Data shown in FIG. 2 represent analysis of the extended recording tags and confirm successful transfer of barcode information from the coding tags to the recording tags after binding of the F-binder or L-binder to the peptide macromolecules. The described techniques can be adopted for other types of macromolecules, such as lipid, carbohydrate or macrocycle. To perform encoding assay, such macromolecules need to be immobilized on a solid support (such as beads) and associated with nucleic acid recording tag. The encoding steps remain the same regardless of the type of the macromolecule immobilized. The association with the recording tag can be direct (such as covalent attachment) or indirect (such as association through a solid support). In the latter case, the recording tag should co-localize or be in a close proximity with the macromolecule during the encoding assay. Binding agents can be chosen to bind specifically to a component of the macromolecule. Each binding agent needs to be conjugated to corresponding nucleic acid coding tag that contains a barcode with identifying information regarding the binding agent. During encoding, the barcode information is transferred to the recording tag associated with the macromolecule, generating the extended recording tag, so that binding history of the macromolecule is recorded into the extended recording tag. The binding cycle can be repeated multiple times using different binding agents interacting with the macromolecule, either separately, or in a mixture. Below, representative methods known in the art are disclosed that can be utilized for adaptation of the disclosed encoding assay for macromolecules of different types, such as a carbohydrate, a lipid or a macrocycle.

First, exemplary binding agents that can specifically bind to components of a carbohydrate, a lipid or a macrocycle are known. For example, lectins are carbohydrate-binding proteins that can selectively recognize glycan epitopes of free carbohydrates or glycoproteins, and can be utilized as specific binding agents for macromolecules that contain carbohydrates. Importantly, there are known lectins that recognize different components of carbohydrates, such as mannose-binding lectins, galactose/N-acetyl glucosamine-binding lectins, sialic acid/N-acetyl glucosamine-binding lectins, fucose-binding lectins (disclosed for example, in WO 2012/049285 A1). Also, lipid-binding proteins are well-known and can be utilized as binding agents (see, for example, Bernlohr D A, et al., Intracellular lipid-binding proteins and their genes. Annu Rev Nutr. 1997; 17:277-303). Lipid-binding antibodies are commonly known and can be utilized as binding agents for macromolecules that contain lipids (see, for example, Alving CR. Antibodies to lipids and liposomes: immunology and safety. J Liposome Res. 2006; 16(3):157-66). Furthermore, proteins that specifically bind to macrocycles are also known (see, for example, Villar E A, et al., How proteins bind macrocycles. Nat Chem Biol. 2014 September; 10(9):723-31; Hunter™, et al., Protein recognition of macrocycles: binding of anti-HIV metallocyclams to lysozyme. Proc Natl Acad Sci USA. 2005 Feb. 15; 102(7): 2288-92).

Second, an exemplary carbohydrate detection encoding assay can be performed as follows, utilizing methods known in the art.

Approach I. Reductive amination (based on Yang S J, Zhang H. Glycan analysis by reversible reaction to hydrazide beads and mass spectrometry. Anal Chem. 2012; 84(5): 2232-2238).

(a) Generate an immobilized recording tag-attached carbohydrate conjugate. Oxidize carbohydrates with sodium periodate to generate an aldehyde. Conjugate amine terminated DNA recording tag and reduce the resulting imine using sodium cyanoborohydride to generate a carbohydrate-recording tag conjugate. Preferably, hydrazide, alkoxyamine, or similarly reactive DNA may be employed to generate more stable reaction products (e.g., hydrazones) that do not require reducing agents. Immobilize DNA-coupled carbohydrate to a solid support via the DNA recording tag as described in Example 2, (b) Generate lectin-DNA coding tag (the binding agent-coding tag) conjugates by utilizing SpyCatcher-concanavalin A (ConA) fusion as described earlier. Coding tag contains a barcode with identifying information regarding ConA.

(c) Transfer barcode information from lectin-associated coding tag to the recording tag as described in Example 2, thus analyzing whether the carbohydrate contains a component that binds to ConA.

Approach II. Diazo coupling (based on Matsuura K, et al., Facile synthesis of stable and lectin-recognizable DNA-carbohydrate conjugates via diazo coupling. Bioconjug Chem. 2000 March-April; 11(2):202-11). In approach II, step (a) (immobilization of recording tag-attached carbohydrate conjugate) can be performed as follows. 1) Aminate carbohydrate with ammonium hydrogen carbonate in water to generate β-glycosylamines; 2) Convert amine to amide with carboxylate derivatives bearing a nitrophenyl functionality. Hydrogenate nitro groups over palladium catalyst and treat with $NaNO_2$ and HCl to provide the diazo compounds.

Steps (b) and (c) are the same as in the in approach I.

Third, an exemplary lipid detection encoding assay can be performed as follows, utilizing methods known in the art.

Approach I. Fatty acids (based on Hiroshi Miwa, High-performance liquid chromatographic determination of free fatty acids and esterified fatty acids in biological materials as their 2-nitrophenylhydrazides, Analytica Chimica Acta, Volume 465, Issues 1-2, 2002, Pages 237-255, ISSN 0003-2670).

(a) Extract fatty acids from a biological source and activate carboxylic acid with EDC/CDI chemistry. Couple amine- or hydrazide-terminated DNA recording tag to generate a recording tag-attached lipid conjugate. immobilize DNA-coupled lipid to a solid support via the DNA recording tag as described in Example 2.

Approach II, Reactive lipids (based on X. Wei & H. Yin (2015) Covalent modification of DNA by α, β-unsaturated aldehydes derived from lipid peroxidation: Recent progress and challenges, Free Radical Research, 49:7, 905-917).

(a) Obtain a reactive lipid substrate such as malondialdehyde (MDA) or 4-hydroxynonenal (HNE); couple hydrazide-terminated DNA recording tag to reactive lipid species. Alternatively, couple amine-terminated DNA recording tag to aldehyde on reactive lipid and reduce resulting imine with sodium cyanoborohydride.

In the next step for both approaches, generate a binding agent-DNA coding tag conjugate by utilizing SpyCatcher-binding agent fusion as described earlier. Coding tag contains a barcode with identifying information regarding the binding agent. Fatty acid-binding protein (FABP), other lipid binding proteins or lipid binding antibodies can be used as a binding agent. Finally, transfer barcode information from binding agent-associated coding tag to the recording tag as described in Example 2 of the present application, thus analyzing whether the lipid contains a component that binds to the binding agent.

Forth, an exemplary macrocycle (microcystin) detection encoding assay can be performed as follows, utilizing methods known in the art, based on McElhiney J, et al., Rapid isolation of a single-chain antibody against the cyanobacterial toxin microcystin-LR by phage display and its use in the immunoaffinity concentration of microcystins from water. Appl Environ Microbiol. 2002 November; 68(11):5288-95.

(a) Generate DNA recording tag-coupled microcystin by reacting dehydroalanine of microcystin with 2-mercaptoethylamine to generate a primary amine, followed by coupling DNA recording tag to primary amine using an amine reactive DNA recording tag (e.g., NHS-DNA derivative).

(b) Generate single chain antibody-SpyCatcher binding agent that recognizes microcystin. Single chain antibody production is described in McElhiney J, et al, 2002. Couple DNA coding tag to SpyTag (the coding tag contains a barcode with identifying information regarding the single chain antibody), followed by reacting with SpyCatcher to generate the binding agent-coding tag conjugate as described earlier.

(c) Transfer barcode information from single chain anti-
body-associated coding tag to the recording tag as
described in Example 2, thus analyzing whether the
macromolecule contains microcystin.

SEQUENCE TABLE

| SEQ ID NO | Sequence (5'-3') | Description |
|---|---|---|
| 1 | AATGATACGGCGACCACCGA | P5 primer |
| 2 | CAAGCAGAAGACGGCATACGAGAT | P7 primer |
| 3 | FAGVAMPGAEDDVVGSGSK | Test peptide |
| 4 | AFAGVAMPGAEDDVVGSGSK | Test peptide |
| 5 | AAGVAMPGAEDDVVGSGSK | Test peptide |
| 6 | FSGVARGDVRGGK(azide) | F-peptide |
| 7 | LAESAFSGVARGDVRGGK(azide) | L-peptide |
| 8 | /5Phos/TGT AGG GAA AGA GTG TTT/<br>iAmMC6T/T/iSpC3/A<br>CAC TCT TTC CCT ACA CGA CGC TCTTCC GAT CT | Capture DNA |

What is claimed is:

1. A method for analyzing a macromolecule, comprising the steps of:
   (a) providing a macromolecule and an associated record-ing tag joined to a support, wherein the recording tag comprises a double stranded region;
   (b) contacting the macromolecule with a binding agent, wherein the binding agent comprises a coding tag with identifying information regarding the binding agent, wherein the binding agent binds to the macromolecule;
   (c) covalently joining the 5' end of the recording tag to the 3'end of the coding tag by a nucleic acid joining reagent;
   (d) following (c), extending the recording tag using the coding tag as a template for a polymerase, thereby generating a double stranded extended recording tag; and
   (e) cleaving both strands of the double stranded extended recording tag with a double strand nucleic acid cleaving reagent to generate a 3' overhang in the extended recording tag, wherein a length of the 3' overhang in the extended recording tag is less than 6 base pairs;
   whereby information is transferred from the coding tag to the recording tag to generate the extended recording tag.

2. The method of claim 1, wherein in step (d), the double strand nucleic acid cleaving reagent recognizes a recognition sequence of the double stranded extended recording tag.

3. The method of claim 1, wherein the cleavage in step (e) releases the binding agent from the macromolecule.

4. The method of claim 1, wherein steps (b), (c), (d) and (e) are repeated sequentially one or more times in a cyclic manner.

5. The method of claim 1, wherein the macromolecule is a polypeptide.

6. The method of claim 5, wherein the polypeptide is obtained by fragmenting a protein from a biological sample.

7. The method of claim 4, further comprising removing a portion of the macromolecule prior to repeating step (b).

8. The method of claim 5, further comprising removing an N-terminal amino acid (NTAA) of the polypeptide to expose a new NTAA of the polypeptide prior to repeating step (b).

9. The method of claim 4, wherein the 3' overhang of the extended recording tag generated by the double strand nucleic acid cleaving reagent in step (e) is available to hybridize with a second coding tag when step (b) is repeated.

10. The method of claim 1, wherein in step (b), the macromolecule is contacted with a plurality of binding agents, wherein the plurality of binding agents comprises the binding agent, and each binding agent of the plurality of binding agents comprises a coding tag with identifying information regarding the corresponding binding agent.

11. The method of claim 5, further comprising treating the polypeptide with a reagent for modifying a terminal amino acid of the polypeptide prior to step (b).

12. The method of claim 1, wherein the recording tag associated with the macromolecule comprises a nucleic acid hairpin.

13. The method of claim 1, wherein the nucleic acid joining reagent of step (c), the polymerase of step (d) and the double strand nucleic acid cleaving reagent of step (e) are provided simultaneously.

14. The method of claim 1, wherein the double strand nucleic acid cleaving reagent is a type IIS restriction enzyme.

15. The method of claim 1, further comprising analyzing one or more of the extended recording tags, wherein ana-lyzing the extended recording tag(s) comprises a nucleic acid sequencing method.

* * * * *

SEQUENCE LISTING

<160> NUMBER OF SEQ ID NOS: 8

<210> SEQ ID NO 1
<211> LENGTH: 20
<212> TYPE: DNA
<213> ORGANISM: Artificial Sequence
<220> FEATURE:
<223> OTHER INFORMATION: P5 primer

<400> SEQUENCE: 1
aatgatacgg cgaccaccga                                                    20

<210> SEQ ID NO 2
<211> LENGTH: 24
<212> TYPE: DNA
<213> ORGANISM: Artificial Sequence
<220> FEATURE:
<223> OTHER INFORMATION: P7 primer

<400> SEQUENCE: 2
caagcagaag acggcatacg agat                                               24

<210> SEQ ID NO 3
<211> LENGTH: 19
<212> TYPE: PRT
<213> ORGANISM: Artificial Sequence
<220> FEATURE:
<223> OTHER INFORMATION: Test peptide

<400> SEQUENCE: 3

Phe Ala Gly Val Ala Met Pro Gly Ala Glu Asp Asp Val Val Gly Ser
1               5                   10                  15

Gly Ser Lys

<210> SEQ ID NO 4
<211> LENGTH: 20
<212> TYPE: PRT
<213> ORGANISM: Artificial Sequence
<220> FEATURE:
<223> OTHER INFORMATION: Test peptide

<400> SEQUENCE: 4

Ala Phe Ala Gly Val Ala Met Pro Gly Ala Glu Asp Asp Val Val Gly
1               5                   10                  15

Ser Gly Ser Lys
            20

<210> SEQ ID NO 5
<211> LENGTH: 19
<212> TYPE: PRT
<213> ORGANISM: Artificial Sequence
<220> FEATURE:
<223> OTHER INFORMATION: Test peptide

<400> SEQUENCE: 5

Ala Ala Gly Val Ala Met Pro Gly Ala Glu Asp Asp Val Val Gly Ser
1               5                   10                  15

Gly Ser Lys

<210> SEQ ID NO 6
<211> LENGTH: 13
<212> TYPE: PRT
<213> ORGANISM: Artificial Sequence
<220> FEATURE:
<223> OTHER INFORMATION: F-peptide
<220> FEATURE:
<221> NAME/KEY: MISC_FEATURE
<222> LOCATION: (13)..(13)
<223> OTHER INFORMATION: an azido substituent on the lysine side chain

<400> SEQUENCE: 6

Phe Ser Gly Val Ala Arg Gly Asp Val Arg Gly Gly Lys
1               5                   10

<210> SEQ ID NO 7
<211> LENGTH: 18
<212> TYPE: PRT
<213> ORGANISM: Artificial Sequence
<220> FEATURE:
<223> OTHER INFORMATION: L-peptide
<220> FEATURE:
<221> NAME/KEY: MISC_FEATURE
<222> LOCATION: (18)..(18)
<223> OTHER INFORMATION: an azido substituent on the lysine side chain

<400> SEQUENCE: 7

Leu Ala Glu Ser Ala Phe Ser Gly Val Ala Arg Gly Asp Val Arg Gly
1               5                   10                  15

Gly Lys

<210> SEQ ID NO 8
<211> LENGTH: 53
<212> TYPE: DNA
<213> ORGANISM: Artificial Sequence
<220> FEATURE:
<223> OTHER INFORMATION: Capture DNA
<220> FEATURE:
<221> NAME/KEY: misc_feature
<222> LOCATION: (1)..(1)
<223> OTHER INFORMATION: 5'-phosphorylated
<220> FEATURE:
<221> NAME/KEY: misc_feature
<222> LOCATION: (19)..(19)
<223> OTHER INFORMATION: n is an internal 5'-amino modifier C6 dT
<220> FEATURE:
<221> NAME/KEY: misc_feature
<222> LOCATION: (20)..(21)
<223> OTHER INFORMATION: C3 (three carbon) spacer inserted in between -continued

```
<400> SEQUENCE: 8
tgtagggaaa gagtgtttnt acactctttc cctacacgac gctcttccga tct          53
```